(12) United States Patent
Moriya et al.

(10) Patent No.: US 7,727,998 B2
(45) Date of Patent: Jun. 1, 2010

(54) MELANIN-CONCENTRATING HORMONE RECEPTOR ANTAGONISTS CONTAINING PIPERIDINE DERIVATIVES AS THE ACTIVE INGREDIENT

(75) Inventors: Minoru Moriya, Tsukuba (JP); Toshihiro Sakamoto, Moriya (JP); Makoto Ishikawa, Ushiku (JP); Akio Kanatani, Ushiku (JP); Takehiro Fukami, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 961 days.

(21) Appl. No.: 10/544,261

(22) PCT Filed: Feb. 9, 2004

(86) PCT No.: PCT/JP2004/001326

§ 371 (c)(1),
(2), (4) Date: Jan. 17, 2006

(87) PCT Pub. No.: WO2004/069798

PCT Pub. Date: Aug. 19, 2004

(65) Prior Publication Data

US 2006/0106046 A1  May 18, 2006

(30) Foreign Application Priority Data

Feb. 10, 2003  (JP) .............................. 2003-032123

(51) Int. Cl.
*A61K 31/4545* (2006.01)
*C07D 491/10* (2006.01)

(52) U.S. Cl. .......................................... 514/278; 546/16
(58) Field of Classification Search ................. 514/278; 546/16
See application file for complete search history.

(56) References Cited

U.S. PATENT DOCUMENTS

| | | | |
|---|---|---|---|
| 6,472,394 B1 | 10/2002 | McKittrick et al. | |
| 6,569,861 B2 | 5/2003 | Bakthavatchalam et al. | |
| 6,664,273 B2 | 12/2003 | Burnett et al. | |
| 6,720,324 B2 | 4/2004 | Marzabadi et al. | |
| 6,727,264 B1 | 4/2004 | Marzabadi et al. | |
| 6,818,772 B2 | 11/2004 | Kym et al. | |
| 6,887,889 B2* | 5/2005 | Hobbs et al. | 514/331 |
| 6,900,329 B2 | 5/2005 | Clader et al. | |
| 6,906,075 B2 | 6/2005 | DeSimone et al. | |
| 6,930,185 B2 | 8/2005 | Ishihara et al. | |
| 7,335,665 B2* | 2/2008 | Marzabadi et al. | 514/278 |
| 2002/0072604 A1 | 6/2002 | Carpino et al. | |
| 2003/0023085 A1 | 1/2003 | Chen et al. | |
| 2003/0105094 A1 | 6/2003 | Clader et al. | |
| 2003/0144261 A1 | 7/2003 | Palani et al. | |
| 2003/0158177 A1 | 8/2003 | Ishihara et al. | |
| 2003/0212070 A1 | 11/2003 | Schwink et al. | |
| 2004/0024002 A1 | 2/2004 | Burnett et al. | |
| 2004/0063700 A1 | 4/2004 | Cheng et al. | |
| 2004/0106645 A1 | 6/2004 | Blackburn et al. | |
| 2004/0220404 A1 | 11/2004 | Carpenter et al. | |
| 2005/0049269 A1 | 3/2005 | Wu et al. | |
| 2005/0182068 A1 | 8/2005 | Hutchison et al. | |
| 2006/0173027 A1* | 8/2006 | Marzabadi et al. | 514/278 |

FOREIGN PATENT DOCUMENTS

| | | |
|---|---|---|
| EP | 1219294 | 7/2002 |
| EP | 1447402 | 8/2004 |
| JP | 11-507344 | 1/1993 |
| JP | 2001 226269 | 8/2001 |
| JP | 2002 003370 A | 1/2002 |
| JP | 2002 371059 | 12/2002 |
| WO | WO 96/40136 | 12/1996 |
| WO | WO 01/21169 | 3/2001 |
| WO | WO 01/21577 | 3/2001 |
| WO | WO 01/82925 | 8/2001 |
| WO | WO 02/00654 | 1/2002 |
| WO | WO 02/02744 | 1/2002 |
| WO | WO 02/06245 | 1/2002 |
| WO | WO 02/076929 | 10/2002 |
| WO | WO 02/088089 | 11/2002 |

(Continued)

OTHER PUBLICATIONS

RN 1026906-40-0 Registry (2008).*

(Continued)

*Primary Examiner*—Celia Chang
(74) *Attorney, Agent, or Firm*—Janet E. Fair; John C. Todaro

(57) ABSTRACT

The invention provides melanin-concentrating hormone receptor antagonists containing as the active ingredient piperidine derivatives represented by the general formula [I]:

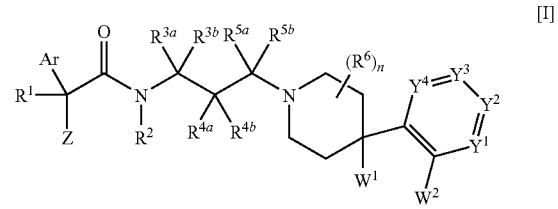

[wherein $R^1$ is hydrogen, hydroxyl, lower alkyl, or the like; $R^2$, $R^{3a}$, $R^{3b}$, $R^{4a}$, $R^{4b}$, $R^{5a}$, $R^{5b}$ and $R^6$ each stands for hydrogen, halogen, or the like; $W^1$ and $W^2$ each independently stands for —O—, —$CH_2$—, or the like; $Y^1$, $Y^2$, $Y^3$ and $Y^4$ stand for —CH—, —CF—, —N—, or the like; Z stands for lower alkyl, an aliphatic heterocyclic group, or the like; Ar is a mono- or bi-cyclic aliphatic heterocycle or an aromatic heterocycle; and n is an integer of 1 to 8]. The compounds act as antagonist against melanin-concentrating hormone receptor and are useful as drugs for central diseases, circulatory diseases, or metabolic diseases.

11 Claims, No Drawings

FOREIGN PATENT DOCUMENTS

| WO | WO 03/028641 |   | 4/2003  |
|----|--------------|---|---------|
| WO | WO 03/045313 |   | 6/2003  |
| WO | WO 03/045920 |   | 6/2003  |
| WO | WO 03/070244 |   | 8/2003  |
| WO | WO 03/087044 |   | 10/2003 |
| WO | WO 03/087045 |   | 10/2003 |
| WO | WO 03/087046 |   | 10/2003 |
| WO | WO 03/097047 |   | 11/2003 |
| WO | WO2004/004714 | * | 1/2004 |
| WO | WO 2004/004714 |  | 1/2004 |
| WO | WO 2004/028459 |  | 4/2004 |
| WO | WO 2004/043958 |  | 5/2004 |

OTHER PUBLICATIONS

Roufos et al., J. Med. Chem., (1996), vol. 39(7), pp. 1514-1520, "A structure—Activity relationship study of novel phenylacetamides which are sodium channel blockers".

Dyke et al., Exp. Opin. Ther. Patents (2005), vol. 15, pp. 1303-1313, "Recent developments in the discovery of MCH-1R antagonists for the treatment of obesity—an update".

Kowalski et al., Exp. Opin. Ther. Patents (2004), vol. 13, pp. 1113-1122, "Therapeutic potential of melanin-concentrating hormone-1 receptor antagonists for the treatment of obesity".

Clark et al., J. Med. Chem., (2004), vol. 47, pp. 3962-3971, "A virtual screening approach to finding novel and potent antagonists at the melanin-concentrating hormone 1 receptor".

Arienzo et al., Bioorg. & Medicinal Chem. Letters, (2004), vol. 14, pp. 4099-4102, "Structure-activity relationships of a novel series of melanin-concentrating hormone (MCH) receptor antagonists".

Mohammad R. Marzabadi et al., U.S. Appl. No. 10/189,146 filed Jul. 3, 2002.

Patane, M. A. et al., "Phenylacetamides as Selective Alpha-1A Adreergic Receptor Antagonists", Bioorgainc & Medicinal Chemistry Letters, 2000, pp. 1621-1624, vol. 10.

* cited by examiner

MELANIN-CONCENTRATING HORMONE RECEPTOR ANTAGONISTS CONTAINING PIPERIDINE DERIVATIVES AS THE ACTIVE INGREDIENT

CROSS-REFERENCE TO RELATED APPLICATIONS

This application is a U.S. National Phase application under 35 U.S.C. §371 of PCT Application No. PCT/JP2004/001326, filed Feb. 9, 2004, which claims priority under 35 U.S.C. §365(b) from Japanese patent application No. JP2003-32123, filed Feb. 10, 2003.

TECHNICAL FIELD

This invention relates to piperidine derivatives which are useful in the filed of medicines. Said compounds act as antagonists to melanin concentrating hormone receptor, and are useful as preventing or treating agents of various diseases of cardiovascular system, nervous system, metabolic systems, reproductive system, respiratory system, digestive system and the like.

BACKGROUND ART

Melanin concentrating hormone (hereafter abbreviated as "MCH") is a cyclic peptide hormone/neuro-peptide, which was for the first time isolated by Kawauchi, et al. in 1983 from sermon hypophysis [Nature, Vol. 305, 321 (1983)]. The hormone is known to functionally antagonize to melanin cell stimulating hormone in fishes, to cause concentration of melanin granules in melanophore and participate in body color change [International Review of Cytology, Vol. 126, 1(1991); Trends in Endocrinology and Metabolism, Vol. 5, 120 (1994)]. Also in mammals, MCH-containing neuron nerve cells are localized in the hypothalamus lateral field and uncertain zone, but their nerve fibers are projecting over a very wide scope in the brain [The Journal of Comparative Neurology, Vol. 319, 218 (1992)], and MCH is considered to preside over various central functions in living bodies.

Hypothalamus lateral field is known of old as feeding center, and furthermore, recently molecular biological and pharmacological knowledges suggesting participation of MCH in controlling energetic homeostasis are being accumulated. That is, it has been reported that expression of mRNA, which is a MCH precursor, was accelerated in brains of ob/ob mouse, db/db mouse, $A^y$/a mouse, Zucker fatty rat or the like which are model animals of hereditary obesity, or in brains of fasted mice [Nature, Vol. 380, 243 (1996); Diabetes, Vol. 47, 294 (1998); Biochemical and Biophysical Research Communications, Vol. 268, 88 (2000); Molecular Brain Research, Vol. 92, 43 (2000)].

Acute ventricular administration of MCH to rats was observed to induce accelerated feeding activity [Nature, Vol. 380, 243 (1996)] and chronic administration invites obesity accompanied by polyphagy [Proceedings of the National Academy of Science of the United States of America, Vol. 99, 3240, (2002)]. Moreover, MCH precursor gene-deficient mouse shows reduced food ingestion or rise in oxygen consumption per body weight compared to wild type mice. Its low body weight due to decrease in body fat was observed [Nature, Vol. 396, 670 (1998)].

On the contrary, transgenic mouse which expresses excessive MCH precursor develops obesity accompanied by polyphagy and insulin resistance [The Journal of Clinical Investigation, Vol. 107, 379 (2001)]. Consequently, it is suggested that MCH is an important factor for developing obesity and participates in diseases induced by metabolic disorder or respiratory diseases of which one of risk factors is obesity. Besides, MCH is known to participate also in anxiety-causing action, epilepsy, memory, learning, diuretic action, excretory action of sodium and potassium, oxytocin secreting action, reproduction and reproductive function [Peptides, Vol. 17, 171 (1996); Peptides, Vol. 18, 1095 (1997), Peptides, Vol, 15, 757 (1994); Journal of Neuroendocrinology, Vol. 8, 57 (1996); Critical Reviews in Neurobiology, Vol. 8, 221, (1994)].

MCH causes versatile pharmacological actions through MCH receptors which are present mainly in the central nervous system. As receptors of MCH, at least two types of type 1 receptors (MCH-1R or SLC-1) and type 2 receptors (MCH-2R or SLT) are known [Nature, Vol. 400, 261 (1999); Nature, Vol. 400, 265 (1999); Biochemical and Biophysical Research Communications, Vol. 261, 622 (1999); Nature Cell Biology, Vol. 1, 267 (1999); FEBS Letters, Vol. 457, 522 (1999); Biochemical and Physical Research Communications, Vol. 283, 1013 (2001); The Journal of Biological Chemistry, Vol. 276, 20125 (2001); Proceedings of the National Academy of Sciences of the United States of America, Vol. 98, 7564 (2001); Proceedings of the National Academy of Sciences of the United States of America, Vol. 98, 7576 (2001); The Journal of Biological Chemistry, Vol. 276, 34664 (2001); and Molecular Pharmacology, Vol. 60, 632 (2001)].

Of those, the pharmacological action observed on rodents is induced mainly via MCH-1R [Genomics, Vol. 79, 785 (2002)]. Because MCH-1R gene-deficient mice chronically administered with MCH do not develop polyphagy or obesity, it is known that controlling of energy exchange by MCH is induced via MCH-1R. Furthermore, deficiency of MCH-1R promotes activity amount of mouse [Proceedings of the National Academy of Sciences of the United States of America, Vol. 99, 3240 (2002)], and its participation in central diseases accompanied by behavioral disorder, for example, attention-deficit hyperactivity disorder, schizophrenia and the like also is strongly suggested [Molecular Medicine Today, Vol. 6, 43 (2000); Trends in Neuroscience, Vol. 24, 527 (2001)].

It is also reported that autoantibody to MCH-1R is present in serum of vitiligo vulgaris patient [The Journal of Clinical Investigation, Vol. 109, 923 (2002)]. Furthermore, expression of MCH-1R in certain species of cancer cells was reported, and in vivo expression sites of MCH and MCH-1R also suggest their participation in cancer, sleep, vigil, drug dependence and digestive disorders [Biochemical and Biophysical Research Communications, Vol. 289, 44 (2001); Neuroendocrinology, Vol. 61, 348 (1995); Endocrinology, Vol. 137, 561 (1996); The Journal of Comparative Neurology, Vol. 435, 26 (2001)].

Functions of MCH are expressed upon its binding to MCH receptors. Therefore, when its binding to MCH receptor is inhibited, expression of MCH action can be inhibited. In consequence, substances which are antagonists to binding of MCH with its receptor are useful as preventing or treating agent of those various diseases in which MCH participates, for example, metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

As compounds having analogous structures to those of the present invention compounds, for example, as compounds not having spiro ring, 1) those disclosed on J. Med. Chem., 39 (7) 1514-20 (1996) and 2) those disclosed in JP Announcement (Tokuhyo) Hei 11 (1999)-507344A can be named. Again, as the compounds having spiro ring, there are those disclosed in International Publication WO 02/088089 Pamphlet. However, those compounds do not have MCH-1R antagonizing action.

On the other hand, as to heretofore known antagonists to melanin-concentrating hormone receptor, descriptions are found in, for example, International Publications WO 01/21577 Pamphlet, WO 01/82925 Pamphlet, WO02/06245 Pamphlet, and WO 02/02744 Pamphlet; and in JP 2002-3370A. In particular, WO 02/02744 or WO 02/06245 disclose compounds having a spiro ring, but they differ from the compounds of the present invention at the carbon moiety adjacent to the amidic carbonyl group (CO) in general formula [I] of the present invention.

The object of the present invention is to provide piperidine derivatives which have an action to inhibit binding of MCH to MCH-1R, and also to provide preventing or treating agents utilizing them, of diseases such as metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

DISCLOSURE OF THE INVENTION

We have engaged in concentrative studies with the view to develop compounds which inhibit binding of MCH to MCH-1R, to discover that pyridine derivatives having specific spiro ring were novel substances and effective as MCH-1R antagonist. Pursuing the studies further, we discovered that piperidine derivatives having a structure in which the spiro ring moiety is open also have similar MCH-IR antagonizing action. The present invention is completed based on such discoveries.

Namely, the present invention relates to:

(1) an antagonist to melanin-concentrating hormone receptor which comprises as the active ingredient a piperidine derivative represented by the following general formula [I]

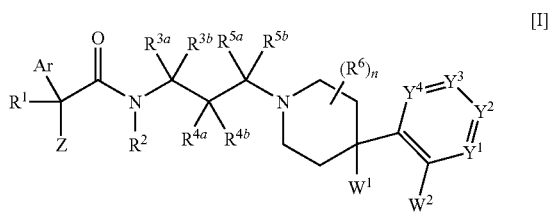

[in which $R^1$ stands for hydrogen, hydroxyl or optionally halogen-substituted lower alkyl, or $R^1$ and Z together form a 3 to 6-membered aliphatic carbocycle or aliphatic heterocycle, with the carbon atom to which they bind, said aliphatic carbocycle or aliphatic heterocycle optionally having a substituent group selected from Group α, $R^2$, $R^{3a}$, $R^{3b}$, $R^{5a}$ and $R^{5b}$ each independently stands for hydrogen or optionally halogen-substituted lower alkyl, $R^{4a}$ and $R^{4b}$ each independently stands for hydrogen, halogen, hydroxyl, or optionally halogen-substituted lower alkyl, $R^6$ each independently stands for hydrogen, halogen or optionally halogen-substituted lower alkyl, n stands for an integer of 1-8, $W^1$ and $W^2$ either each stands for hydrogen, or $W^1$ and $W^2$ together form O—CH$_2$—, —CH$_2$—CH$_2$— or —CH$_2$—O—, Z stands for lower alkyl or CY, or $R^1$ and Z together form a 3 to 6-membered aliphatic carbocycle or aliphatic heterocycle, with the carbon atom to which they bind, said aliphatic carbocycle or aliphatic heterocycle optionally having a substituent group selected from Group α, CY stands for a cyclic group optionally having one, two or more substituent groups selected from Group α, which group is selected from
1) 3 to 10-membered aliphatic carbocyclic groups,
2) 3 to 10-membered aliphatic heterocyclic groups,
3) 5 or 6-membered aromatic carbocyclic groups, and
4) 5 or 6-membered aromatic heterocyclic groups, $Y^1$, $Y^2$, $Y^3$ and $Y^4$ each independently stands for methyene which optionally has a substituent group selected from Group α, or nitrogen atom, with the proviso that not all of $Y^1$ to $Y^4$ are simultaneously nitrogen atoms, and Ar stands for a mono- or bicyclic aromatic carbocyclic or aromatic heterocyclic group which may have one, two or more substituent groups selected from Group β]

or its pharmaceutically acceptable salt:

[Group α]

halogen, hydroxyl, amino, nitro, oxo, mono-lower alkylamino, di-lower alkylamino, optionally halogen-substituted lower alkyl, optionally fluorine-substituted lower alkyloxy, lower cycloalkyloxy, lower alkyloxycabonyl, (lower alkyloxycarbonyl) amino, (lower alkyloxycarbonyl)lower alkylamino, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsulfamoyl)lower alkylamino and (di-lower alkylsulfamoyl) lower alkylamino.

[Group β]

nitro, aryloxy, lower cycloalkyl, lower cycloalkyloxy, lower alkylenedioxy, halogen, hydroxyl, optionally hydroxyl- or fluorine-substituted lower alkyl and optionally fluorine-substituted lower alkyloxy;

(2) an antagonist as set forth in (1) which comprises as the active ingredient a compound represented by the following general formula [I-1]

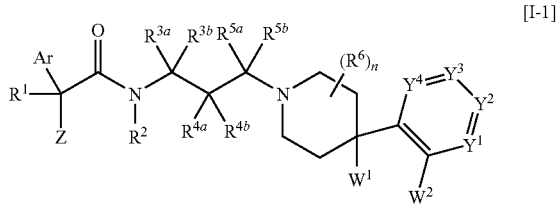

[in which $R^{1a}$ stands for hydrogen, hydroxyl, or optionally halogen-substituted lower alkyl, $W^3$ stands for —O— or —$CH_2$—, $W^4$ stands for —$CH_2$— or —O—, with the proviso that $W^3$ and $W^4$ are not —O— at the same time, and $R^2, R^{3a}, R^{3b}, R^{4a}, R^{4b}, R^{5a}, R^{5b}, R^6, Y^1, Y^2, Y^3, Y^4, CY, Ar$ and n have the same significations as above]; and (3) an antagonist as set forth in (1) which comprises as the active ingredient a compound represented by the following general formula [I-2]

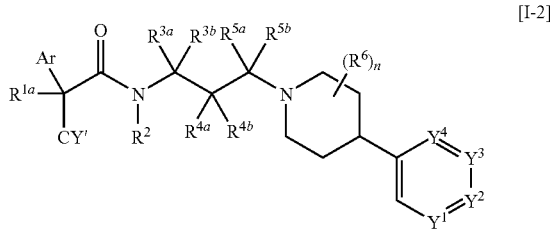

[in which CY' stands for a substituent selected from the group consisting of pyrrolyl, imidazolyl, lower alkylimidazolyl, 4-nitroimidazolyl, triazolyl, lower alkyltriazolyl, tetrazolyl, pyridonyl, 2-oxo-1-piperidinyl, 2-oxo-1-piperazinyl, 4-lower alkyl-2-oxo-1-piperazinyl, 4-lower alkylsulfonyl-2-oxo-1-piperazinyl and 4-lower alkylcarbonyl-2-oxo-1-piperazinyl, and $R^{1a}, R^2, R^{3a}, R^{3b}, R^{4a}, R^{4b}, R^{5a}, R^{5b}, R^6, Y^1, Y^2, Y^3, Y^4, Ar$ and n have the same significations as above].

The present invention furthermore provides:

(4) preventing or treating agent comprising the antagonist as set forth in (1) as the active ingredient, of metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation;

(5) compounds represented by the general formula [I-1];

(6) compounds represented by the general formula [I-2];

(7) process for preparing the compounds represented by the general formula [I], in particular, the compounds represented by the general formula [I-1] or [I-2]; and (8) pharmaceutical formulations comprising the compounds represented by the general formula [I-1] or [I-2], and pharmaceutically acceptable carrier.

Hereinafter the codes and terms used in the present specification are explained.

As "halogen", fluorine, chlorine, bromine and iodine can be named.

"Lower alkyl" includes $C_1$-$C_6$ alkyl, i.e., $C_1$-$C_6$ straight chain alkyl and $C_3$-$C_6$ branched chain alkyl, specific examples being methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like.

"Lower cycloalkyl" includes $C_3$-$C_6$ cycloalkyl, specific examples being cyclopropyl, cyclobutyl, cyclopentyl and cyclohexyl.

"Lower cycloalkyloxy" includes those groups in which $C_3$-$C_6$ cycloalkyl binds to oxygen, specific examples being cyclopropyloxy, cyclobutyloxy, cyclopentyloxy and cyclohexyloxy.

"Oxo" signifies a group which, together with a carbon atom in an organic compound, forms carbonyl. For example, as to $R^5$, it refers to the case where two $R^5$'s and the carbon atom to which they bind form a carbonyl group.

"Optionally fluorine-substituted lower alkyl" signifies lower alkyl or lower alkyl whose part or all of hydrogen atoms are substituted with fluorine atoms, specific examples of the latter fluorine-substituted lower alkyl being fluoromethyl, difluoromethyl, trifluoromethyl, 1,2-difluoroethyl, and the like.

"Optionally halogen-substituted lower alkyl" signifies lower alkyl or lower alkyl whose part or all of hydrogen atoms are substituted with halogen atoms, specific examples of the latter halogen-substituted lower alkyl being fluoromethyl, difluoromethyl, trifluoromethyl, 1,2-difluoroethyl, chloromethyl, dichloromethyl, trichloromethyl, 1,2-dichloroethyl and the like.

"Optionally fluorine-substituted lower alkyloxy" includes those groups in which lower alkyl or fluorine-substituted lower alkyl binds to oxygen, specific examples being: as lower alkyloxy, methoxy, ethoxy, n-propyloxy, isopropyloxy, n-butyloxy, isobutoxy, tert-butoxy, n-pentyloxy and the like; and as fluorine-substituted lower alkyloxy, fluoromethoxy, difluoromethoxy, trifluoromethoxy, 1,2-difluoroethoxy and the like.

"Mono-lower alkylamino" is an amino in which one of its hydrogen atoms is mono-substituted with lower alkyl, specific examples being methylamino, ethylamino, n-propylamino, isopropylamino, n-butylamino, sec-butylamino, tert-butylamino and the like.

"Di-lower alkylamino" is an amino whose two hydrogen atoms are substituted with lower alkyl groups, specific examples being dimethylamino, diethylamino, ethylmethylamino, di(n-propyl)amino, methylpropylamino, diisopropylamino and the like.

"Lower alkyloxycarbonyl" is a carbonyl to which lower alkyloxy is bound, which includes $C_1$-$C_6$ alkyloxycarbonyl, specific examples being methoxycarbonyl, ethoxycarbonyl, n-propyloxycarbonyl, isopropyloxycarbonyl, n-butyloxycarbonyl, isobutoxycarbonyl, tert-butoxycarbonyl, n-pentyloxycarbonyl, and the like.

"(Lower alkyloxycarbonyl)amino" is an amino to which lower alkyloxycarbonyl is bound, which includes $C_1$-$C_6$ alkyloxycarbonylamino, specific examples being methoxycarbonylamino, ethoxycarbonylamino, n-propyloxycarbonylamino, isopropyloxycarbonylamino, n-butoxycarbonylamino, isobutoxycarbonylamino, tert-butoxycarbonylamino, n-pentyloxycarbonylamino and the like.

"(Lower alkyloxycarbonyl)lower alkylamino" is a mono-lower alkylamino whose hydrogen on the nitrogen atom is substituted with a lower alkyloxycarbonyl. As specific examples, (methoxycarbonyl)methylamino, (ethoxycarbonyl)methylamino, (n-propyloxycarbonyl)methylamino and the like can be named.

"Lower alkylcarbonyl" is a carbonyl to which lower alkyl is bound, which includes $C_1$-$C_6$ alkylcarbonyl, specific examples being acetyl, propionyl, butyryl, isobutyryl, valeryl, isovaleryl, pivaloyl and the like.

"Lower alkylcarbonylamino" is an amino one of whose hydrogen atoms is substituted with lower alkylcarbonyl, specific examples being acetamino, propionylamino, isobutyrylamino, valerylamino, isovalerylamino, pivaloylamino and the like.

"(Lower alkylcarbonyl)lower alkylamino" is a mono-lower alkylamino in which the hydrogen on its nitrogen atom is substituted with lower alkylcarbonyl, specific examples of which including (methylcarbonyl)methylamino, (ethylcarbonyl)methylamino, (n-propylcarbonyl)methylamino and the like.

"Lower alkylcarbonyloxy" is a group in which a lower alkylcarbonyl is bound to oxygen, specific examples including acetoxy, propionyloxy, valeryloxy, isovaleryloxy, pivaloyloxy and the like.

"Mono-lower alkylcarbamoyl" is a carbamoyl one of whose hydrogen atoms is substituted with lower alkyl, specific examples including methylcarbamoyl, ethylcarbamoyl, n-propylcarbamoyl, isopropylcarbamoyl, n-butylcarbamoyl, sec-butylcarbamoyl, tert-butylcarbamoyl and the like.

"Di-lower alkylcarbamoyl" is a carbamoyl whose two hydrogen atoms are substituted with lower alkyl groups, specific examples including dimethylcarbamoyl, diethylcarbamoyl, ethylmethylcarbamoyl, di(n-propyl)carbamoyl, methylpropylcarbamoyl, diisopropylcarbamoyl and the like.

"Mono-lower alkylcarbamoylamino" is an amino one of whose hydrogen atoms is substituted with mono-lower alkylcarbamoyl group, specific examples including methylcarbamoylamino, ethylcarbamoylamino, n-propylcarbamoylamino, isopropylcarbamoylamino, n-butylcarbamoylamino, sec-butylcarbamoylamino, tert-butylcarbamoylamino and the like.

"Di-lower alkylcarbamoylamino" is an amino one of whose hydrogen atoms is substituted with di-lower alkylcarbamoyl, specific examples including dimethylcarbamoylamino, diethylcarbamoylamino, di(n-propyl)carbamoylamino, diisopropylcarbamoylamino, di(n-butyl)carbamoylamino, di(sec-butyl)carbamoylamino, di(tert-butyl)carbamoylamino, and the like.

"(Mono-lower alkylcarbamoyl)lower alkylamino" is a mono-lower alkylamino whose hydrogen on the nitrogen atom is substituted with lower alkylcarbamoyl, specific examples including (monomethylcarbamoyl)methylamino, (monoethylcarbamoyl)methylamino, [mono(n-propyl)carbamoyl]methylamino, and the like.

"(Di-lower alkylcarbamoyl)lower alkylamino" is a mono-lower alkylamino whose hydrogen on the nitrogen atom is substituted with di-lower alkylcarbamoyl, specific examples including (dimethylcarbamoyl)methylamino, (diethylcarbamoyl)methylamino, [di(n-propyl)carbamoyl]methylamino and the like.

"Mono-lower alkylcarbamoyloxy" is a group in which lower alkylcarbamoyl is bound to oxygen, specific examples including methylcarbamoyloxy, ethylcarbamoyloxy, n-propylcarbamoyloxy, isopropylcarbamoyloxy, n-butylcarbamoyloxy, sec-butylcarbamoyloxy, tert-butylcarbamoyloxy and the like.

"Di-lower alkylcarbamoyloxy" is a group in which di-lower alkylcarbamoyl is bound to oxygen, specific examples including dimethylcarbamoyloxy, diethylcarbamoyloxy, ethylmethylcarbamoyloxy, di(n-propyl)carbamoyloxy, methylpropylcarbamoyloxy, diisopropylcarbamoyloxy and the like.

"Lower alkylsulfonyl" is a group in which lower alkyl is bound to sulfonyl, specific examples including methylsulfonyl, ethylsulfonyl, n-propylsulfonyl, isopropylsulfonyl, n-butylsulfonyl, sec-butylsulfonyl, tert-butylsulfonyl and the like.

"Lower alkylsulfonylamino" is an amino one of whose hydrogen atoms is substituted with lower alkylsulfonyl, specific examples including methylsulfonylamino, ethylsulfonylamino, n-propylsulfonylamino, isopropylsulfonylamino, n-butylsulfonylamino, sec-butylsulfonylamino, tert-butylsulfonylamino and the like.

"Mono-lower alkylsulfamoyl" is a sulfamoyl one of whose hydrogen atoms is substituted with lower alkyl, specific examples including monomethylsulfamoyl, monoethylsulfamoyl, mono(n-propyl)sulfamoyl, monoisopropylsulfamoyl, mono(n-butyl)sulfamoyl, mono(sec-butyl)sulfamoyl, mono(tert-butyl)sulfamoyl and the like.

"Di-lower alkylsulfamoyl" is a sulfamoyl whose two hydrogen atoms are substituted with lower alkyl groups, specific examples including dimethylsulfamoyl, diethylsulfamoyl, di(n-propyl)sulfamoyl, diisopropylsulfamoyl, di(n-butyl)sulfamoyl, di(sec-butyl)sulfamoyl, di(tert-butyl)sulfamoyl and the like.

"(Lower alkylsulfamoyl)amino" is an amino one of whose hydrogen atoms is substituted with a lower alkylsulfamoyl, specific examples including (monomethylsulfamoyl)amino, (monoethylsulfamoyl)amino, [mono(n-propyl)sulfamoyl]amino, (monoisopropylsulfamoyl)amino, [mono(n-butyl)sulfamoyl]amino, [mono(sec-butyl)sulfamoyl]amino, (tert-butylsulfamoyl)amino and the like.

"(Di-lower alkylsulfamoyl)amino" is an amino one of whose hydrogen atoms is substituted with di-lower alkylsulfamoyl, specific examples including (dimethylsulfamoyl)amino, (diethylsulfamoyl)amino, (ethylmethylsulfamoyl)amino, [di(n-propyl)sulfamoyl]amino, (methylpropylsulfamoyl)amino, (diisopropylsulfamoyl)amino and the like.

"(Mono-lower alkylsulfamoyl)lower alkylamino" is a "lower alkylamino" whose hydrogen on the nitrogen atom is substituted with mono-lower alkylsulfamoyl, specific examples including (monomethylsulfamoyl)methylamino, (monoethylsulfamoyl)methylamino, [mono(n-propyl)sulfamoyl]methylamino and the like.

"(Di-lower alkylsulfamoyl)lower alkylamino" is a "lower alkylamino" whose hydrogen on the nitrogen atom is substituted with di-lower alkylsulfamoyl, specific examples including (dimethylsulfamoyl)methylamino, (diethylsulfamoyl)methylamino, [di(n-propyl)sulfamoyl]methylamino and the like.

Where $R^1$ and Z together form, with the carbon atom to which they bind, a "3 to 6-membered aliphatic heterocyclic group", examples of the aliphatic carbocycle include cyclopropane ring, cyclobutane ring, cyclopentane ring, cyclohexane ring and the like.

Where $R^1$ and Z together form, with the carbon atom to which they bind, a "3 to 6-membered aliphatic heterocyclic group", examples of the aliphatic heterocycle include aziridine ring, oxolan ring, pyrrolidine ring, piperidine ring, tetrahydropyran ring, tetrahydrofuran ring, dioxane ring, morpholine ring and the like.

As examples of aliphatic carbocycle of the "3 to 10-membered aliphatic carbocyclic group" represented by CY, cyclopropane ring, cyclobutane ring, cyclopentane ring, cyclohexane ring, cyclopentane ring, cyclohexene ring, cycloheptane ring, cyclooctane ring, cyclononane ring, cyclodecane ring and the like can be named.

As examples of aliphatic heterocycle of the "3 to 10-membered aliphatic heterocyclic group" represented by CY, aziridine ring, oxolan ring, azetidine ring, pyrrolidine ring, piperidine ring, tetrahydrofuran ring, tetrohydropyran ring, 1,4-dioxane ring, morpholine ring, dihydropyridine ring and the like can be named.

As an example of aromatic carbocycle of the "5- or 6-membered aromatic carbocyclic group" represented by CY, benzene ring may be named.

As examples of aromatic heterocycle of the "5- or 6-membered aromatic heterocyclic group" represented by CY, pyran ring, pyrrole ring, thiophene ring, pyrazole ring, imidazole ring, triazole ring, tetrazole ring, oxazole ring, oxadiazole ring, thiazole ring, pyridine ring, pyrazine ring, pyrimidine ring, pyridazine ring and the like can be named.

As examples of aromatic carbocycle of the "mono-or bi-cyclic aromatic carbocyclic group" represented by Ar, benzene ring and naphthalene ring can be named.

As examples of aromatic heterocycle of the "mono- or bi-cyclic aromatic heterocyclic group" represented by Ar, pyran ring, pyrrole ring, thiophene ring, pyrazole ring, imidazole ring, oxazole ring, isoxazole ring, thiazole ring, isothiazole ring, oxadiazole ring, thiadiazole ring, triazole ring, tetrazole ring, pyridine ring, pyrazine ring, pyrimidine ring, pyridazine ring, indoline ring, benzofuran ring, benzothiophene ring, benzimidazole ring, benzoxazole ring, benzisoxazole ring, benzothiazole ring, benzisothiazole ring, indazole ring, purine ring, quinoline ring, isoquinoline ring, phthalazine ring, naphthyridine ring, quinoxaline ring, quinazoline ring, cinnoline ring, pteridine ring and the like can be named.

As the substituent groups selected from Group α, the following can be named: [Group α] halogen, hydroxyl, amino, nitro, oxo, mono-lower alkylamino, di-lower alkylamino, optionally halogen-substituted lower alkyl, optionally fluorine-substituted lower alkyloxy, lower cycloalkyloxy, lower alkyloxycarbonyl, (lower alkyloxycarbonyl) amino, (lower alkyloxycarbonyl)lower alkylamino, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl)lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsufamoyl) lower alkylamino and (di-lower alkylsufamoyl)lower alkylamino.

Also as the substituent groups selected from Group P, the following can be named:

[Group β]

nitro, aryloxy, lower cycloalkyl, lower cycloalkyloxy, lower alkylenedioxy, halogen, hydroxyl, optionally hydroxyl- or fluorine-substituted lower alkyl and optionally fluorine-substituted lower alkyloxy.

"Pharmaceutically acceptable salts" of the compounds which are represented by the general formula [I] signify those customarily used salts which are permissible to be used in drug, specific examples including acid addition salts at amino or acid addition salts at nitrogen-containing heterocycle.

As such acid addition salts, inorganic acid salts such as hydrochloride, sulfate, nitrate, phosphate, perchlorate and the like; organic acid salts such as maleate, fumarate, tartarate, citrate, ascorbate, trifluoroacetate and the like; and sulfonic acid salts such as methanesulfonate, isethionate, benzenesulfonate, p-toluenesulfonate and the like can be named.

Compounds Represented by the General Formula [I]

In the compounds represented by the general formula [I], $R^1$ may be, for example,
1) hydrogen atom,
2) hydroxyl group,
3) optionally halogen-substituted lower alkyl group,
4) aliphatic carbocyclic group in which $R^1$ and Z together form, with the carbon atom to which they bind, a 3 to 6-membered aliphatic carbocycle optionally having a substituent selected from Group α, or
5) aliphatic heterocyclic group in which $R^1$ and Z together form, with the carbon atom to which they bind, a 3 to 6-membered aliphatic heterocycle optionally having a substituent selected from Group α.

As examples of optionally halogen-substituted lower alkyl, methyl, ethyl, n-propyl, isopropyl, n-butyl, isobutyl, chloromethyl, fluoromethyl, dichloroethyl, difluoroethyl, trifluoromethyl, trifluoroethyl and the like can be named.

Those cases in which $R^1$ and Z together form, with the carbon atom to which they bind, a 3 to 6-membered aliphatic carbocycle or aliphatic heterocycle will be explained later.

Preferred $R^1$ includes hydrogen, hydroxyl and methyl.

$R^2$, $R^{3a}$, $R^{3b}$, $R^{5a}$ and $R^{5b}$ stand for hydrogen or optionally halogen-substituted lower alkyl, independently of each other.

Preferred $R^2$ includes hydrogen, methyl, ethyl, n-propyl and isopropyl.

Preferred $R^{3a}$ and $R^{3b}$ include hydrogen.

Preferred $R^{5a}$ and $R^{5b}$ include hydrogen and methyl.

$R^{4a}$ and $R^{4b}$ stand for hydrogen, halogen, hydroxyl or optionally halogen-substituted lower alkyl, independently of each other.

As specific examples of $R^{4a}$ or $R^{4b}$, hydrogen, fluorine, chlorine, hydroxyl, methyl, ethyl, n-propyl, isopropyl, n-butyl, isobutyl, fluoromethyl, chloromethyl, dichloromethyl, trifluoromethyl and the like can be named, preferred examples including hydrogen, fluorine and hydroxyl. Particularly favorable combinations are:
  both are hydrogen atoms;
  one is hydrogen and the other is fluorine; or
  one is hydrogen and the other is hydroxyl.

$R^6$ stands for halogen or optionally halogen-substituted lower alkyl, and n stands for an integer of 1-8.

As specific examples of $R^6$, hydrogen, fluorine, chlorine, hydroxyl, methyl, ethyl, n-propyl, isopropyl, n-butyl, isobutyl, fluoromethyl, chloromethyl, dichloromethyl, trifluoromethyl and the like can be named, preferred examples including hydrogen, fluorine and methyl. In particular, hydrogen is recommended.

$W^1$ and $W^2$ each stands for hydrogen, or they together form —O—CH$_2$—, —CH$_2$—CH$_2$—, or —CH$_2$—O—.

Preferred combinations of $W^1$ and $W^2$ include:
both $W^1$ and $W^2$ are hydrogen atoms;
$W^1$ and $W^2$ together form —O—CH$_2$—;
$W^1$ and $W^2$ together form —CH$_2$—CH$_2$—; and
$W^1$ and $W^2$ together form —CH$_2$—O—.

Z stands for:
1) lower alkyl,
2) CY,
3) an aliphatic carbocyclic group in which $R^1$ and Z together form, with the carbon atom to which they bind, a 3 to 6-membered aliphatic carbocycle which may have substituent(s) selected from Group α, or
4) an aliphatic heterocyclic group in which $R^1$ and Z together form, with the carbon atom to which they bind, a 3 to 6-membered aliphatic heterocycle which may have substituent(s) selected from Group α.

In particular, CY is recommended as Z.

Examples of lower alkyl in Z include methyl, ethyl, n-propyl, isopropyl, n-butyl and isobutyl.

CY stands for a cyclic group which may have one, two or more substituents selected from Group α, and it is selected from the group consisting of
1) 3 to 10-membered aliphatic carbocyclic groups,
2) 3 to 10-membered aliphatic heterocyclic groups,
3) 5 or 6-membered aromatic carbocyclic groups,
4) 5 or 6-membered aromatic heterocyclic groups.

As rings in the cyclic groups represented by CY, for example, cyclopentane ring, cyclohexane ring, cyclopentene ring, cyclohexene ring, pyrrolidine ring, morpholine ring, piperazine ring, piperidine ring, benzene ring, pyridine ring, pyrazine ring, pyrimidine ring, pyrrole ring, pyrazole ring, imidazole ring, triazole ring, oxazole ring, imidazole ring, triazole ring, oxazole ring, oxadiazole ring, thiazole ring, tetrazole ring, dihydropyridine ring and the like can be named. Preferably, cyclopentane ring, cyclohexane ring, prrolidine ring, morpholine ring, piperazine ring, pyperidine ring, benzene ring, dihydropyridine ring, pyridine ring, pyrazine ring, pyrimidine ring, pyrrole ring, pyrazole ring, imidazole ring, triazole ring, tetrazole ring, oxazole ring, oxadiazole ring, oxazolidine ring and thiazole ring.

In CY, as specific examples of the substituents selected from Group α, fluorine, chlorine, oxo, methyl, ethyl, isopropyl, fluoromethyl, trifluoromethyl, methoxy, ethoxy, cyclopropyloxy, trifluoromethoxy, isopropyloxycarbonyl, t-butyloxycarbonyl, methanesulfonyl, acetamino, propionylamino and the like can be named. Of those, as preferred examples fluorine, chorine, oxo, methyl, ethyl, trifluoromethyl, methoxy, methanesulfonyl, acetamino and propionylamino are recommended.

As specific examples of CY, phenyl, 4-fluorophenyl, 4-chlorophenyl, 3,4-difluorophenyl, 4-methoxyphenyl, 4-tolyl, 4-ethylphenyl, 4-isopropylphenyl, 4-fluoromethylphenyl, 4-trifluoromethylphenyl, pyridinyl, 2-fluoropyridinyl, pyridin-3-yl, pyrazinyl, pyrimidinyl, 2-fluoropyridin-4-yl, 6-fluoropyridin-3-yl, 6-trifluoromethylpyridin-3-yl, 6-methoxypyridin-3-yl, pyrazinyl, pyrrol-1-yl, pyrazolyl, imidazolyl, imidazol-1-yl, 2-methylimidazol-1-yl, 1,2,3,-triazol-1-yl, 4-methyl-1,2,3-triazol-1-yl, 1,2,4-triazol-1-yl, 1,2,3,4-tetrazol-1-yl, 2,3,4-tetrazol-2-yl, oxazolyl, oxadiazolyl, thiazolyl, pyrrolidin-1-yl, piperidinyl, morpholinyl, dihydropyridinyl, 4-(t-butyloxycarbonyl)piperazinyl, 2-pyperidon-1-yl, 2-pyridon-1-yl, 2-pyrrolidon-1-yl, oxazolidin-2-on-1-yl, 4-methanesulfonyl-piperazin-2-on-1-yl, cyclopentyl, 3-methylcyclopentyl, cyclohexyl, 4-methylcyclohexyl and the like can be named.

Preferably, phenyl, 4-fluorophenyl, 4-chlorophenyl, 3,4-difluorophenyl, 4-methoxyphenyl, 4-tolyl, 4-trifluoromethylphenyl, pyridinyl, pyridin-3-yl, pyrazinyl, pyrimidinyl, 6-fluoropyridin-3-yl, 2-fluoropyridin-4-yl, 6-trifuluoromethylpyridin-3-yl, 6-methoxypyridin-3-yl, pyrrol-1-yl, pyrazolyl, imidazolyl, 2-methylimidazolyl, 4-methylimidazolyl, 1,2,3-triazol-1-yl, 4-methyl-1,2,3-triazol-1-yl, 1,2,4-triazol-1-yl, 1,2,3,4-tetrazol-1-yl, 2,3,4-tetrazol-2-yl, oxazolyl, oxadiazolyl, thiazolyl, pyrrolidin-1-yl, piperidinyl, morpholinyl, dihydropyridinyl, 2-piperidon-1-yl, 2-pyridon-1-yl, 2-pyrrolidon-1-yl, oxazolidin-2-on-1-yl, 4-methanesulfonyl-piperazin-2-on-1-yl, cyclopentyl and cyclohexyl are recommendable.

As the 3 to 6-membered aliphatic carbocycles which Z and $R^1$ form together with the carbon atom to which they bind, specific examples include cyclopropyl, cyclobutyl, cyclopentyl, cyclohexyl and the like.

As the 3 to 6-membered aliphatic heterocycles which Z and $R^1$ together form with the carbon atom to which they bind, aziridin-2-yl, pyrrolidin-3-yl, pyperidin-4-yl, I-(t-butyloxycarbonyl)-piperidinyl, tetrahydrofuran-3-yl, tetrahydropyran-4-yl and the like can be named.

$Y^1$, $Y^2$, $Y^3$ and $Y^4$, each independently of each other, stand for methylene which optionally has substituent(s) selected from Group α, or nitrogen atom, with the proviso that not all of $Y^1$ through $Y^4$ are simultaneously nitrogen atoms.

As the substituent selected from Group α which the methylene may have, for example, fluorine, chlorine, methoxy, acetamino, propionylamino and the like can be named.

Preferred specific examples of $Y^1$, $Y^2$, $Y^3$ and $Y^4$ are, independently of each other, —CH—, —CF, —C(NHCOCH$_3$)—, —C(NHCOC$_2$H$_5$)— or —N—.

Preferred combinations of $Y^1$, $Y^2$, $Y^3$, and $Y^4$ are the following.

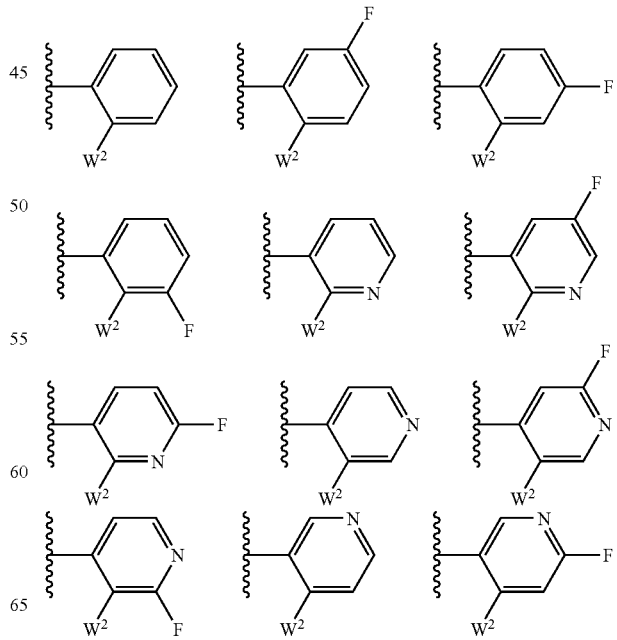

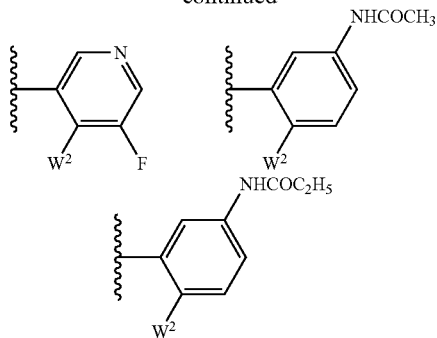

Of those, preferably the following are recommended.

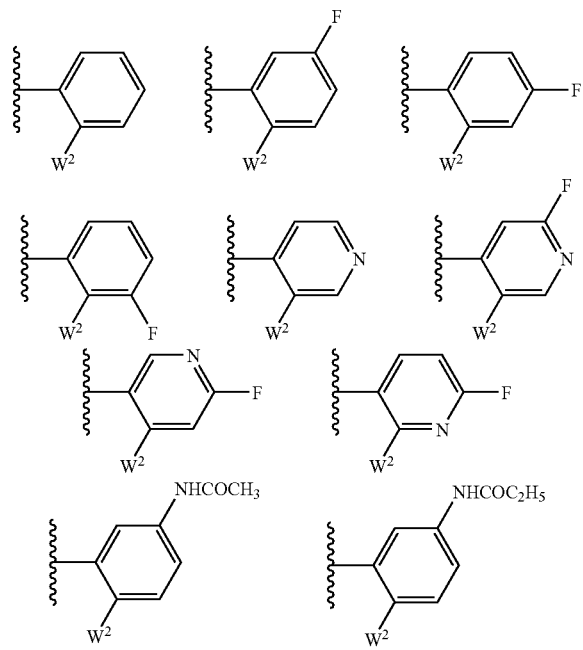

Ar stands for mono- or bi-cyclic aromatic carbocyclic group or aromatic heterocyclic group, which may have one, two or more substituents selected from Group β.

As preferred examples of the aromatic carbocycle or aromatic heterocycle of Ar, benzene ring, pyridine ring, pyrazine ring, pyrimidine ring, pyridazine ring, pyrrole ring, pyrazole ring, imidazole ring, thiazole ring, triazole ring and the like can be named. In particular, benzene ring, pyridine ring, pyrazine ring and pyrimidine ring are recommendable.

Preferred substituents on Ar which are selected form Group β include fluoro, chloro, methyl, ethyl, n-propyl, iso-propyl, fluoromethyl, trifluoromethyl, methoxy, ethoxy, cyclopropyloxy and trifluoromethoxy and the like. In particular, fluoro, choloro, methyl, ethyl, methoxy and trifluoromethyl are recommendable.

As specific examples of Ar, phenyl, 4-fluorophenyl, 3,4-difluorophenyl, 4-chlorophenyl, 3,4-dichlorophenyl, 4-tolyl, 4-ethylphenyl, 4-fluoromethylphenyl, 4-trifluoromethylphenyl, 4-methoxyphenyl, 4-trifluoromethoxyphenyl, pyridinyl, 3-pyridinyl, 6-fluoropyridin-3-yl, 6-fluoropyridin-4-yl, 6-methyoxypyridin-3-yl, 6-trifluoromethylpyridin-3-yl, imidazol-1-yl, 2-methylimidazol-1-yl, 4-methylimidazol-1-yl, thiazol-2-yl, 1,2,3-triazol-1-yl, 1,2,4-triazol-1-yl, pyrazinyl, pyrimidinyl and the like can be named.

As preferred examples of Ar, phenyl, 4-fluorophenyl, 3,4-difluorophenyl, 4-chlorophenyl, 4-methoxyphenyl, 4-tolyl, 4-trifluoromethylphenyl, pyridinyl, 6-fluoropyridin-3-yl, 6-methoxypyridin-3-yl, 6-trifluoromethylpyridin-3-yl, pyrazinyl, pyrimidinyl and the like are recommendable.

Of the compounds represented by the general formula [I], particularly those represented by the following general formula [I-1]:

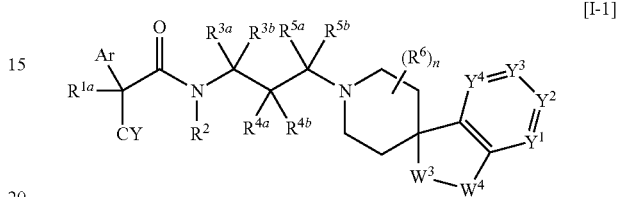

[in which $R^{1a}$ stands for hydrogen, hydroxyl, or optionally halogen-substituted lower alkyl,
$W^3$ stands for —O— or —CH$_2$—,
$W^4$ stands for —CH$_2$— or —O—, with the proviso that $W^3$ and $W^4$ are not —O— at the same time, and
$R^2$, $R^{3a}$, $R^{3b}$, $R^{4a}$, $R^{4b}$, $R^{5a}$, $R^6$, $Y^1$, $Y^2$, $Y^3$, $Y^4$, CY, Ar and n have the same significations as above]; and those represented by the general formula [I-2]:

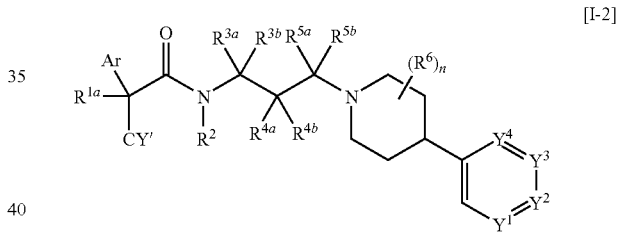

[in which CY' stands for a substituent selected from the group consisting of pyrrolyl, imidazolyl, lower alkylimidazolyl, 4-nitroimidazolyl, triazolyl, lower alkyltriazolyl, tetrazolyl, pyridonyl, 2-oxo-1-piperidinyl, 2-oxo-1-piperazinyl, 4-lower alkyl-2-oxo-1-piperazinyl, 4-lower alkylsulfonyl-2-oxo-1-piperazinyl and 4-lower alkylcarbonyl-2-oxo-1-piperazinyl, and
$R^{1a}$, $R^2$, $R^{3a}$, $R^{3b}$, $R^{4a}$, $R^{4b}$, $R^{5a}$, $R^{5b}$, $R^6$, $Y^1$, $Y^2$, $Y^3$, $Y^4$, Ar and n have the same significations as above];

are novel substances and are especially recommendable compounds.

Of those compounds represented by the general formula [I-1], the following are preferred:

(1a) compounds of the general formula [I-1] in which $R^{1a}$ is hydrogen, methyl or hydroxyl;

(2a) compounds of above (1a), in which $R^2$ is hydrogen, methyl, ethyl, n-propyl or isopropyl;

(3a) compounds of above (1a) or (2a), in which $R^{3a}$ and $R^{3b}$ are hydrogen atoms;

(4a) compound of (1a)-(3a), in which $R^{4a}$ or $R^{4b}$ is selected from the group consisting of hydrogen, fluorine and hydroxyl;

(5a) compounds of (1a)-(4a), in which $R^{5a}$ or $R^{5b}$ is hydrogen or methyl;

(6a) compounds of (1a)-(5a), in which $R^6$ are hydrogen atoms;

(7a) compounds of (1a)-(6a), in which $Y^1, Y^2, Y^3$ and $Y^4$ are selected from the group consisting of —CH—, —CF—, —C(NHCOCH$_3$)—, —C(NHCOC$_2$H$_5$)— and —N—;

(8a) compounds of (1a)-(7a), in which the ring in the cyclic group represented by CY is selected from the group consisting of cyclopentane ring, cyclohexane ring, pyrrolidine ring, morpholine ring, piperazine ring, piperidine ring, benzene ring, dihydropyridine ring, pyridine ring, pyrazine ring, pyrimidine ring, pyrrole ring, pyrazole ring, imidazole ring, triazole ring, oxazole ring, oxadiazole ring, tetrazole ring, oxazolidine ring and thiazole ring;

(9a) compounds of (1a)-(8a), in which CY is a substituent selected from the group consisting of phenyl, 4-fluorophenyl, 4-chlorophenyl, 3,4-difluorophenyl, 4-methoxyphenyl, 4-tolyl, 4-trifluoromethylphenyl, pyridinyl, pyridin-3-yl, pyrazinyl, pyrimidinyl, 6-fluoropyridin-3-yl, 2-fluoropyridin-4-yl, 6-trifluoromethylpyridin-3-yl, 6-methoxypyridin-3-yl, pyrrol-1-yl, pyrazolyl, imidazolyl, 2-methylimidazolyl, 4-methylimidazolyl, 1,2,3-triazol-1-yl, 4-methyl-1,2,3-triazol-1-yl, 1,2,4-triazol-1-yl, 1,2,3,4-tetrazol-1-yl, 2,3,4-tetrazol-2-yl, thiazolyl, pyrrolidin-1-yl, piperidinyl, 2-piperidon-1-yl, 2-pyridon-1-yl, 2-pyrrolidon-1-yl, oxazolidin-2-on-1-yl, 4-methanesulfonyl-piperazin-2-on-1-yl, cyclopentyl and cyclohexyl;

(10a) compounds of (1a)-(9a), in which the aromatic ring in the mono-or by-cyclic aromatic carbocyclic group or aromatic heterocyclic group which are represented by Ar is selected from the group consisting of benzene ring, pyridine ring, pyrazine ring and pyrimidine ring;

(11a) compounds of (1a)-(10a), in which Ar is a substituent selected from the group consisting of phenyl, 4-fluorophenyl, 3,4-difluorophenyl, 4-chlorophenyl, 4-methoxyphenyl, 4-tolyl, 4-trifluoromethylphenyl, pyridinyl, 6-fluoropyridin-3-yl, 6-trifluoromethylpyridin-3-yl and 6-methoxypyridin-3-yl;

(12a) compounds of (1a)-(11a), in which $W^3$ is —O— and $W^4$ is —CH2-; and (13a) compounds of (1a)-(11a), in which $W^3$ is —CH2- and $W^4$ is —O—.

Of the compounds represented by the general formula [I-1], the following are particularly recommendable:

2-(3,4-difluorophenyl)-2-(2-oxo-1-pyrrolidinyl)-N-[3-(spiro [5-fluoroisobenzofuran-1(3H), 4'-piperidin]-1-yl)propyl] acetamide, 2-(3,4-difluorophenyl)-N-methyl-2-(1H-1,2,3-triazol-1-yl)-N-[3-(spiro[isobenzofuran-1(3H), 4'-piperidin]-1-yl)propyl]acetamide, 2-(3,4-difluorophenyl)-N-methyl-2-(2H-1,2,3,4-tetrazol-2-yl)-N-[3-(spiro[isobenzofuran-1(3H), 4'-piperidin]-1-yl) propyl]acetamide, 2-(3,4-difluorophenyl)-N-methyl-2-(2-oxo-1(2H)pyridinyl)-N-[3-(spiro[isobenzofuran-1(3H), 4'-piperidin]-1-yl) propyl]acetamide, 2-(3,4-difluorophenyl)-N-methyl-2-(2-oxo-1-pyrrolidinyl)-N-[3-(spiro[5-fluoroisobenzofuran-1(3H), 4'-piperidin]-1-yl)propyl]-acetamide, 2-(3,4-difluorophenyl)-N-methyl-2-(2-methyl-1H-imidazol-1-yl)-N-[3-(spiro[6-fluoroisobenzofuran-1(3H), 4'-piperidin]-1-yl)propyl]-acetamide, 2-(3,4-difluorophenyl)-N-methyl-2-(2-methyl-1H-imidazole-1-yl)-N-[3-(spiro[5-fluoro-6-azaisobenzofuran-1 (3H), 4'-piperidin]-1-yl)propyl]acetamide, 2-(3,4-difluorophenyl)-2,2-dimethyl-N-methyl-N-[3-(spiro [5-fluoro-6-azaisobenzofuran-1(3H), 4'-piperidin]-1-yl) propyl]-acetamide, 2,2-bis(6-fluoro-3-pyridinyl)-N-methyl-N-[3-(spiro[5-fluoro-6-azaisobenzofuran-1(3H), 4'-piperidin]-1-yl)propyl]-acetamide, 2,2-bis(4-fluorophenyl)-N-methyl-N-[3-(spiro[5-fluoro-6-azaisobenzofuran-1(3H), 4'-piperidin]-1-yl)propyl]-acetamide, 2-(3,4-difluorophenyl)-N-methyl-2-(1H-pyrrol-1-yl)-N-[3-(spiro[5-fluoro-6-azaisobenzofuran-1(3H), 4'-piperidin]-1-yl)propyl]-acetamide, 2-(4-fluorophenyl)-N-methyl-2-(1H-pyrrol-1-yl)-N-[3-(spiro [5-fluoro-6-azaisobenzofuran-1(3H), 4'-piperidin]-1-yl)propyl]-acetamide, 2-(3,4-difluorophenyl)-N-methyl-2-(1H-pyrazol-1-yl)-N-[3-(spiro[5-fluoro-6-azaisobenzofuran-1(3H), 4'-piperidin]-1-yl)propyl]acetamide, 2-(3,4-difluorophenyl)-N-methyl-2-(1H-pyrrol-1-yl)-N-[3-(spiro[6-fluoro-5-azaisobenzofuran-1(3H), 4'-piperidin]-1-yl)propyl]acetamide, 2-(3,4-difluorophenyl)-N-ethyl-2-(2-oxo-1-pyrrolidinyl)-N-[3-(spiro[isobenzofuran-1(3H), 4'-piperidin]-1-yl)propyl] acetamide, 2-(3,4-difluorophenyl)-N-ethyl-2-(4-methanesulfonyl)-2-oxo-1-piperazinyl)-N-[3-(spiro[6-fluoroisobenzofuran-1 (3H), 4'-piperidin]-1-yl)propyl]acetamide, or 2,2-bis(4-fluorophenyl)-2-hydroxy-N-methyl-N-[3-(spiro [5-fluoro-6-azaisobenzofuran-1(3H), 4'-piperidin]-1-yl) propyl]acetamide, Among the compounds represented by the general formula [I-2], those preferred are:

(1b) compounds of the general formula [I-2], in which $R^{1a}$ is hydrogen, methyl or hydroxyl;

(2b) compounds of above (1b), in which $R^2$ is hydrogen, methyl, ethyl, n-propyl or isopropyl;

(3b) compounds of above (1b) or (2b), in which both $R^{3a}$ and $R^{3b}$ are hydrogen atoms;

(4b) compounds (1b)-(3b), in which $R^{4a}$ or $R^{4b}$ is selected from the group consisting of hydrogen, fluorine and hydroxyl;

(5b) compounds of (1b)-(4b), in which $R^{5a}$ or $R^{5b}$ is hydrogen or methyl;

(6b) compounds (1b)-(5b), in which all $R^6$ are hydrogen stoms, (7b) compounds (1b)-(6b), in which $Y^1, Y^2, Y^3$ and $Y^4$ are selected from the group consisting of —CH—, —CF—, C(NHCOCH$_3$), —C(NHCOC$_2$H$_5$)— and —N—;

(8b) compounds of (1b)-(7b), in which CY' group is selected from the group consisting of pyrrolyl, imidazolyl, lower alkylimidazolyl, 4-nitroimidazolyl, triazolyl, lower alkyltriazolyl, tetrazolyl, pyridonyl, 2-oxo-1-piperidinyl, 2-oxo-1-piperazinyl, 4-lower alkyl-2-oxo-1-piperazinyl, 4-lower alkylsulfonyl-2-oxo-1-piperazinyl and 4-lower alkylcarbonyl-2-oxo-1-piperazinyl;

(9b) compounds of (1b)-(7b), in which CY' group is selected from the group consisting of imidazolyl, lower alkylimidazolyl, triazolyl, lower alkyltriazolyl, trtrazolyl, 2-oxo-1-piperidinyl, 2-oxo-1-piperazinyl, 4-lower alkyl-2-oxo-1-piperazinyl, 4-lower alkylsulfonyl-2-oxo-1-piperazinyl and 4-lower alkylcarbonyl-2-oxo-1-piperazinyl;

(10b) compounds of (1b)-(9b), in which the aromatic ring in the mono-or by-cyclic aromatic carbocyclic group or aromatic heterocyclic group which are represented by Ar is selected from the group consisting of benzene ring, pyridine ring, pyrazine ring and pyrimidine ring; and (11b) compounds of (1b)-(10b), in which Ar is a substituent selected from the group consisting of phenyl, 4-fluorophenyl, 3,4-difluorophenyl, 4-chlorophenyl, 4-methoxyphenyl, 4-tolyl, 4-trifluoromethylphenyl, pyridinyl, 6-fluoropyridin-3-yl, 6-trifluoromethylpyridin-3-yl and 6-methoxypyridin-3-yl.

Production Processes of Compounds Represented by the General Formula [I]

Compounds which are represented by the general formula [I] can be produced by, for example, suitably combining the following production processes.

Production Process 1

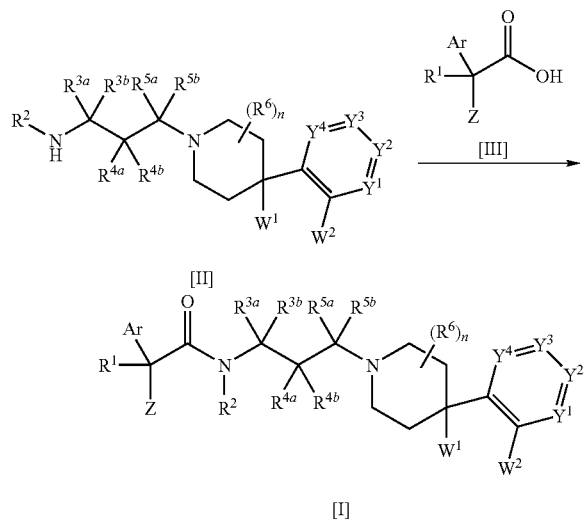

Reaction Scheme 1

[in the formulae, $R^1$, $R^2$, $R^{3a}$, $R^{3b}$, $R^{4a}$, $R^{4b}$, $R^{5a}$, $R^{5b}$, $R^6$, $Y^1$, $Y^2$, $Y^3$, $Y^4$, Ar, $W^1$, $W^2$, Z and n have the earlier given significations].

Production process 1 produces a compound of the general formula [I] by amidating a compound of the general formula [II] and a compound of the general formula [III].

The amidation can be conducted by per se known methods, for example, one comprising reacting a compound represented by the general formula [II] with a compound represented by the general formula [III] in the presence of a condensing agent, or one comprising activating carboxylic acid moiety of a compound represented by the general formula [III] by a conventionally known means to convert it to a reactive derivative and then amidating said derivative with a compound represented by a general formula [II] (cf. "Fundamentals and Experiments of Peptide Synthesis", Nobuo IZUMIYA, et al., Maruzen Publishing Co., 1983, for both of these methods).

1) Method of Amidation in the Presence of a Condensing Agent

A compound represented by the general formula [II] is amidated with a compound of the general formula [III] in the optional presence, preferably in the presence of, for example, N-hydroxybenzotriazole (HoBt), using a condensing agent such as 1,3-dicyclohexylcarbodiimide, 1-ethyl-3-(3-dimethylaminopropyl)-carbodiimide hydrochloride (EDCI) and the like, to provide a compound represented by the general formula [I].

The use ratio of the compound of the general formula [II] and that of the general formula [III] is, for example, in the range of 0.9-2.0 moles, preferably 1.0-1.5 moles of the compound represented by the general formula [III] per mole of the compound represented by the general formula [II].

Also as exemplary use rate of the condensing agent, 1.0-2.0 moles, preferably 1.0-1.5 moles, per mole of the compound represented by the general formula [III] is recommended.

When N-hydroxybenzotriazole is used, its exemplary use rate can range 0.9-2.0 moles, preferably 1.0-1.2 moles, per mole of the compound represented by the general formula [II].

Furthermore, dimethylaminopyridine may be added to the reaction system for accelerating the reaction, at a use rate of, for example, 0.1-1.0 mole, preferably 0.1-0.5 mole, per mole of the compound represented by the general formula [II].

The amidation reaction may be conducted in an organic solvent, examples of suitable solvent including ether solvents shch as 1,4-dioxane ("dioxane"), tetrahydrofuran ("THF"), diethyl ether ("ether") and the like; aromatic hydrocarbons such as benzene, toluene, xylene, chlorobenzene and the like; halogenated hydrocarbons such as dichloroethane, chloroform, dichloromethane, carbon tetrachloride and the like; pyridine, ethyl acetate, N,N-dimethylformamide ("DMF"), dimethylsulfoxide ("DMSO") and the like.

The reaction temperature may range, for example, 0-80° C., preferably 20-50° C., and the reaction time, 1-48 hours.

2) Method of Amidation Via Reactive Derivative Form

An object compound is obtained by converting a compound (carboxylic acid) represented by the general formula [III] to a "reactive derivative" by such methods as:

a) conversion to an acid chloride with a chlorinating agent such as thionyl chloride, oxalyl chloride, phosphorus oxychloride or the like (acid chloride method), b) conversion to a mixed acid anhydride using isobutyl chloroformate, methyl chloroformate or the like (mixed acid anhydride method), or c) conversion to active esters such as p-nitrophenyl ester, N-hydroxysuccinimide ester or the like (active ester method)

and thereafter subjecting the resulting reactive derivative, either as isolated or without isolation, to an amidation reaction with a compound (amine) represented by the general formula [II]. Preparation of such reactive derivatives, furthermore, can be conducted following those methods described in, for example, "Fundamentals and Experiments of Peptide Synthesis" (Nobuo IZUMIYA, et al, Maruzen Publishing Co., 1983).

As the use rate of the "reactive derivative" in the amidation, for example, a range of 0.8-3.0 moles, preferably 1.1-1.3 moles, per mole of the compound represented by the general formula [II] is recommended.

This reaction can be accelerated by conducting it in the presence of a basic catalyst. As examples of useful basic catalyst, alkali metal carbonates such as lithium carbonate, sodium carbonate, potassium carbonate and the like; alkali metal hydrogencarbonates such as sodium hydrogencarbonate, potassium hydrogencarbonate and the like; and organic bases such as triethylamine, diisopropylethylamine, tri-n-butylamine, 1,5-diazabicyclo[4.3.0]-5-nonene, 1,8-diazabicyclo[5.4.0]-7-undecene, pyridine, N,N-dimethylaminopyridine and the like can be named.

As use rate of the basic catalyst, for example, 0.1-2.0 moles, preferably 01.-1.2 moles, per mole of the "reactive derivative" is recommended.

As the reaction solvent, those named in the above can be used, and as the reaction temperature, for example, −50-80° C., preferably 0-30° C. are recommended. Exemplary reaction time ranges about 30 minutes-24 hours, while preferably 30 minutes-15 hours is recommended.

Also in the amidation reaction using the reactive derivative, dimethylaminopyridine may be used for accelerating the reaction.

Upon extracting and purifying the solution mixture containing a compound represented by the general formula [I] as obtained according to any of the above methods, the compound of the general formula can be isolated.

Production Processes of the Compounds Represented by the General Formula [II]

Compounds which are represented by the general formula [II] can be prepared by the following processes.

Reaction Scheme 2

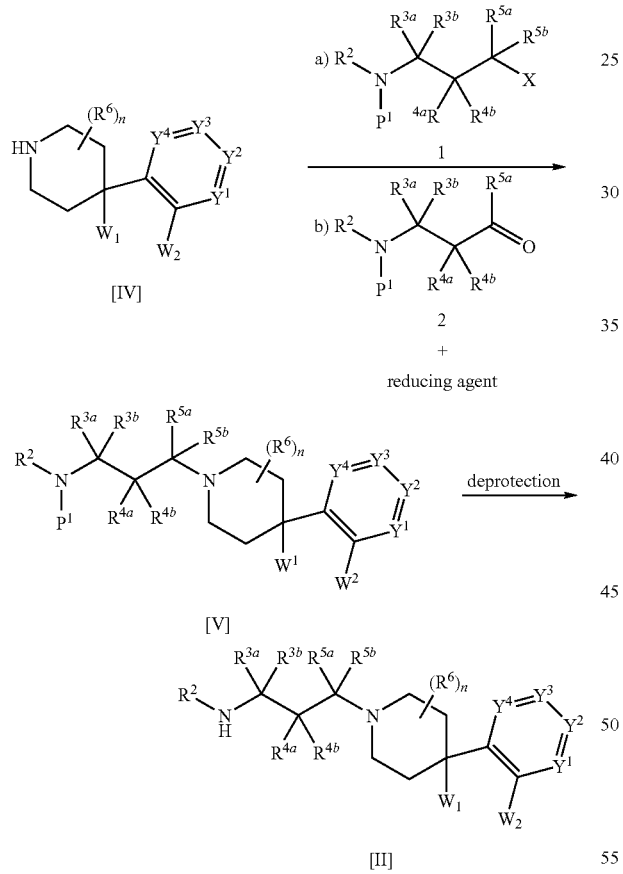

[V]

[II]

(in which $P^1$ stands for a protective group such as t-butyloxycarbonyl, benzyloxycarbonyl, 9-fluorenyl methoxy carbonyl and the like and when R═H as $P^1$, an imide-type protective group, e.g., phthalimide, may be named; X stands for a halogen atom such as chlorine, bromine, iodine and the like; and $R^2$, $R^{3a}$, $R^{3b}$, $R^{4a}$, $R^{4b}$, $R^{5a}$, $R^{5b}$, $R^6$, $Y^1$, $Y^2$, $Y^3$, $Y^4$, $W^1$, $W^2$ and n have the earlier given significations).

A compound represented by the general formula [II] can be obtained by converting a compound represented by the general formula [IV] (which is prepared by a method as described in, for example, J. Med. Chem., 38, 2009, 1995) to a compound represented by the general formula [V] through a) alkylation using the compound 1 or b) reductive alkylation using the compound 2, and successively deprotecting the protective group $P^1$ on the compound represented by the general formula [V].

Said alkylation reaction of the compound represented by the general formula [IV] with compound 1 can be conducted by the means known per se.

When reductive alkylation is intended, the compound represented by the general formula [IV] and the compound 2 are reacted in the presence of a reducing agent (e.g. sodium cyanoborohydride) according to a known method (e.g., see J. Org. Chem., Vol. 50, p. 1927, 1985).

A compound represented by the general formula [II] can be also prepared by the methods as described in WO02/088089, WO96/40136 or WO98/57940.

Production Processes of the Compounds Represented by the General Formula [I-1] or [I-2]

Compounds represented by the general formula [I-1] or [I-2] can be prepared by those processes similar to the production processes of the compounds represented by the general formula [I]. For example, compounds of the general formula [I-1] can be prepared through amidation reaction of compounds of a general formula [IIa] with those of a general formula [IIIa] as in the following reaction process 3, in the manner following the production process 1.

Production Process 3

Reaction Scheme 3

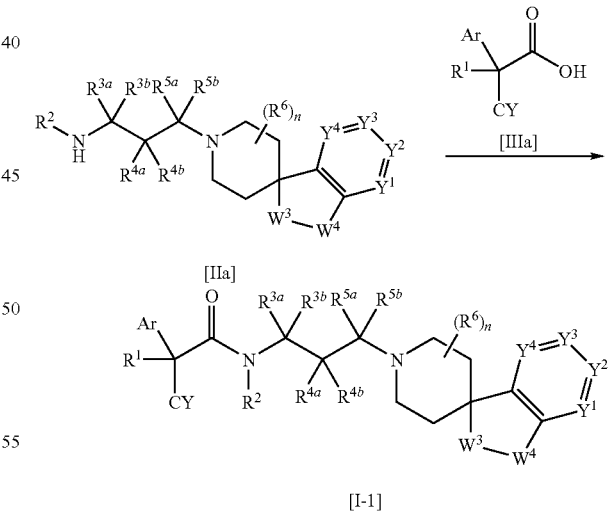

[I-1]

[in which $R^1$, $R^2$, $R^{3a}$, $R^{3b}$, $R^{4a}$, $R^{4b}$, $R^{5a}$, $R^{5b}$, $R^6$, $Y^1$, $Y^2$, $Y^3$, $Y^4$, Ar, CY, $W^3$, $W^4$ and n have the earlier given significations]

In particular, compound 6 which corresponds to the spiro ring moiety in those compounds represented by the general formula [I-1] can be prepared by processes known from literature references (e.g., see WO02/088089). It can also be prepared by the following production process 4.

Production Process 4

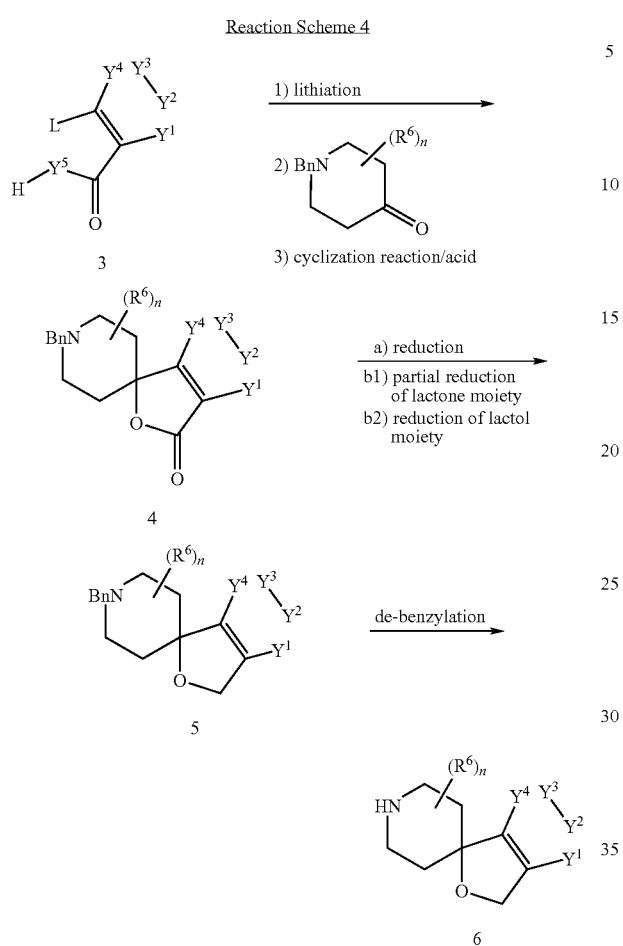

[in which L stands for hydrogen or halogen, $Y^5$ stands for —O— or —NR, R standing for $C_1$-$C_3$ lower alkyl, Bn stands for benzyl, and $R^6, Y^1, Y^2, Y^3, Y^4$ and n have the earlier given significations.].

A commercially available compound 3 is lithiated in THF at −78° C., to which a benzylpiperidin-4-one derivative is added, stirred for 2 hours at −78° C., and the product is cyclized with an acid such as hydrochloric acid to provide a compound 4. Successively, carbonyl group in the compound 4 is reduced with borane to provide a compound 5. The compound 5 can also be obtained by partially reducing the lactone moiety of compound 4 to lactol with diisobutylaluminium hydride and further reducing the lactol with triethylsilane under acidic condition. Successively de-benzylation reaction of the compound 5 is conducted by catalytic reduction of its benzyl group using palladium-on-carbon catalyst, to provide a compound 6. Using the compound 6 as the starting material, the reaction following the production Process 2 is conducted to provide a compound represented by the general formula [IIa].

Compounds of the general formula [IIIa] are those of the general formula (III) in which Z is limited to CY, and can be prepared by production processes of compounds of the general formula [III].

Production Methods of the Compounds Represented by the General Formula [III]

As the compounds represented by the general formula [III], commercially available products can be used. Besides, various derivatives thereof can be prepared by the following production methods A-E. In each of the reactions, those various compounds serving as the starting materials are commercially available.

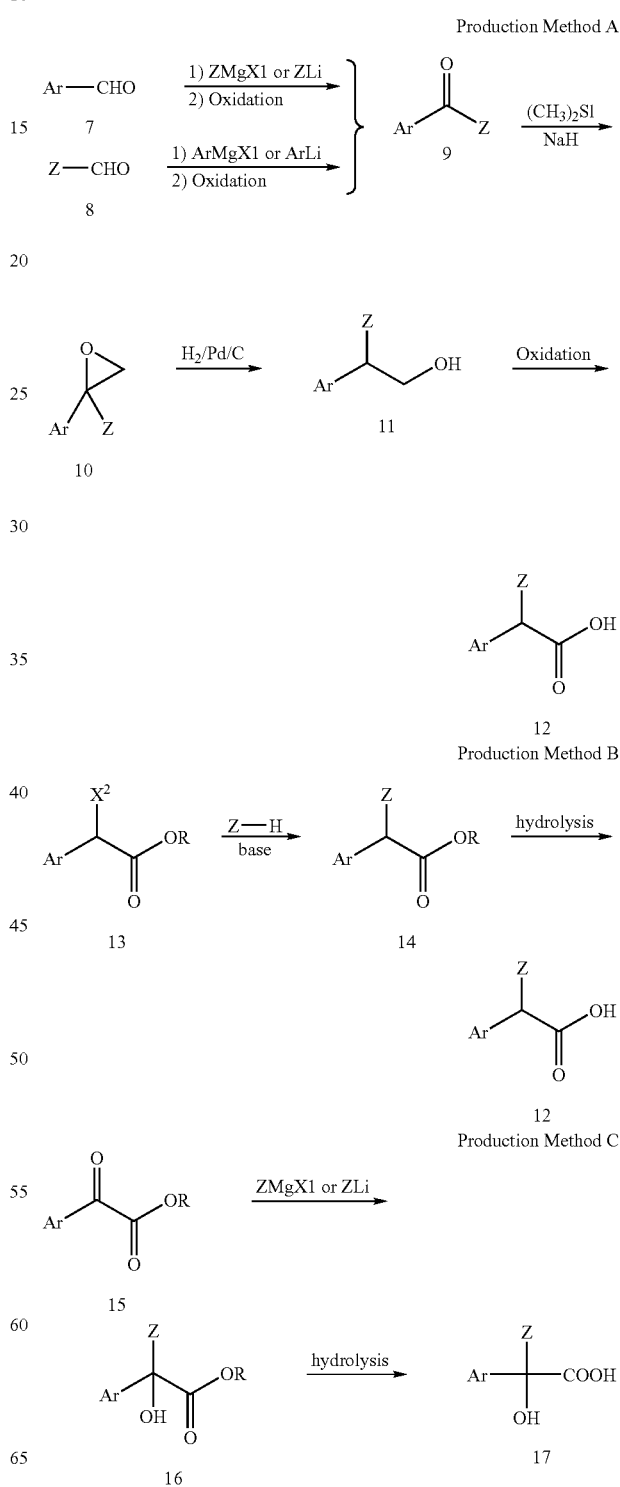

Production Method D

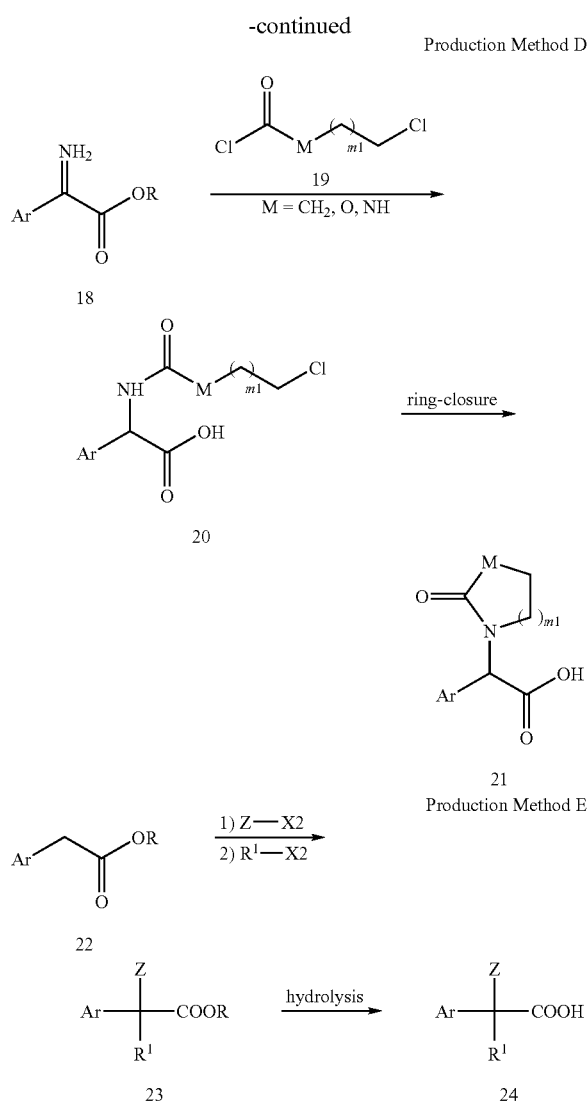

[in the formulae, X1 stands for chlorine, bromine or iodine; X2 stands for a leaving group such as chlorine, bromine, iodine, methanesulfonyloxy, p-toluenesulfonyloxy and the like; M stands for —$CH_2$—, —O— or —NH—; m1 stands for 1 or 2; and Ar, Z, R and $R^1$ have the earlier given significations].

Production Method A

Compound 7 (e.g., benzaldehyde, 3,4-difluorobenzaldehyde or the like) is reacted either with ZMgX1 which is a Grignard reagent (e.g., phenylmagnesium bromide, cyclopentylmagnesium bromide or the like); or Z—Li which is a lithium compound (e.g., phenyllithium, 4-fluorophenyllithium, 2-thiazolyllithium, 2-fluoro-5-pyridyllithium, 6-methoxy-3-pyridyllithium or the like), and thereafter oxidized to provide compound 9. Compound 8 can also be converted to compound 9, by reacting it with ArMgX1 which is a Grignard reagent or with Ar—Li which is a lithium compound, and thereafter oxidizing the product with manganese dioxide or the like. Compound 9 is then subjected to a carbon-increasing reaction using trimethylsulfonium iodide in the presence of sodium hydride (e.g., see J. Heterocycl. Chem., Vol. 25, p. 1917, 1988) to be converted to compound 10, which is subsequently hydrogenated in the presence of palladium-on-carbon catalyst to be converted to compound 11. Compound 11 is successively oxidized with chromic acid to provide compound 12. As the lithium compound (Z—Li or Ar—Li), those which are commercially available can be used, or they can be easily prepared by mixing corresponding halogen derivatives with n-BuLi.

Production Method B

Compound 13 is converted to compound 14 through reaction with Z—H in the presence of a base such as triethylamine sodium hydride or the like. Compound 14 is then hydrolyzed to be converted to compound 12. Here as Z—H, those having aliphatic heterocycle or aromatic heterocycle are preferred, examples of which include imidazole, 2-methylimidazole, 1,2,3-triazole, 1,2,4-triazole, pyrazole, 4-mesylpiperazin-2-one and the like.

Production Method C

Compound 15 and ZMgX1 or Z—Li are subjected to an addition reaction following the production method A, to form compound 16. Successively hydrolyzing the compound 16, compound 17 is obtained.

Production Method D

Compound 18 is subjected to an acylation reaction using compound 19, in the presence of a base such as triethylamine, to provide compound 20. The compound 20 is treated with a base such as potassium tert-butoxide to effect a ring-closing reaction and provide compound 21.

Production Method E

Compound 22 is stepwise reacted with Z—X2 and $R^1$—X2 (e.g., cyclopentyl bromide, methyl iodide or the like) in the presence of a base such as sodium hydride, lithium diisopropylamide or the like, to form compound 23. Then the compound 23 is hydrolyzed to compound 24.

Production Method F

Whereas, those compounds represented by the general formula [III] can be prepared by Production method F, in case $R^1$ and Z in the compounds represented by the general formula [I] together form a 3 to 6-membered ring with the carbon atom to which they bind.

Production Method F

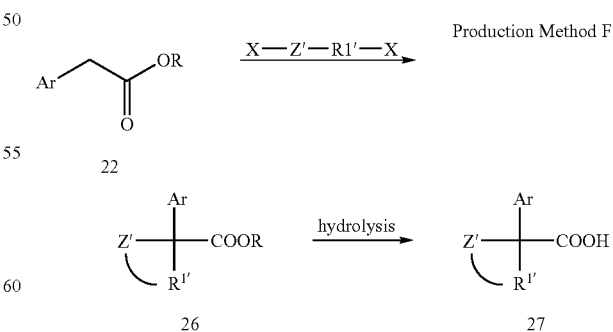

[in the formulae, Z' and R1' stand for a 3- to 6-membered aliphatic carbocyclic group or aliphatic heterocyclic group of a formula

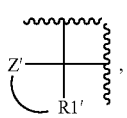

which may have a substituent selected from Group α, R stands for $C_1$-$C_3$ lower alkyl, and X and Ar have the earlier given significations].

A commercially available compound 22 is reacted with compound 25 in the presence of a base such as sodium hydride, lithium diisopropylamide or the like, to provide compound 26. Successively an ester of the compound 26 is hydrolyzed to compound 27. Here as examples of the compound 25, 1,2-dibromoethane, di(2-chloroethyl)ether, bis(2-bromoethyl)carbamic acid-t-butyl ester and the like can be named.

Production Process 5

Compounds which are represented by the general formula [I-3], i.e., compounds of the general formula [I] whose $R^1$ is hydroxyl can be prepared also by the following method.

Reaction Scheme 5

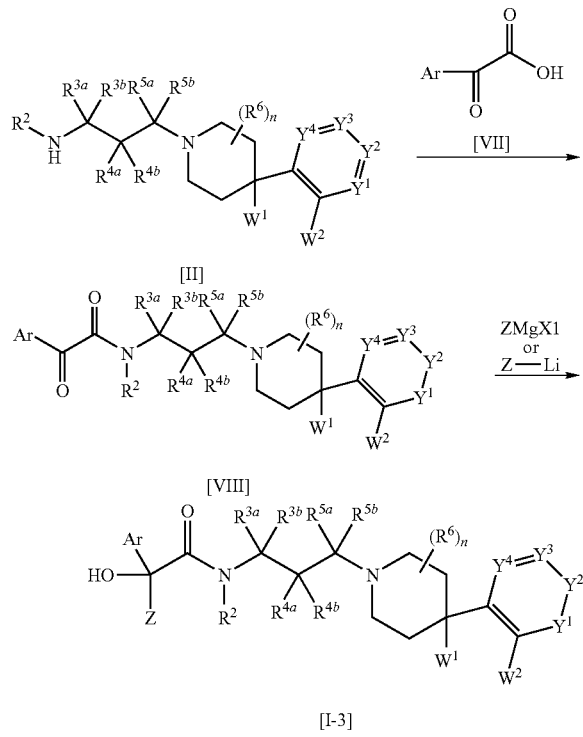

in the formulae, $R^2$, $R^{3a}$, $R^{3b}$, $R^{4a}$, $R^{4b}$, $R^{5a}$, $R^{5b}$, $R^6$, $Y^1$, $Y^2$, $Y^3$, $Y^4$, $W^1$, $W^2$, Ar, Z, X1 and n have the earlier given significations].

That is, a compound represented by the general formula [II] and a compound represented by the general formula [VII] are amidated following the Production process 1, to form a compound represented by the general formula (VIII). Successively the compound of the general formula (VIII) is reacted with Z—MgX1 or Z—Li which are organometal reagent, to obtain a compound represented by the general formula [I-3]. The reaction of compound of the general formula [VIII] with said organometal reagent can be conducted following production method C. As the compounds represented by the general formula [VII], those listed in Referential Examples can be used.

In the foregoing Production processes 1-5, when such groups as amino, hydroxyl, carboxyl, oxo, carbonyl and the like which do not participate in the reaction are present in the reactant(s), they can be suitably protected with protective groups of amino, hydroxyl, carboxyl, oxo or carbonyl, respectively, before carrying out the reactions. After each of the reactions, the protective groups can be removed.

As "amino-protective group", aralkyl such as benzyl, p-methoxybenzyl, 3,4-dimethoxybenzyl, o-nitrobenzyl, p-nitrobenzyl, benzhydril, trityl and the like; lower alkanoyl such as formyl, acetyl, propionyl, butyryl, pivaloyl and the like; benzoyl; arylalkanoyl such as phenylacetyl, phenoxyacetyl and the like; lower alkoxycarbonyl such as methoxycarbonyl, ethoxycarbonyl, propyloxycarbonyl, tert-butoxycarbonyl and the like; aralkyloxycarbonyl such as benzyloxycarbonyl, p-nitrobenzyloxycarbonyl, phenethyloxycarbonyl, fluorenylmethoxycarbonyl and the like; lower alkylsilyl such as trimethylsilyl, tert-butyldimethylsilyl and the like and phthaloyl and the like can be named. In particular, acetyl, pivaloyl, benzoyl, ethoxycarbonyl, tert-butoxycarbonyl and phthaloyl are recommended.

As "hydroxyl-protective group", for example, lower alkyl such as methyl, ethyl, propyl, isopropyl, tert-butyl and the like; lower alkylsilyl such as trimethylsilyl, tert-butyldimethylsilyl and the like; lower alkoxymethyl such as methoxymethyl, 2-methoxyethoxymethyl and the like; tetrahydropyranyl; trimethylsilylethoxymethyl; aralkyl such as benzyl, p-methoxybenzyl, 2,3-dimethoxybenzyl, o-nitrobenzyl, p-nitrobenzyl, trityl and the like; and acyl such as formyl, acetyl and the like can be named. In particular, methyl, methoxymethyl, tetrahydropyranyl, trityl, trimethylsilylethoxymethyl, tert-butyldimethylsilyl and acetyl are recommended.

As "carboxyl-protective group", for example, lower alkyl such as methyl, ethyl, propyl, isopropyl, tert-butyl and the like; lower haloalkyl such as 2,2,2-trichloroethyl and the like; lower alkenyl such as 2-propenyl; and aralkyl such as benzyl, p-methoxybenzyl, p-nitrobenzyl, benzhydryl, trityl and the like can be named. In particular, methyl, ethyl, tert-butyl, 2-propenyl, benzyl, p-methoxybenzyl and benzhydryl are recommended.

As "oxo- or carbonyl-protective groups", acetals and ketals such as ethylene ketal, trimethylene ketal, dimethyl ketal and the like can be named.

Means for removing protective groups differ depending on kind of the protective groups and stability of individual compounds represented by the general formula [I]. For example, the removal is conducted following those methods described in literature [cf. Protective Groups in Organic Synthesis, T. W. Greene, John Wiley & Sons Co., (1981)] or those analogous thereto, by solvolysis using acid or base, i.e., a method of having, for example, from 0.01 mole to a large molar excess of acid, preferably trifluoroacetic acid, formic acid, hydrochloric acid or the like; or from equimolar to a large molar excess of base, preferably potassium hydroxide, calcium hydroxide or the like, act on the object compound; chemical reduction using hydrogenated metal complex or by catalytic reduction using palladium-on-carbon catalyst or Raney nickel catalyst.

Compounds which are obtained by the foregoing methods can be easily isolated and purified by heretofore known separation means. As such means, for example, solvent extraction, recrystallization, column chromatography, liquid chromatography, preparative chromatography and the like can be named.

Compounds of the present invention may have stereoisomers or tautomers such as optical isomers, diastereo isomers, geometrical isomers or the like, depending on the form of their substituents. All of these stereoisomers, tautomers and their mixtures are encompassed by the compounds of the present invention.

Pharmacological Test of Compounds Represented by the General Formula [I]

Medical utility of compounds of the present invention is verified, for example, by the following pharmacological test examples.

Pharmacological Test Example 1

(MCH Binding Inhibition Test)

A human MCH-1R encoding cDNA sequence [FEBS Letters, Vol. 398, p. 253 (1996); Biochimica et Biophisica Acta, Vol. 1401, p. 216 (1998)] was cloned to plasmid vector pEF/mic/cyto (Invitrogen Corporation). The obtained expression vector was transfected to a host cell CHO-K1 (American Type Culture Collection) using lipofectamine plus reagent (Life Technology Inc.) to provide MCH-1R expression cells.

Membrane samples prepared from the MCH-1R expression cells were incubated with each test compound and 50 pM of [$^{125}$I]MCH (NEN Co.), in an assay buffer (50 mM Tris buffer comprising 10 mM magnesium chloride, 2 mM ethylenediamine tetraacetate, 0.01% bacitracin and 0.2% bovine serum albumin; pH 7.4) at 25° C. for an hour, followed by filtration through Glass Filter GF/C (Wattman Co.). After washing the glass filter with 50 mM Tris buffer (pH7.4) comprising 10 mM magnesium chloride, 2 mM ethylenediamine tetraacetate and 0.04% Tween-20, radiative activity on the glass filter was measured. Non-specific binding was measured in the presence of 1 μM human MCH and 50% inhibition concentration ($IC_{50}$ value) of each test compound to specific [$^{125}$I] MCH binding was determined. The results were as shown in Table 1.

TABLE 1

| Test Compound | $IC_{50}$ (nM) |
|---|---|
| Example 6 | 5.0 |
| Example 12 | 1.0 |
| Example 18 | 1.9 |
| Example 28 | 1.9 |
| Example 33 | 1.4 |
| Example 43 | 0.2 |
| Example 48 | 6.5 |
| Example 60 | 2.5 |
| Example 67 | 1.0 |
| Example 88 | 1.7 |

As above, compounds of the present invention potently inhibited binding of MCH to MCH-1R and acted as MCH-1R antagonist. Therefore, compounds of the present invention are useful as preventing or treating agents for various diseases associated with MCH, as they inhibit binding of MCH to the receptor thereof. Examples of such diseases include metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

Pharmaceutical Compositions Containing the Compounds Represented by the General Formula [I]

Those compounds of the present invention can be administered orally or parenterally, and when formulated into preparation forms adapted for administration, can provide preventing or treating agents for metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation. In particular, they are useful as preventing or treating agents for obesity.

In the occasions of clinical use of the compounds of the present invention, the compounds may be formulated into various forms of preparation with addition of pharmaceutically acceptable carriers according to the mode of administration, and thereafter administered. As carriers in such occasions, various additives heretofore known in the field of medical preparations can be used, examples of which include gelatine, lactose, sucrose, titanium dioxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropylcyclodextrin and the like.

As the preparation forms formulated as mixtures of these carriers and the compounds of the present invention, for example, solid preparations such as tablet, capsule, granule, powder or suppository; and liquid preparations such as syrup, elixir, or injection and the like can be named, which can be prepared following heretofore known methods in the field of medical preparations. Furthermore, liquid preparations may take such a form as to be dissolved or suspended in water or in other suitable medium immediately before use. Particularly, injections can be dissolved or suspended in physiological brine solution or glucose solution where necessary, and buffer or preservative may further be added thereto.

Those preparations can contain the compounds of the present invention at a rate of 1.0-100% by weight, preferably 1.0-60% by weight, to the whole of individual pharmaceutical preparation; and 0-99.0% by weight, preferably 40-99.0% by weight, of pharmaceutically acceptable carrier. These preparations may also contain therapeutically active other compound(s), for example, treating agents for diabetes, hypertension, arterial sclerosis and the like.

In case of using the compounds of the present invention as preventing or treating agents of said diseases or sicknesses, their dosages and administration frequency differ depending on sex, age, body weight and seriousness of symptoms of individual patients and the kind and scope of intended therapeutic effect. Whereas, generally for oral administration, it is preferred to administer 0.01-20 mg/kg per day per adult patient, as a single dose or several divided doses. For parenteral administration preferably 0.002-10 mg/kg is administered as a single dose or several divided doses. Depending on symptoms, preventing administration is permissible.

Combination Therapy

The compounds of the present invention can be used in combination with drugs effective for hypertension, obesity-associated hypertension, hypertension-associated diseases, cardiac hypertrophy, left ventricular hypertrophy, metabolic disorder, obesity, obesity-associated diseases and the like (hereafter referred to as "drug for combined use"). Such drugs can be administered simultaneously, separately or in succession, for prevention or treatment of above-named diseases. When a compound of the present invention is used simultaneously with one, two or more of drugs for combined use, they may be formulated into a medical preparation suited for single administration form. Whereas, for occasions of combination therapy, a composition containing the compound of the present invention and drug(s) for combined use may be administered to the object of medication in different packages, either simultaneously, separately or successively. They may be administered at time interval(s).

Dose(s) of drug(s) for combined use are determinable following clinically adopted dose(s), which can be suitably selected according to individual object of medication, administration route, specific disease, combination of drugs, and the like. Form of administering drug(s) for combined use is not critical but it is sufficient that the compound of the present invention is combined with selected drug(s) for combined use at the time of administration. As adoptable administration forms, for example, 1) administration of single preparation obtained by simultaneously formulating a compound of the present invention and drug(s) for combined use, 2) simultaneous administration of two kinds of preparations obtained by separately formulating a compound of the present invention and drug(s) for combined use, via a same administration route, 3) administration at a certain time interval, via a same administration route, of two kinds of preparations obtained by separately formulating a compound of the present invention and drug(s) for combined use, 4) simultaneous administration of two kinds of preparations obtained by separately formulating a compound of the present invention and drug(s) for combined use, via different administration routes, and 5) administration of two kinds preparations obtained by separately formulating the compound of the present invention and drug(s) for combined use, different administration routes, at a certain time interval (e.g., administration by the order of the compound of the present invention and then the drug(s) for combined use, or by the reversed order) can be adopted. The blend ratio of a compound of the present invention and drug(s) for combined use can be suitably selected, according to individual object of medication, administration route, disease and the like.

As drugs for combined use which can be used in the present invention, for example, those for treating diabetes, hyperlipidemia, hypertension, obesity and the like can be named. Two or more of such drugs for combined use may be combined at an adequate ratio and used.

As drug for treating diabetes, for example, 1) PPAR γ agonists such as glitazones [e.g., ciglitazone, darglitazone, englitazone, isoglitazone (MCC-555) and the like], pioglitazone, rosiglitazone, troglitazone, BRL49653, CLX-0921, 5-BTZD, GW-0207, LG-100641, LY-300512 and the like; 2) biganides such as metformin, buformin, phenformin and the like; 3) protein tyrosine phosphatase-1B inhibitor; 4) sulfonylureas such as acetohexamide, chloropropamide, diabinese, glibenclamide, glipizide, glyburide, glimepiride, gliclazide, glipentide, gliquidone, glisolamide, tolazamide, tolbutamide and the like; 5) meglitinides such as repaglinide, nateglinide and the like; 6) α-glucosidohydroxylase inhibitors such as acarbose, adiposine, carniglibose, emiglitate, miglitol, voglibose, pradimicin-Q, salbostatin, CKD-711, MDL-25,673, MDL-73,945, MOR 14 and the like; 7) α-amylase inhibitors such as tendamistat, trestatin, Al 3688 and the like; 8) insulin secretion promoters such as linogliride, A-4166 and the like; 9) fatty acid oxidation repressors such as clomoxir, etomoxir and the like; 10) A2 antagonists such as midaglizole, isoglidole, deriglidole, idozoxan, earoxan, fluparoxan and the like; 11) insulin or insulin mimetics such as biota, LP-100, novarapid, insulin detemir, insulini lispro, insulin glargine, insulin zinc, Lys-Pro-insulin, GLP-1(73-7), GLP 1 amide (7-36) and the like; 12) non-thiazolidindione such as JT-501, farglitazar and the like; and 13) PPARα/γdual agonists such as MK-0767, CLX-0940, GW-1536, GW-1929, GW-2433, KRP-297, L-796449, LR-90 and SB219994 and the like; can be named.

As said treating agent for hyperlipidermia, for example, 1) cholic acid absorbefacients such as colestrylamine, colesevelem, colestipol, dialkylaminoalkyl derivatives of crossdextran, Colestid™, LoCholest™, Ovestram™ and the like; 2) HMG-CoA reductase inhibitors such as atorvastatin, itavastatin, fluvastatin, lovastatin, pravastatin, rivastatin, rosuvastatin, simvastatin, ZD-4522 and the like; 3) HMG-CoA synthesis inhibitors; 4) cholesterol absorption inhibitors such as snatol ester, β-sitosterol, sterol gluoside, ezetimibe and the like; 5) acyl coenzyme A cholesterol acyl transferase inhibitors such as avasimibe, eflucimibe, KY-505, SMP-709 and the like; 6) CETP inhibitors such as JTT 705, torcetrapib, CP532632, BAY-63-2149, SC-591, SC-795 and the like; 7) squalene synthesis inhibitors; 8) antioxidants such as probucol; 9) PPARα agonists such as beclofibrate, benzafibrate, ciprofibrate, clofibrate, ethofibrate, fenofibrate, gemcabene, gemfibrozil, GW-7647, BM-170744, LY-518674, fibric acid derivatives [e.g., Atromid™, Lopid™, Tricor™ and the like; 10) FXR receptor antagonists such as GW-4064, SR-103912 and the like; 11) LXR receptor agonists such as GW3965, T9013137, XTCO-179628 and the like; 12) lipoprotein synthesis inhibitors such as niacin; 13) renin-angiotensin inhibitors; 14) microsome-triglyceride transport inhibitors; 15) cholic acid resorption inhibitors such as BARA 1453, SC435, PHA384640, S435, AZD7706 and the like; 16) PPAR δ agonists such as GW501516, GW590735 and the like; 17) triglyceride synthesis inhibitors; 18) MTTP inhibitors such as LAB687, CP346086 and the like; 19) low density lipoprotein receptor inducer; 20) squalene epoxidase inhibitors; 21) thrombocyte agglutination inhibitors; and 22) 5-lipoxygenase-activating protein inhibitors; can be named.

As said treating agents for hypertension, for example, 1) diuretic such as thiazide-type diuretic, e.g., chlorothialidon, chlorothiazide, dichlorophenamide, hydrofluorothiazide, indapamide, hydrochlorothiazide and the like; loop-type diuretic, e.g., bumetanide, ethacrynic acid, furosemide, torsemide and the like; sodium-type diuretic such as amiloride, triamterene and the like; and aldosterone antagonist-type diuretic, e.g., spironolactone, epirenone and the like; 2) β-adrenaline blockers such as acebutolol, atenolol, betaxolol, bevantolol, bisoprolol, bopindolol, carteolol, carvedilol, celiprolol, esmolol, indenolol, metaproplol, nadolol, nebivolol, penbutolol, pindolol, propanolol, sotalol, tertatolol, tilisolol, timolol and the like; 3) calcium channel blockers such as amlodipine, aranidipine, azelnidipine, barnidipine, benidipine, hepridil, cinaldipine, clevidipine, diltiazem, efonidipine, felodipine, gallopanil, isradipine, lacidipine, lernildipine, lercanidipine, nicardipine, nifedipine, nilvadipine, nimodepine, nisoldipine nitrendipine, manidipine, pranidipine, verapamil and the like; 4) angiotensin alteration enzyme inhibitors such as benazepril, captopril, cilazapril, delapril, enalapril, fosinopril, imidapril, losinopril, moexipril quinapril, quinaprilat, ramipril, perindopril, perindropril, quanipril, spirapril, tenocapril, trandolapril, zofenopril and the like; 5) neutral endopeptidase inhibitors such as omapatrilat, cadoxatril, ecadotril, fosidotril, sampatrilat, AVE 7688, ER 4030 and the like; 6) endothelin antagonists such as tezosentan, A308165, YM62899 and the like; 7) vasodilators such as hydrazine, clonidine, minoxidil, nicotinyl alcohol and the like; 8) angiotension II antagonists such as candesartan, eprosartan, irbesartan, losartan, pratosartan, tasosartan, telmisartan, valsartan, EXP-3137, FI6828K, RNH6270 and the like; 9) α/β adrenaline blockers such as nipradilol, arotinolol, amosulalol and the like; 10) α1 blockers such as terazosin, urapidil, prazosin, bunazosin, trimazosin, doxazosin, naftopidil, indoramin, WHIP164, XEN010 and the like; 11) α2 agonists such as lofexidine, tiamenidine, moxonidine, rilmenidine, guanobenz and the like; and 12) aldosteron inhibitors can be named.

As said anti-obesity agents, for example, 1) 5HT (serotonin) transporter inhibitors such as paroxetine, fluoxetine, fenfluramine, fluvoxamine, sertraline, imipramine and the like; 2) norepinephrine transporter inhibitors such as GW320659, desipramine, talsupram, nomifensine and the like; 3) cannabinoid 1 receptor 1(CB-1) antagonist/inverse agonist such as rimonabant (Sanofi Synthelabo), SR-147778 (Sanofi Synthelabo), BAY-65-2520 (Bayer), SLV-319 (Sorbay) and those compounds disclosed in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546, and the like; 4) ghrelin antagonists such as those compounds disclosed in, e.g., WO01/87355 and WO02/08250; 5) histamine (H3) antagonist/inverse agonist such as thioperamide, 3-(1H imidazol-4-yl) propyl N-(pentenyl) carbonate, clobenpropit, iodophenpropit, imoproxifan, GT2395, A331440, compounds disclosed in WO02/15905, 0-[3-(1H-imidazo-4-yl)propanol] carbamate, piperazin-containing H3 receptor antagonist (Lazewska, D. et al., Pharmazie, 56:927-32 (2001), benzophenone derivatives (Sasse, A. et al., Arch. Pharm. (Weinheim) 334:45-52 (2001)) substituted N-phenyl-carbamate (Reidemeister, S. et al., Pharmazie, 55:83-6 (2000)), proxyphene derivatives (Sasse, A. et al., J. Med. Chem. 43:3335-43 (2000)) and the like; 6) MCH-1R antagonists such as T-226296(Takeda), SNAP-7941(Synaptic) and other compounds disclosed in WO01/82925, WO01/87834, WO02/051809, WO02/06245, WO02/076929, WO02/076947, WO02/04433, WO02/51809, WO02/083134, WO02/094799, WO03/004027 and JP2001-226269A, and the like; 7) MCH-2R agonist/antagonists; 8) NPY1 antagonists such as 3-chloro-5-(1-(6-[2-(5-ethyl-4-methyl-thiazol-2-yl)-ethyl]4-morpholinyl-4-yl-pyridin-2-ylamino)-ethyl) phenyl]carbamic acid isopropyl ester, BIBP3226, BIB03304, LY-357897, CP-671906, GI-264879, and other compounds disclosed in U.S. Pat. No. 6,001,836, WO96/14307, WO01/23387, WO99/51600, WO01/85690, WO01/85098, WO01/85173 and WO01/89528, and the like; 9) NPY5 antagonists such as L-152804, GW-569180A, GW-594884A, GW-587081x, GW-548118x, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 6,340,683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789 and Norman et al., J. Med. Chem. 43:4288-4312 (2000), and the like; 10) leptins such as human recombinant leptin (PEG-OB, Hoffman La Roche), recombinant methionyl-leptin (Amgen) and the like; 11) leptin derivatives such as those compounds which are disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, WO96/23518, WO96/23519 and WO96/23520, and the like; 12) opioid antagonists such as Nalmefene (registered trademark to Revex), 3-methoxynaltrexone, naloxone, naltrexone, compounds disclosed in WO00/21509 and the like; 13) orexin antagonists such as SB-334867A and other compounds disclosed in WO01/96302, WO01/68609, WO02/51232, WO02/51838, WO03/023561, and the like; 14) bombesin receptor subtype 3 agonist; 15) cholecystokinin A (CCK-A) agonists such as AR-R15849, GI-181771, JMV-180, A-71378, A-71623, SR-146131, other compounds disclosed in U.S. Pat. No. 5,739,106, and the like; 16) CNTF (ciliary neurotrophic factors) such as GI-181771 (Glaxo-SmithKline), SR146131 (Sanofi Synthelabo), butabindide, PD170,292, PD149164 (Pfizer) and the like; 17) CNTF derivatives such as axokine (Regeneron), other compounds which are disclosed in WO94/09134, WO98/22128 and WO99/43813, and the like; 18) growth hormone secretion receptor agonists such as NN 703, hexarelin, MK-0677, SM-130686, CP424,391, L-692,429, L-163,255, U.S. Pat. No. 6,358,951,U.S. Patent Application Nos. 2002/049196 and 2002/022637, WO01/56592 and WO02/32888, and the like; 19) serotonin receptor 2C agonists such as BVT933, DPCA37215, IK264, PNU22394, WAY 161503, R-1065, YM348, other compounds disclosed in U.S. Pat. No. 3,914,250, WO02/36596, WO02/48124, WO02/10169, WO01/66548, WO02/44152, WO02/51844, WO02/40456 and WO02/40457, and the like; 20) melanocortin 3 receptor agonist; 21) melanocortin 4 receptor agonists such as CHIR86036 (Chiron), ME-10142, ME-10145 (Melacure), other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/

11715, WO02/12178, WO02/15909, WO02/068387, WO02/068388, WO02/067869, WO03/007949 and WO03/009847, and the like; 22) monoamine resorption inhibitors such as Sibutramine (registered trademark to Meridia/Reductil) and salts thereof, other derivatives disclosed in U.S. Pat. No. 4,746,680 U.S. Pat. No. 4,806,570, U.S. Pat. No. 5,436,272, US Patent Application No. 2002/0006964, WO01/27068 and WO01/62341, and the like; 23) monoamine re-introjection inhibitors such as dexfenfluramine, fluoxetine, other compounds disclosed in U.S. Pat. No. 6,365,633, WO01/27060 and WO01/162341, and the like; 24) glucagons-like peptide 1 agonist; 25) Topiramate (registered trademark to Topimax); 26) phytopharm compound 57 (e.g., CP644,673); 27) acetyl CoA carboxylase 2 (ACC2) inhibitor; 28) β-adrenalin receptor 3 agonists such as AD9677/TAK677(Dainippon Pharmaceutical/Takeda Pharmaceutical), CL-316,243, SB418790, BRL-37344, L-796568, BMS-196085, BRL-35135A, CGPI2177A, BTA-243, W427353, Trecadrine, ZenecaD7114, SR59119A, other compounds disclosed in U.S. Pat. No. 5,705,515,U.S. Pat. No. 5,451,677, WO01/74782 and WO02/32897, and the like; 29) diacylglycerolacyl transferase 1 inhibitor; 30) diacylglycerolacyl transferase 2 inhibitor; 31) fatty acid synthesis inhibitors such as Cerulenin, C75 and the like; 32) phosphodiesterase inhibitors such as theofylline pentoxyfylline, zaprinast, sildenafil, amrinone, milrinone, cilostamide, rolipram, cilomilast and the like; 32) thyroid hormone 13 agonists such as KB-2611 (KaroBio BMS), other compounds disclosed in WO02/15845 and JP2000-256190A, and the like; 33) phytanic acid such as phytanic acid, 4-[(E)-2-(5, 6, 7, 8-tetrahydro-5, 5, 8, 8-tetramethyl-2-naphthalenyl)-1-propenyl]benzoic acid (TT-NPB), retinoic acid, other compounds disclosed in WO99/00123, and the like; 34) acyl estrogens such as oleoylestrone, compounds disclosed in del Mar-Grasa, M. et al., Obesity Reseach, 9: 202-9 (2001); 35) glucocorticoid antagonist; 36) 11-β hydroxysteroid dehydrognase-type inhibitors such as BVT 3498, BVT 2733, other compounds disclosed in WO01/90091, WO 01/90090 and WO01/90092, and the like; 37) stearyl-CoA desaturase 1 inhibitors; 38) dipeptidyl peptidase IV inhibitors such as isoleucine thiazolidide, valine pyrrolidide, NVP-DPP728 AF237, P93/01, TSL225, TMC-2A/2B/2C, FE999011, P9310/K364, VIP0177, SDZ274444, other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181, and the like; 39) lipase inhibitors such as Tetrahydro lipstatin (registered trademark to Orlistat/Xenical), Triton WR 1339, RHC 80267, lipstatin, tea saponin, diethylumbelliferyl phosphate, FL-386, WAY-121898, BAY-N-3176, valilactone, esteracin, ebelactone A, ebelectone B, RHC80267, other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438 and U.S. Pat. No. 4,242,453, and the like; 39) fatty acid transporter inhibitors; 40) dicarboxylate transporter inhibitors; 41) glucose transporter inhibitors; 42) phosphate transporter inhibitors; and the like can be named.

Those combination drugs are obtained by concurrent use of a compound of the present invention with one, two, or more of above drugs for combined use. Furthermore, said combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and antiobesity agent are useful for prevention or therapy of metabolic disorders with synergistic effect, when diabetes-treating agent(s) and/or hyperlipidemia-treating agent(s) are added thereto.

BEST MODE FOR CARRYING OUT THE INVENTION

Hereinafter the present invention is explained in detail referring to working Examples, it being understood that the invention is in no sense limited by said Examples. As the silica gel for columns, Wakogel™ C-300 (Wako Pure Chemical Industries Ltd.) and that for reversed phase columns, YMC-GEL™ ProC18 (K. K. YMC) were used. Mass spectra were measured with Quattro II (Micro Mass Co.).

Referential Example 1

2-(3,4-Difluorophenyl)-2-(2-oxo-1-pyrrolidinyl)acetic acid (1) To a solution of 3,4-difluorophenylglycine (8.27 g) and triethylamine (18.5 ml) in dioxane-water (50 ml-50 ml), 4-chlorobutyryl chloride (5.3 ml) was added dropwise under cooling with ice. Thereafter the system was stirred for 30 minutes at the same temperature, the solvent was removed under reduced pressure, and the residue was made acidic with diluted hydrochloric acid, followed by extraction with ethyl acetate. The organic layer was washed with saturated brine, dried over anhydrous sodium sulfate and condensed under reduced pressure. The resulting solid was washed with ether, to provide 2-[(4-chlorobutanoyl)amino]-2-(3,4-difluorophenyl) acetic acid (6.22 g) as a white solid.

(2) To a solution of above compound (3.17 g) in THF (35 ml), tert-butoxypotassium (2.56 g) was added in three fractional amounts under cooling with ice. The reaction liquid was stirred for an hour under cooling with ice, followed by addition of diluted hydrochloric acid and extraction with ethyl acetate. The organic layer was washed with saturated brine, dried over anhydrous sodium sulfate and condensed under reduced pressure. The resulting solid was washed with ether and the title compound (2.37 g) was obtained as colorless crystals.

1H-NMR (400 MHz, CDCl3, δ ppm): 1.82-1.97 (2H, m), 2.26-2.30 (2H, m), 2.94-2.98 (1H, m), 3.47-3.49 (1H, m), 5.64 (1H, s), 7.09-7.15 (1H, m), 7.32-7.47 (1H, m).

Referential Example 2

2-(4-Chlorophenyl)-2-(2-oxo-1-pyrrolidinyl)acetic acid

Referential Example 1 was repeated except that 3,4-difluorophenylglycine used in Referential Example 1-(1) was replaced with 4-chlorophenylglycine, to provide the title compound.

1H-NMR (300 MHz, d6-DMSO, δ ppm): 1.65-2.10 (2H, m), 2.10-2.40 (2H, m), 2.75-3.00 (1H, m), 3.35-3.60 (1H, m), 5.66 (1H, s), 7.20-7.55 (4H, m).

ESI-MS Found: m/z 253 [M–H]–

Referential Example 3

2-(4-Fluorophenyl)-2-(2-oxo-1-pyrrolidinyl)acetic acid Referential Example 1 was repeated except that 3,4-difluorophenylglycine used in Referential Example 1-(1) was replaced with 4-fluorophenylglycine, to provide the title compound.

1H-NMR (300 MHz, d6-DMSO, δ ppm): 1.65-2.10 (2H, m), 2.10-2.45 (2H, m), 2.70-3.00 (1H, m), 3.20-3.70 (1H, m), 5.67 (1H, s), 7.0-7.45 (4H, m).
ESI-MS Found: m/z 236 [M−H]−

Referential Example 4

2-(3,4-Difluorophenyl)-2-(2-oxo-1-piperidinyl)acetic acid Referential Example 1 was repeated except that 4-chlorobutyryl chloride used in Referential Example 1-(1) was replaced with 4-chloropentanoyl chloride, to provide the title compound as colorless crystals.
1H-NMR (300 MHz, d6-DMSO, δ ppm): 1.50-1.80 (4H, m), 2.20-2.40 (2H, m), 2.80-3.05 (1H, m), 3.15-3.45 (1H, m), 5.82 (1H, s), 7.05-7.25 (1H, m), 7.30-7.60 (2H, m).
ESI-MS Found: m/z 268 [M+H]−

Referential Example 5

2-(3,4-Difluorophenyl)-2-(2-oxo-1,3-oxazolan-3-yl) acetic acid

To a solution of 3,4-difluorophenylglycine (3.00 g) and triethylamine (6.7 ml) in dioxane-water (15 ml-15 ml), 2-chloroethyl chloroformate (1.7 ml) was added dropwise under cooling with ice. Thereafter the system was stirred for 30 minutes at the same temperature, and for further an hour at room temperature. The solvent was removed under reduced pressure, water was added to the residue which was subsequently extracted with ethyl acetate. The organic layer was washed with saturated brine, dried over anhydrous sodium sulfate and condensed under reduced pressure. The residue was dissolved in THF (30 ml), and to the solution t-butoxypotassium (4.0 g) was added in three fractional amounts under cooling with ice. The reaction liquid was stirred for 30 minutes under cooling with ice, diluted hydrochloric acid was added, and extracted with ether. The organic layer was washed with saturated brine, dried over anhydrous sodium sulfate and condensed under reduced pressure. The resulting solid was washed with hexane-ether, to provide the title compound as colorless crystals.

Referential Example 6

(1) 2-(4-Chlorophenyl)-2-cyclopentylacetic acid

4-Chlorophenylacetic acid (5.0 g) was dissolved in 10% hydrogen chloride-methanol solution (50 ml) and heated under reflux for 14 hours. The solvent then was removed under reduced pressure and saturated sodium hydrogencarbonate solution was added to the residue, followed by extraction with ethyl acetate. The organic layer was dried over anhydrous sodium sulfate and condensed under reduced pressure to provide methyl 2-(4-chlorophenyl)acetate (5.35 g) as a colorless, oily substance.
(2) To a solution of above compound (500 mg) and cyclopentyl bromide (0.32 ml) in DMF (3 ml), potassium tert-butoxide (395 mg) was added under cooling with ice. After 2.5 hours' stirring, water was added to the reaction liquid which then was extracted with ethyl acetate. The organic layer was washed with saturated brine, dried over anhydrous sodium sulfate and condensed under reduced pressure. The resulting residue was purified on silica gel column chromatography (hexane/ethyl acetate=50/1) to provide methyl 2-(4-chlorophenyl)-2-cyclopentyl acetate (685 mg) as a colorless oily substance.
(3) To a solution of above compound (262 mg) in methanol (8 ml), 4N aqueous sodium hydroxide solution (0.5 ml) was added, followed by 15 hours' stirring. The solvent was removed under reduced pressure and to the resulting residue 2N hydrochloric acid was added to render the latter acidic, and the resulting mixture was extracted with ethyl acetate. The organic layer was washed with saturated brine, dried over anhydrous sodium sulfate and condensed under reduced pressure to provide the title compound as a white solid.
1H-NMR (300 MHz, CDCl3, δ ppm): 0.85-1.08 (1H, m), 1.20-1.78 (6H, m), 1.87-2.01 (1H, m), 2.40-2.60 (1H, m), 3.27 (1H, d, J=11.0 Hz), 7.16-7.40 (4H, m), 9.45-10.6 (1H, br).

Referential Example 7

2-(4-Chlorophenyl)-2-cyclopentylpropionic acid (1) To a solution of diisopropylamine (0.15 ml) in THF (2 ml), n-butyl lithium (1.5 M hexane solution, 0.6 ml) was added at −78° C., stirred for 10 minutes and another solution of methyl 2-(4-chlorophenyl)-2-cyclopentylacetate (200 mg) in THF (1.5 ml) was added dropwise. After 15 minutes' stirring, the system temperature was raised to −35° C., and methyl iodide (0.15 ml) was added. The reaction liquid temperature was raised to 0° C., and the liquid was stirred for 1.5 hours, diluted with saturated aqueous ammonium chloride solution and extracted with diethyl ether. The organic layer was washed with saturated brine, dried over anhydrous sodium sulfate and condensed under reduced pressure. The resulting residue was purified on silica gel column chromatography (hexane/ethyl acetate 60/1) to provide methyl 2-(4-chlorophenyl)-2-cyclopentylpropionate (180 mg) as yellow oily substance.
(2) The above compound was processed in the manner similar to Referential Example 6-(3) to provide the title compound as a yellow oily substance.
1H-NMR (300 MHz, CDCl3, δ ppm): 0.99-1.16 (1H, m), 1.24-2.67 (6H, m), 1.51 (3H, s), 2.77 (1H, q, J=8.9 Hz), 7.20-7.40 (4H, m), 9.69-11.95 (1H, br).

Referential Example 8

1-(3,4-Difluorophenyl)cyclopropanecarboxylic acid (1) To a solution of methyl 2-(3,4-difluorophenyl)acetate (373 mg) and 1,2-dibromoethane (0.17 ml) in DMF (10 ml), sodium hydride (60% oily substance, 288 mg) was added. After 2 hours' stirring, saturated aqueous ammonium chloride solution was added to the reaction liquid, followed by extraction with ethyl acetate. The organic layer was washed with saturated brine, dried over anhydrous sodium sulfate and condensed under reduced pressure. The resulting residue was purified on silica gel column chromatography (hexane/ethyl acetate=50/1) to provide 1-(3,4-difluorophenyl)cyclopropanecarboxylate (161 mg) as a colorless oily substance.
(2) The above compound was processed as in Referential Example 6 to provide the title compound.
1H-NMR (400 MHz, CDCl3, δ ppm): 1.22-1.27 (2H, m), 1.65-1.70 (2H, m), 7.03-7.18 (3H, m).

Referential Example 9

1-(3,4-Difluorophenyl)-2,2-dimethylacetic acid

Referential Example 8 was repeated except that 1,2-dibromoethane used in Referential Example 8-(1) was replaced with methyl iodide, to provide the title compound.

Referential Example 10

1-(3,4-Difluorophenyl)-cyclopentanecarboxylic acid

Referential Example 8 was repeated except that 2-dibromoethane used in Referential Example 8-(1) was replaced with 1,4-dibromobutane, to provide the title compound.
ESI-MS Found: m/z255 [M−H]−

Referential Example 11

2-(4-Chlorophenyl)-2-cyclopentyl-2-hydroxyacetic acid (1) To a solution of ethyl 2-(4-chlorohenyl)-2-oxoacetate (510 mg) in THF (4 ml), cyclopentylmagnesium chloride (2M-ether solution, 1.8 ml) was added at −70° C. and stirred for an hour. To the reaction liquid saturated aqueous ammonium chloride solution was added and extracted with chloroform. The organic layer was dried over anhydrous sodium sulfate. The residue as obtained by condensing the organic layer under reduced pressure was purified on silica gel column chromatography (hexane/ethyl acetate=50/1) to provide ethyl 24-chlorophenyl)-2-cyclopentyl-2-hydroxyacetate (149 mg).

(2) Using the above compound, the title compound was obtained as a colorless solid, through the operations similar to Referential Example 63).
1H-NMR (300 MHz, CDCl3, δ ppm): 1.14-2.14 (10H, m), 2.71-3.10 (1H, m), 7.00-7.90 (4H, m).

Referential Example 12

2-(4-Chlorophenyl)-2-isopropyl-2-hydroxyacetic acid

Referential Example 11 was repeated except that cyclopentylmagnesium chloride used in deferential Example 11-(1) was replaced with isopropylmagnesium chloride, to provide the title compound.
1H-NMR (300 MHz, CDCl3, δ ppm): 0.68 (3H, d, J=6.7 Hz), 1.04 (3H, d, J=6.7 Hz), 2.44-2.70 (1H, m), 7.34 (2H, d, J=8.7 Hz), 7.57 (2H, d, J=8.7 Hz).

Referential Example 13

2-(4-Chlorophenyl)-2-hydroxy-2-(3-pyridinyl) acetic acid

To a solution of 3-bromopyridine (640 mg) in diethyl ether (10 ml), n-butyl lithium (2.5M-hexane solution, 1.80 ml) was added at −74° C. After 15 minutes' stirring at the same temperature, a solution of ethyl 2-(4-chlorophenyl)-2-oxoacetate (960 mg) in diethyl ether (100 ml) was added. The temperature of the system was raised to room temperature over 30 minutes, and to the reaction solution saturated aqueous ammonium chloride solution was added and extracted with diethyl ether. The organic layer was washed with saturated brine and dried over anhydrous sodium sulfate. The organic layer was condensed under reduced pressure, and the resulting residue was purified on silica gel column chromatography (hexane/ethyl acetate=3/2) to provide ethyl 2-(4-chlorophenyl)-2-hydroxy-2-(3-pyridinyl)acetate (571 mg) as a yellow oily substance.

1H-NMR (300 MHz, CDCl3, δ ppm): 1.26 (6H, s), 7.06-7.15 (2H, m), 7.16-7.26 (1H, m).

(2) To a solution of above compound (603 mg) in ethanol (12 ml), 1N aqueous sodium hydroxide solution (2 ml) was added and heated under reflux for 4 hours. The reaction liquid was condensed, and the resulting residue was rendered acidic with 2N hydrochloric acid and extracted with chloroform. The organic layer was washed with saturated brine, dried over anhydrous sodium sulfate and condensed under reduced pressure to provide the title compound (425 mg) as a brown solid.
1H-NMR (300 MHz, d6-DMSO, δ ppm): 7.30-7.50 (5H, m), 7.70 (1H, dd, J=8.0, 1.5 Hz), 8.49 (1H, d, J=4.8 Hz), 8.54 (1H, d, J=2.3 Hz).

Referential Example 14

2-(4-Chlorophenyl)-2-(1H-pyrrol-1-yl)acetic acid (1) 4-Chlorophenylglycine (225 mg) was dissolved in 10% hydrogen chloride-methanol solution (3 ml) and heated under reflux for 6.5 hours. The reaction liquid was cooled and condensed under reduced pressure. The resulting residue was dried to provide methyl 2-amino-2-(4-chlorophenyl)acetate hydrochloride (282 mg) as a white solid.

(2) Above compound (121 mg) was dissolved in acetic acid (2 ml), and to the solution sodium acetate (66 mg) and 2,5-dimethoxytetrahydrofuran (80 mg) were added, followed by heating at 90° C. After 1.5 hours' stirring, the reaction liquid was condensed under reduced pressure and the resulting residue was diluted with ethyl acetate and washed successively with saturated aqueous sodium hydrogencarbonate solution and with saturated aqueous sodium chloride solution. The organic layer was dried over anhydrous sodium sulfate and condensed under reduced pressure. The resulting residue was purified on silica gel column chromatography (hexane/ethyl acetate=50/1) to provide methyl 2-(4-chlorophenyl)-2-(1H-pyrrol-1-yl)acetate (108 mg) as a colorless oily substance.

(3) Using the above compound, the title compound was obtained as a yellow oily substance, through the operations similar to Referential Example 6-(3).
1H-NMR (300 MHz, CDCl3, δ ppm): 5.87 (1H, s), 6.12-6.32 (2H, m), 6.55-6.89 (2H, m), 7.12-7.55 (4H, m).

Referential Examples 15-16

Example 14 was repeated except that 4-chlorophenylglycine used therein was replaced with each a starting material corresponding to the intended compound, to provide the compounds of Examples 15 and 16.

Referential Example 15

2-(4-Fluorophenyl)-2-(1H-pyrrol-1-yl)acetic acid

ESI-MS Found: m/z 238 [M+H]+, 236 [M−H]

Referential Example 16

2-(3,4-Difluorophenyl)-2-(1H-pyrrol-1-yl)acetic acid

ESI-MS Found: m/z 220 [M+H]+, 218 [M−H]

Referential Example 17

2-(4-Chlorophenyl)-2-(1H-pyrazol-1-yl)acetic acid (1) To a solution of methyl 24-chlorophenyl) acetate (1.0 g) in carbon tetrachloride (14 ml), N-bromosuccinimide (1.05 g) and hydrobromic acid (3 drops) were added, followed by 2 hours' heating under reflux. The reaction liquid was cooled to room temperature and condensed under reduced pressure. Thus obtained residue was diluted with ethyl acetate and successively washed with saturated aqueous sodium hydrogencarbonate solution and then with saturated aqueous sodium chloride solution. The organic layer was dried over anhydrous sodium sulfate, condensed under reduced pressure, and the resulting residue was purified on silica gel column chromatography (hexane/ethyl acetate=40/1) to provide methyl-2-bromo-2-(4-chlorophenyl)acetate (1.43 g).

(2) To a suspension of sodium hydride (60% oily substance, 100 mg) in THF (6 ml), a solution of pyrazole (170 mg) in THF (4.5 ml) was added at −18° C. After stirring the system for 30 minutes at the same temperature, another solution of the compound formed in above (1) (650 mg) in THF (4 ml) was added. Raising the temperature to room temperature, the reaction liquid was stirred for 24 hours. Water was added to the reaction liquid which was then extracted with ethyl acetate, washed with saturated brine and dried over anhydrous sodium sulfate. The organic layer was condensed under reduced pressure and the resulting residue was purified on silica gel column chromatography (hexane/ethyl acetate=8/1) to provide methyl 2-(4-chlorophenyl)-2-(1H-pyrazol-1-yl) acetate (232 mg) as a colorless oily substance.

(3) Using the above compound, the title compound was obtained as a colorless solid, through the operations similar to Referential Example 6-(3).

1H-NMR (300 MHz, d6-DMSO, δ ppm): 6.26 (1H, d, J=2.3 Hz), 6.40 (1H, s), 7.45 (4H, s), 7.49 (1H, d, J=1.7 Hz), 7.72 (1H, d, J=2.3 Hz).

Referential Example 18

2-(3,4-Difluorophenyl)-2-(1H-pyrazol-1-yl)acetic acid

Referential Example 17 was repeated except that methyl 2-(4-chlorophenyl)acetate used in Referential Example 17-(1) was replaced with methyl 2-(3,4-difluorophenyl)acetate, to provide the title compound.

ESI-MS Found: m/z 239 [M+H]+, 237 [M−H]

Referential Example 19

2-(3,4-Difluorophenyl)-2-(2-oxo-1(2H)pyridinyl) acetic acid (1) Referential Example 15-(1) was repeated except that methyl 2-(4-chlorophenyl)acetate used in Referential Example 17-(1) was replaced with methyl 2-(3,4-difluorophenyl)acetate, to provide methyl 2-bromo-2-(3,4-difluorophenyl)acetate.

(2) To a solution of above compound (792 mg) and 2-hydroxypyridine (380 mg) in DMF (10 ml), potassium carbonate (553 mg) was added and stirred for an overnight at room temperature. Water was added to the reaction liquid, followed by extraction with ether, washing with saturated brine and drying over anhydrous sodium sulfate. The organic layer was condensed under reduced pressure and the resulting residue was purified on silica gel column chromatography (hexane/ethyl acetate=1/1) to provide methyl 2-(3,4-difluorophenyl)-2-(2-oxo-1(2H)pyridinyl)acetate (553 mg) as an oily substance.

(3) Using the above compound, the title compound was obtained as a colorless amorphous substance, through the operations similar to Referential Example 6-(3).

1H-NMR (300 MHz, CDCl3, δ ppm): 6.25-6.29 (1H, m), 6.51 (1H, s), 6.64-6.68 (1H, m), 7.10-7.26 (4H, m), 7.40-7.45 (1H, m).

Referential Example 20

2-(3,4-Difluorophenyl)-2-(2H-1,2,3,4-tetrazol-2-yl) acetic acid (1) To a mixed solution of 1H-tetrazole (350 mg) in THF (5 ml) and DMF (5 ml), potassium carbonate (553 mg) was added and stirred for 30 minutes at room temperature. Subsequently a solution of methyl 2-bromo-2-(3,4-difluqrophenyl)acetate (1.06 g) in THF (2 ml) was added, followed by 2 hours' stirring. Water was added to the reaction liquid, followed by extraction with ether. The organic layer was washed with saturated brine, dried over anhydrous magnesium sulfate and condensed under reduced pressure. The resulting residue was purified on silica gel column chromatography (hexane/ ethyl acetate=5/1) to provide methyl 2-(3,4-difluorophenyl)-2-(2H-1,2,3,4-tetrazol-2-yl)acetate (507 mg) as an oily substance.

(2) Using the above compound, the title compound was obtained through the operations similar to Referential example 6-(3).

Referential Examples 21-23

Referential Example 17 was repeated except that methyl 2-(4-chlorophenyl) acetate used in Referential Example 17-(1) was replaced with methyl 2-(3,4-difluorophenyl)acetate, and pyrazole used in 17-(2) was replaced with each the starting material corresponding to the intended compound, to provide the compounds of Referential Examples 21-23.

Referential Example 21

2-(3,4-Difluorophenyl)-2-(1H-1,2,3-triazol-1-yl) acetic acid

1H-NMR (300 MHz, d6-DMSO, δ ppm): 6.86 (1H, s), 7.31-7.70 (3H, m), 7.75 (1H, s), 8.26 (1H, s).

Referential Example 22

2-(3,4-Difluorophenyl)-2-(1H-1,2,4-triazol-1-yl) acetic acid

1H-NMR (300 MHz, d6-DMSO, δ ppm): 6.49 (1H, s), 7.25-7.65 (3H, m), 7.99 (1H, s), 8.64 (1H, s).

Referential Example 23

2-(3,4-Difluorophenyl)-2-(4-(methanesulfonyl)-2-oxo-1-piperazinyl)acetic acid

ESI-MS Found: m/z 347 [M−H]−

Referential Example 24

2-(4-Chlorophenyl)-2-(1H-imidazol-1-yl)acetic acid

1) To a solution of imidazole (170 mg) and triethylamine (350 ml) in DMF (1 ml), a solution of methyl 2-bromo-2-(4-chlorophenyl)-acetate (657 mg) in DMF (3 ml) was added. After stirring for an overnight, water was added to the reaction liquid, followed by extraction with ethyl acetate, washing with saturated brine and drying over anhydrous sodium sulfate. The reaction liquid was condensed under reduced pressure and the resulting residue was purified on silica gel column chromatography (methanol/chloroform=1/10) to provide methyl 2-(4-chlorophenyl)-2-(1H-imidazol-1-yl)-acetate (400 mg) as a yellow oily substance.

(2) The above compound (381 mg) was dissolved in 0.32 N sodium hydroxide solution (7.0 ml, ethanol: water=95:5) and stirred for 2 hours. The reaction liquid was condensed under reduced pressure, and the resulting residue was acidified with 2N hydrochloric acid. To the resulting mixture ethanol was added and condensed under reduced pressure. Once again the residue was dissolved in ethanol under heating. The insoluble matter was removed by filtration. The filtrate was condensed under reduced pressure to provide the title compound (323 mg) as a white solid.

1H-NMR (300 MHz, d6-DMSO, δ ppm): 6.32 (1H, s), 7.05 (1H, d, J=0.6 Hz), 7.34 (1H, d, J=1.1 Hz), 7.45 (4H, s), 8.14 (1H, d, J=0.6 Hz).

Referential Examples 25-26

Referential Example 24 was repeated except that methyl 2-(4-chlorophenyl)acetate used in Referential Example 17-(1) was replaced with methyl 2-(3,4-difluorophenyl)acetate, and imidazole was replaced with each the starting material corresponding to the intended compound, to provide the compounds of Referential Examples 25-26.

Referential Example 25

2-(3,4-Difluorophenyl)-2-(2-methyl-1H-imidazol-1-yl)acetic acid

1H-NMR (300 MHz, d6-DMSO, δ ppm): 2.67 (3H, s), 6.58 (1H, s), 7.32-7.77 (5H, m).

Referential Example 26

2-(3,4-Difluorophenyl)-2-(4-methyl-1H-imidazol-1-yl)acetic acid

1H-NMR (300 MHz, d6-DMSO, δ ppm): 2.15 (3H, s), 6.30 (1H, s), 7.22-7.64 (4H, m), 8.57 (1H, s).

Referential Example 27

2,2-Bis(6-fluoro-3-pyridinyl)acetic acid (1) A solution of 5-bromo-2-fluoropyridine (10.24 g) in ether (400 ml) was cooled to −78° C., and into which n-butyl lithium (1.55M-hexane solution, 37.5 ml) was added dropwise. After 15 minutes' stirring, methyl formate (3.6 ml) and THF (40 ml) were added. After further 5 minutes' stirring, the reaction liquid was poured into an aqueous solution of potassium hydrogensulfate. The organic layer was separated and successively washed with an aqueous sodium hydrogencarbonate solution and with saturated brine. The organic layer was dried over anhydrous sodium sulfate and condensed under reduced pressure to provide 6-fluoronicotinic aldehyde (7.23 g).

(2) A solution of 6-fluoro-3-pyridinyl lithium solution [prepared through the steps of cooling a solution of 5-bromo-2-fluoropyridine (1.60 g) in ether (80 ml) to −78° C. and adding thereto n-butyl lithium (1.56M-hexane solution, 5.83 ml) dropwise, followed by 10 minutes' stirring], and into which a solution of above compound (1.13 g) in THF (40 ml) was added at −70° C. After 30 minutes' stirring, the reaction liquid was poured into an aqueous solution of potassium hydrogensulfate. The organic layer was separated and successively washed with an aqueous sodium hydrogencarbonate solution and with saturated brine. The organic layer was dried over anhydrous sodium sulfate and condensed under reduced pressure. The resulting residue was purified on silica gel chromatography (hexane/ethyl acetate=3/2-1/2) to provide 2,2-bis(6-fluoro-3-pyridinyl) methanol (1.14 g).

(3) To a solution of above compound (930 mg) in chloroform (30 ml), manganese dioxide (3.64 g) was added and stirred for 6 hours. The reaction liquid was filtered and the filtrate was condensed under reduced pressure to provide 2,2-bis(6-fluoro-3-pyridinyl) ketone (737 mg).

(4) To a solution of above compound (486 mg) and trimethylsulfonium iodide (901 mg) in DMSO (10 ml), sodium hydride (60% oiliness; 177 mg) was added under cooling with ice. After an hour's stirring, the reaction liquid was poured into ice water and extracted with ethyl acetate. The organic layer was successively washed with water and then with saturated brine, and dried over anhydrous sodium sulfate. The organic layer was condensed under reduced pressure, and the resulting residue was purified on silica gel column chromatography (hexane/ethyl acetate=3/1-2/1) to provide 2,2-bis(6-fluoro-3-pyridinyl) oxylan (480 mg).

(5) The above compound (480 mg) was dissolved in methanol (5 ml) and stirred in hydrogen atmosphere of one atmospheric pressure for 2.5 hours in the presence of 10% palladium-on-carbon (220 mg). Removing the palladium-on-carbon by filtration, the filtrate was condensed under reduced pressure. The residue was purified on column chromatography (hexane/ethyl acetate=1/2) to provide 2,2-bis(6-fluoro-3-pyridinyl)-1-ethanol (352 mg).

(6) The above compound (350 mg) was dissolved in acetone (5 ml), and to which Jones' reagent (5 ml) was added on ice both. The reaction liquid was stirred for 45 minutes at room temperature, and thereafter water and ether were added. The organic layer was separated and washed repeatedly with water. The last washing was conducted with saturated brine. The organic layer was dried over anhydrous sodium sulfate and condensed under reduced pressure to provide the title compound (175 mg) as crystals.

1H-NMR (400 MHz, CDCl3, δ ppm): 5.07 (1H, s), 6.94-6.97 (2H, m), 7.70-7.83 (2H, m), 8.22 (2H, s).

Referential Example 28

2,2-Bis(6-methoxy-3-pyridyl)acetic acid

Referential Example 27 was repeated except that 5-bromo-2-fluoropyridine which was used in Referential Example 27-(1) was replaced with 5-bromo-2-methoxypyridine, to provide the title compound.

ESI-MS Found: m/z 275 [M+H]+

Referential Example 29

2-(3,4-Difluorophenyl)-2-phenylacetic acid

Referential Example 27-(1) through (6) were repeated except that 6-fluoro-3-pyridinyl lithium and 6-fluoronicotinic aldehyde which were used in Referential example 27-(2)

were replaced with, respectively, phenylmagnesium bromide and 3,4-difuorobenzaldehyde, to provide the title compound.

Referential Example 30

2,2-Bis(4-fluorophenyl)acetic acid

Referential Example 27-(2) through (6) were repeated except that 6-fluoro-3-pyridinyl lithium and 6-fluoronicotinic aldehyde which were used in Referential Example 27-(2) were replaced with, respectively, 4-fluorophenylmagnesium bromide and 4-fluorobenzaldehyde, to provide the title compound.

1H-NMR (300 MHz, CDCl3, δ ppm): 5.01 (1H, s), 7.00-7.05 (4H, m), 7.26-7.31 (4H, m).

Referential Examples 31-35

Referential Example 27-(2)-(6) were repeated except that 6-fluoronicotinic aldehyde used in Referential Example 27-(2) was changed in each run in correspondence to the intended compound, to provide compounds of Referential Examples 31-35.

Referential Example 31

2-(6 Fluoro-3-pyridinyl)-2-(4-fluoropheny)acetic acid

1H-NMR (300 MHz, CDCl3, δ ppm): 5.02 (1H, s), 6.85-7.00 (1H, m), 7.00-7.10 (2H, m), 7.20-7.35 (1H, m), 7.70-7.85 (1H, m), 8.18 (1H, s).

ESI-MS Found: m/z 250 [M+H]+

Referential Example 32

2-(6-Fluoro-3-pyridinyl)-2-(6-trifluoromethyl-3-pyridinyl)-acetic acid

ESI-MS Found: m/z 301 [M+H]+

Referential Example 33

2-(6-Fluoro-3-pyridinyl)-2-phenylacetic acid

Referential Example 34

2-(6-Fluoro-3-pyridinyl)-2-(4-toluyl)acetic acid

Referential Example 35

2-(2-Fluoro-5-pyridinyl)-2-(2-methoxy-5-pyridinyl)acetic acid

ESI-MS Found: m/z 263 [M+H]+

Referential Example 36

4-(6-Fluoro-3-pyridinyl)-piperidine (1) A solution of 2-fluoro-5-bromopyridine (7.69 g) in diethyl ether (160 ml) was cooled to −78° C., and into which n-butyl lithium (1,56M-hexane solution, 30 ml) was added dropwise at a temperature not higher than −70° C. After 15 minutes' stirring, tert-butyl 4-oxo-1-piperidinecarboxylate (8.7 g) was added. Temperature of the reaction liquid was raised to −35° C. and water was added, followed by extraction with ethyl acetate. The organic layer was washed with saturated brine and dried over anhydrous sodium sulfate. The organic layer was condensed under reduced pressure and isopropyl ether was added to the resulting residue. Whereupon precipitated crystals were recovered by filtration to provide the title compound (4.15 g). The filtrate was purified on column chromatography (hexane/ethyl acetate=3/1-2/1) to provide tert-butyl 4-(6-fluoro-3-pyridinyl)-4-hydroxy-tetrahydro-1(2H)-pyridinecarboxylate (1.25 g).

(2) To a solution of above compound (5.4 g) and 4-dimethylaminopyridine (13.4 g) in chloroform (150 ml), methanesulfonyl chloride (3.53 ml) was added under cooling with ice. After raising the temperature to the ambient level, the system was stirred for an overnight. The reaction liquid was condensed under reduced pressure, ethyl acetate and aqueous citric acid solution were added to the residue, the mixture was stirred and the organic layer was separated. The organic layer was successively washed with water, saturated aqueous solution of sodium hydrogencarbonate and saturated brine. The organic layer was dried over anhydrous sodium sulfate, condensed under reduced pressure, and the resulting residue was purified on column chromatography (hexane/ethyl acetate=3/1) to provide tert-butyl 4-(6-fluoro-3-pyridinyl)-3,6-dihydro-1(2H)-pyridinecarboxylate (4.70 g).

(3) A solution of above compound (4.70 g) in THF (50 ml) was stirred for an overnight in an atmosphere of one atmospheric hydrogen pressure in the presence of 10% palladium-on-carbon (500 mg). The reaction liquid was filtered, condensed under reduced pressure, and the residue was purified on column chromatography (hexane/ethyl acetate=3/1) to provide tert-butyl 4-(6-fluoro-3-pyridinyl)-tetrahydro-1 (2H)-pyridinecarboxylate (4.60 g).

(4) The above compound (4.6 g) was dissolved in trifluoroacetic acid (10 ml) and stirred for 30 minutes at room temperature. The reaction liquid was condensed under reduced pressure. To the resulting residue an aqueous sodium hydroxide solution was added to render it alkaline, followed by extraction with ether. The organic layer was washed with saturated brine, dried over anhydrous sodium sulfate and condensed under reduced pressure to provide the title compound (3.0 g).

Referential Example 37

Spiro[5-fluoro-6-azaisobenzofuran-1(3H), 4'-piperidine]

(1) 2,3-Dichloropyridine (107.3 g) and cesium fluoride (268.2 g) were suspended in N-methyl-2-pyrrolidinone (270 ml) and stirred at 150° C. for 23 hours. After cooling off, the reaction mixture was poured into water, filtered through Celite, and the filtrate was extracted with ether. The organic layer was washed with saturated brine, dried over anhydrous sodium sulfate and condensed under reduced pressure. The resulting oily residue was distilled to provide 3-chloro-2-fluoropyridine (76.14 g) as a colorless oily substance.

Boiling point: 91-95° C. (15 mmHg)

(2) To a solution of diisopropylamine (97 ml) in THF (1200 ml), n-butyl lithium (2.66M-hexane solution, 239 ml) was added at −78° C. The reaction liquid was stirred for 30 minutes at said temperature, and into which a solution of the above compound (76.14 g) in THF (300 ml) was added dropwise, followed by an hour's stirring. Dry ice was added to the reaction liquid, and after the temperature of the system was raised to the ambient level, the reaction mixture was poured into water and condensed under reduced pressure. The residue was extracted with ether. Hydrochloric acid was added to the aqueous phase to adjust the latter's pH to 2, followed by extraction with ethyl acetate. The organic layer was combined with the extract and washed with saturated brine, dried over anhydrous magnesium sulfate and condensed under reduced pressure. The residue was recrystallized from ether-hexane to provide 3-chloro-2-fluoroisonicotinic acid (55.9 g).

(3) To a solution of 2,2,6,6-tetramethylpiperidine (8 ml) in THF (100 ml), n-butyl lithium (1.56 M-hexane solution, 39.1 ml) was added at −78° C. After stirring at said temperature for 30 minutes, the above compound (2.68 g) was added, followed by 2.5 hours' stirring. To the reaction solution, a solution of 1-benzyl-4-piperidone (3.68 ml) in THF (55 ml) was added dropwise at −78° C., stirred for 20 minutes and the temperature of the system was raised to the ambient level. 3N-hydrochloric acid was added to the reaction mixture to adjust the pH of the latter to 2, followed by 30 minutes' stirring, addition of 4N sodium hydroxide solution to adjust the pH to 5, and extraction with ethyl acetate. The organic layer was washed with saturated brine, dried over anhydrous magnesium sulfate and condensed under reduced pressure. The resulting oily residue was purified on silica gel column chromatography (methanol/chloroform=1/50-1/20-1/10) to provide 1'-benzylspiro [4-chloro-5-fluoro-6-azaisobenzofuran-1(3H), 4-piperidin]-3-one (4.06 g).

(4) The above compound was dissolved in toluene (60 ml) and to the solution diisobutyl aluminum hydride (1.0M-hexane solution, 12.6 ml) was added at −78° C., followed by 30 minutes' stirring. Raising the system temperature to the ambient level, the reaction mixture was poured into saturated aqueous ammonium chloride solution and the insoluble matter was filtered off. The filtrate was condensed under reduced pressure. The residue was extracted with ethyl acetate, and the organic layer was washed with saturated brine and dried over anhydrous magnesium sulfate. The organic layer was condensed under reduced pressure, and the resulting residue was recrystallized from ethyl acetate-heptane to provide 1'-benzylspiro-[4-chloro-5-fluoro-6-azaisobenzofuran-1(3H), 4'-piperidin]-3-ol (2.36 g).

(5) To a solution of above compound (10.9 g) in acetonitrile (400 ml), triethylsilane (135 ml) and boron trifluoride-diethyl ether complex (35.6 ml) were added at 60° C., followed by 30 minutes' stirring. After cooling off, the reaction mixture was adjusted to pH7 with 3N hydrochloric acid and condensed under reduced pressure. The resulting residue was adjusted of its pH to 1 with 5N hydrochloric acid, followed by 2 hours' stirring. The residue was extracted with ether. The resulting aqueous layer was adjusted of its pH to 6 with 8N sodium hydroxide solution and extracted with ethyl acetate. The organic layer was combined with the extract, washed with saturated brine, dried over anhydrous magnesium sulfate and condensed under reduced pressure. Thus obtained oily residue was purified on silica gel column chromatography (hexane/ethyl acetate=2/1), and the resulting solid was recrystallized from ether-hexane to provide 1'-benzylspiro[4-chloro-5-fluoro-6-azaisobenzofuran-1 (3H), 4'-piperidine] (6.67 g).

(6) The above compound was suspended in methanol (150 ml), and to which 20% palladium hydroxide-on-carbon (13 g) was added, followed by an hour's stirring at room temperature in hydrogen atmosphere. The reaction liquid was filtered through Celite, and the filtrate was condensed under reduced pressure to provide the title compound (4.36 g) as a white solid.

1H-NMR (300 MHz, CD3OD, δ ppm): 2.02-2.07 (2H, m), 2.15-2.26 (2H, m), 3.31-3.46 (4H, m), 5.14 (2H, s), 7.05 (1H, t, J=1.1 Hz), 8.10 (1H, s).

Referential Example 38

Spiro[6-fluoro-5-azaisobenzofuran-1(3H), 4'-piperidine]

(1) Referential Example 37-(3) was repeated except that 3-chloro-2-fluoroisonicotinic acid used in Referential Example 37-(3) was replaced with 6-chloronicotinic acid, to provide 1'-benzylspiro-[6-chloro-5-azaisobenzofuran-1 (3H), 4'-piperidin]-3-one.

(2) The above compound (2.76 g) and potassium fluoride (2.05 g) were suspended in DMSO (42 ml) and stirred for 14 hours at 140° C. After cooling off, the reaction mixture was poured into water and extracted with ethyl acetate. The organic layer was washed with saturated brine, dried on anhydrous sodium sulfate and condensed under reduced pressure. The resulting residue was purified on silica gel column chromatography (hexane/ethyl acetate=1/2) to provide 1'-benzylspiro [6-fluoro-5-azaisobenzofuran-1(3H), 4'-piperidin]-3-one (2.06 g).

(3) Referential Example 35-(4)-(6) were repeated except that 1'-benzylspiro[4-chloro-5-fluoro-6-azaisobenzofuran-1 (3H), 4'-piperidin]-3-one which was used in Referential Example 35-(4) was replaced with the above compound, to provide the title compound.

Example 1

2-(3,4-Difluorophenyl)-2-(2-oxo-1-pyrrolidinyl)-N-[3-(spiro[6-fluoroisobenzofuran-1(3H), 4'-piperidin]-1-yl)propyl]acetamide (1) To a solution of spiro[6-fluoroisobenzofuran-1(3H), 4'-pieridine]hydrochloride (50 mg) in DMF (1.5 ml), potassium carbonate (85 mg), potassium iodide (3 mg) and N-(3-bromopropyl) phthalimide (55 mg) were added by the order stated, and stirred for 4 hours at 80° C. The reaction liquid was cooled to room temperature and water was added, followed by extraction with ethyl acetate. The organic layer was washed with saturated brine, dried over anhydrous sodium sulfate and condensed under reduced pressure. The resulting residue was purified on silica gel column chromatography (ethyl acetate) to provide 2-(3-spiro[6-fluoroisobenzofuran-1(3H), 4'-piperidin-1-yl]-propyl)-IH-isoindol-1,3(2H)-dione (53 mg) as a pale yellow solid.

(2) To a solution of above compound (1.57 g) in ethanol (2 ml), hydrazine monohydrate (0.033 ml) was added and heated under reflux for 4 hours. The reaction liquid was cooled to room temperature and condensed under reduced pressure. The solid was separated by filtration and washed with carbon tetrachloride. The filtrate was condensed under reduced pressure to provide 3-spiro[6-fluoroisobenzofuran-1(3H), 4'-piperidin-1-yl]propanamine (39 mg) as a pale yellow, oily substance.

(3) To a solution of above compound in DMF (1.5 ml), 2-(3,4-difluorophenyl)-2-(2-oxo-1-pyrrolidinyl)acetic acid (33 mg), HoBt monohydrate (30 mg), sodium hydrogencarbonate (43 mg) and EDCl (37 mg) were added by the order stated, and stirred for 15 hours at room temperature. Water was added to the reaction liquid which then was extracted with ethyl acetate. The organic layer was washed with saturated brine, dried over anhydrous sodium sulfate and condensed under reduced pressure. The resulting residue was purified on silica gel column chromatography (methanol-ethyl acetate=15/85) to provide the title compound (20 mg) as a pale yellow, oily substance.

1H-NMR (300 MHz, CDCl3, δ ppm): 1.55-2.11 (8H, m), 2.28-2.55 (6H, m), 2.72-2.78 (1H, m), 2.85-2.91 (1H, m), 3.02-3.10 (1H, m), 3.35-3.51 (2H, m), 3.73-3.81 (1H, m), 5.00 (2H, s), 5.77 (1H, s), 6.88-7.00 (2H, m), 7.11-7.33 (4H, m), 7.86 (1H, brs).

ESI-MS Found: m/z 502 [M+H]+

Example 2-8

Example 1 was repeated except that spiro[6-fluoroisobenzofuran-1(3H)-4'-piperidine]hydrochloride used in Example 1-(1) and 2-(3,4-difluorophenyl)-2-(2-oxo-1-pyrrolidinyl)-acetic acid were replaced with starting materials corresponding respectively to the intended compounds, to provide compounds of Examples 2-8.

Example 2

2,2-Bis(4-chlorophenyl)-N-[3-(2,3-dihydrospiro-[1H-indan-1,4'-piperidin]-1-yl)propyl]acetamide 1H-NMR (300 MHz, CDCl3, δ ppm): 1.51-1.59 (2H, m), 1.66-1.83 (4H, m), 1.91 (2H, t, J=7.3 Hz), 2.07-2.16 (2H, m), 2.45 (2H, t, J=6.2 Hz), 2.79-2.93 (4H, m), 3.39-3.44 (2H, m), 4.76 (1H, s), 7.12-7.39 (13H, m).

ESI-MS Found: m/z 507 [M+H]+

Example 3

2-(3,4-Difluorophenyl)-2-(2-oxo-1-pyrrolidinyl)-N-(3-(spiro[isobenzofuran-1(3H), 4'-piperidin]-1-yl) propyl]acetamide 1H-NMR (300 MHz, CDCl3, δ ppm): 1.65-2.17 (10H, m), 2.40-2.60 (6H, m), 2.98-3.08 (1H, m), 3.38-3.50 (2H, m), 3.71-3.80 (2H, m), 5.05 (1H, s), 5.76 (1H, s), 7.13-7.31 (7H, m), 7.92 (1H, s).

ESI-MS Found: m/z 484 [M+H]+

Example 4

2-(4-Chlorophenyl)-2-(2-oxo-1-pyrrolidinyl)-N-[3-(spiro[isobenzofuran-1-(3H), 4'-piperidin]-1-yl)propyl]acetamide ESI-MS Found: m/z 482 [M+H]+

Example 5

2-(3,4-Difluorolphenyl)-2-(2-oxo-1-pyrrolidinyl)-N-[3(spiro-[isobenzofuran-1(3H), 4'-piperidin]-1-yl) propyl]acetamide ESI-MS Found: m/z 474 [M+H]+

Example 6

2-(3,4-Difluorophenyl)-2-(2-oxo-1-pyrrolidinyl)-N-[3-(spiro[5-fluoroisobenzofuran-1(3H), 4'-piperidin]-1-yl)propyl]-acetamide ESI-MS Found: m/z 502 [M+H]+

Example 7

2-(3,4-Difluorophenyl)-2-(2-oxo-1-pyrrolidinyl)-N-[3-(4-(6-fluoro-3-pyridinyl)piperidin]-1-yl) propyl] acetamide ESI-MS Found: m/z 475 [M+H]+

Example 8

2-(3,4-Difluorophenyl)-2-(2-oxo-1-piperidinyl)-N-[3-(spiro-[isobenzofuran-1(3H), 4'-piperidin]-1-yl) propyl]acetamide 1H-NMR (300 MHz, CDCl3, δ ppm): 1.42-3.10 (15H, m), 3.10-3.76 (2H, m), 5.06 (2H, s), 7.00-7.50 (10H, m), 7.63-7.78 (1H, m), 8.42-8.74 (2H, m).

ESI-MS Found: m/z 506 [M+H]+

Example 9

2-(3,4-Difluorophenyl)-N-methyl-2-(2-oxo-1-pyrrolidinyl)-N-[3-(spiro[isobenzofuran-1(3H), 4'-piperidin]-1-yl) propyl]acetamide (1) To a solution of tert-butyl N-(3-hydroxypropyl)-N-methylcarbamate (12.0 g) and triethylamine (11.5 ml) in ethyl acetate (300 ml), methanesulfonyl chloride (5.4 ml) was added under cooling with ice. After 2 hours' stirring, saturated aqueous sodium hydrogencarbonate solution was added to the reaction liquid and extracted with ethyl acetate. The organic layer was washed with saturated brine, dried over anhydrous sodium sulfate and condensed under reduced pressure to provide 3-[(tert-butoxycarbonyl)-(methyl)amino]propyl methanesulfonate (14.8 g) as an oily substance.

(2) To a solution of above compound (5.00 g) in DMF (50 ml), spiro[isobenzofuran-1(3H), 4'-piperidine]hydrochloride (4.22 g), potassium carbonate (12.92 g) and potassium iodide (310 g) were added by the order stated, and stirred for 18 hours at 80° C. The reaction liquid was cooled to room temperature, to which water was added, followed by extraction with ethyl acetate. The organic layer was washed with saturated brine, dried over anhydrous sodium sulfate and condensed under reduced pressure. The resulting residue was purified on silica gel column chromatography (methanol/ethyl acetate=1/9) to provide tert-butyl N-methyl-N-[3-(spiro [isobenzofuran-1(3H), 4'-piperidin]-1-yl)propyl]-carbamate (4.71 g) as a pale yellow oily substance.

(3) To a solution of above compound (4.58 g) in ethyl acetate (40 ml), 4N-hydrogen chloride-ethyl acetate solution (30 ml) was added and stirred for 18 hours at room temperature. The solid which precipitated was recovered by filtration and washed with ether to provide N-methyl-3-(spiro[isobenzofuran-1(3H), 4'-piperidin-1-yl]-1-propanamine dihydrochloride (3.22 g) as a white powder.

(4) The title compound was obtained by repeating Example 1-(3) except that 3-spiro[6-fluoroisobenzofuran-1(3H), 4'-piperidin-1-yl]-propanamine which was used in Example 1-(3) was replaced with the above compound.

1H-NMR (300 MHz, CDCl3, δ ppm): 1.70-2.10 (8H, m), 2.25-2.46 (6H, m), 2.65-2.90 (3H, m), 2.91 (3H×½, s), 2.99 (3H×½, s), 3.20-3.55 (2H, m), 3.86-3.92 (6H, m), 5.05 (2H× ½, s), 5.06 (2H×½, s), 6.11 (1H×½, s), 6.25 (1H×½, s), 7.02-7.27 (7H, m).

ESI-MS Found: m/z 498 [M+H]+

Examples 10-29

Example 9-(4) was repeated except that 2-(3,4-difluorophenyl)-2-(2-oxo-1-pyrrolidinyl)acetic acid which was used in Example 9-(4) was replaced with starting materials corresponding respectively to the intended compounds, to provide compounds of Examples 10-29.

Example 10

2-(3,4-Difluorophenyl)-N-methyl-2-(2-oxo-1,3-oxazolan-3-yl)-N-[3-(spiro[isobenzofuran-1(3H), 4'-piperidin]-1-yl)propyl]acetamide 1H-NMR (300 MHz, CDCl3, δ ppm): 1.74-2.31 (6H, m), 2.25-2.50 (4H, m), 2.62-3.19 (3H, m), 3.30-3.55 (2H, m), 4.18-4.40 (3H, m), 5.05 (1H, s), 5.06 (1H, s), 5.86 (1H×½, s), 6.03 (1H×½, s), 7.13-7.31 (7H, m).
ESI-MS Found: m/z 500 [M+H]+

Example 11

2-(4-Chlorophenyl)-2-cyclopentyl-N-methyl-N-[3-(spiro-[isobenzofuran-1(3H), 4'-piperidin]-1-yl)propyl]acetamide 1H-NMR (300 MHz, CDCl3, δ ppm): 0.89-2.23 (16H, m), 2.30-3.00 (7H, m), 3.08-3.50 (4H, m), 4.73-5.60 (2H, m), 6.82-7.45 (8H, m).
ESI-MS Found: m/z 481 [M+H]+

Example 12

2-(4-Chlorophenyl)-N-methyl-2-(1H-pyrrol-1-yl)-N-[3-(spiro-[isobenzofuran-1(3H), 4'-piperidin]-1-yl)propyl]acetamide 1H-NMR (300 MHz, CDCl3, δ ppm): 1.50-2.10 (6H, m), 2.25-2.51 (4H, m), 2.68-3.05 (2H, m), 2.96 (3H×½, s), 3.01 (3H×½, s), 3.30-3.40 (1H, m), 3.45-3.55 (1H, m), 5.07 (2H, s), 6.01 (1H×½, s), 6.18-6.25 (2H, m), 6.39 (1H×½, s), 6.67-6.76 (2H, m), 7.05-7.39 (8H, m).
ESI-MS Found: m/z 478 [M+H]+

Example 13

2-(4-Chlorophenyl)-2-cyclopentyl-2-hydroxy-N-methyl-N-[3-(spiro[isobenzofuran-1(3H), 4'-piperidin]-1-yl)propyl]acetamide 1H-NMR (300 MHz, CDCl3, δ ppm): 1.00-4.13 (27H, m), 5.06 (2H, s), 6.98-7.72 (8H, m).
ESI-MS Found: m/z 497 [M+H]+

Example 14

2-(4-Chlorophenyl)-N-methyl-2-(1H-pyrazol-1-yl)-N-[3-(spiro-[isobenzofuran-1(3H), 4'-piperidin]-1-yl)propyl]acetamide 1H-NMR (300 MHz, CDCl3, δ ppm): 1.59-2.10 (6H, m), 2.28-2.51 (4H, m), 2.69-2.95 (2H, m), 2.98 (3H×½, s), 3.02 (3H×½, s), 3.20-3.65 (2H, m), 5.07 (2H, s), 6.25-6.30 (1H, s), 6.48 (1H×½, s), 6.84 (1H×½, s), 7.09-7.45 (9H, m), 7.51-7.58 (1H, m).
ESI-MS Found: m/z 479 [M+H]+

Example 15

2-(4-Chlorophenyl)-2-hydroxy-2-isopropyl-N-methyl-N-[3-(spiro[isobenzofuran-1(3H), 4'-]2-piperidin]-1-yl)propyl]acetamide 1H-NMR (300 MHz, CDCl3, δ ppm): 0.55-3.02 (25H, m), 5.08 (2H, s), 7.10-7.58 (8H, m).
ESI-MS Found: m/z 471 [M+H]+

Example 16

2-(4-Chlorophenyl)-2-hydroxy-N-methyl-2-(3-pyridyl)-N-[3-(spiro[isobenzofuran-(3H), 4'-piperidin]-1-yl)propyl]acetamide 1H-NMR (300 MHz, CDCl3, δ ppm): 1.42-3.10 (15H, m), 3.10-3.76 (2H, m), 5.06 (2H, s), 7.00-7.50 (10H, m), 7.63-7.78 (1H, m), 8.42-8.74 (2H, m).

Example 17

2-(3,4-Difluorophenyl)-N-methyl-2-(2-oxo-1-piperidinyl)-N-[3-(spiro[isobenzofuran-1(3H), 4'-piperidin]-1-yl)propyl]acetamide 1H-NMR (300 MHz, CDCl3, δ ppm): 1.43-3.65 (20H, m), 5.06 (1H, s), 5.07 (1H, s), 6.87 (1H×½, s), 7.10-7.40 (6H, m), 7.44 (1H×½, s), 7.67 (1H, d, J=20 Hz), 7.80 (1H, d, J=1.7 Hz).
ESI-MS Found: m/z 498 [M+H]+

Example 18

2-(3,4-Difluorophenyl)-N-methyl-2-(1H-1,2,3-triazol-1-yl)-N-[3-(spiro[isobenzofuran-1(3H), 4'-piperidin]-1-yl)propyl]acetamide 1H-NMR (300 MHz, CDCl3, δ ppm): 1.43-3.65 (20H, m), 5.06 (1H, s), 5.070 (1H, s), 6.87 (1H×½, s), 7.10-7.40 (6H, m), 7.44 (1H×½, s), 7.67 (1H, d, J=2.0 Hz), 7.80 (1H, d, J=1.7 Hz).
ESI-MS Found: m/z 482 [M+H]+

Example 19

2-(3,4-Difluorophenyl)-N-methyl-2-phenyl-N-[3-(spiro-[isobenzofuran-1(3H), 4'-piperidin]-1-yl)propyl]acetamide 1H-NMR (300 MHz, CDCl3, δ ppm): 1.67-2.01 (6H, m), 2.32-2.44 (4H, m), 2.73-2.85 (2H, m), 2.99 (1H×½, s), 3.00 (1H×½, s), 3.29-3.57 (2H, m), 5.07 (2H, s), 5.14 (1H×½, s), 5.35 (1H×½, s), 6.92-6.96 (1H, m), 7.03-7.14 (3H, m), 7.15-7.37 (8H, m).
ESI-MS Found: m/z 491 [M+H]+

Example 20

2-(3,4-Difluorophenyl)-N-methyl-2-(1H-1,2,4-triazol-1-yl)-N-[3-(spiro[isobenzofuran-1(3H), 4'-piperidin]-1-yl)propyl]acetamide 1H-NMR (300 MHz, CDCl3, δ ppm): 1.55-3.66 (18H, m), 5.07 (1H, s), 5.08 (1H, s), 6.45 (1H×½, s), 7.05 (1H×½, s), 7.10-7.42 (6H, m), 7.90 (1/2H, s), 7.94 (1/2H, s), 8.20 (1H, s).

ESI-MS Found: m/z 482 [M+H]+

Example 21

2-(4-Chlorophenyl)-2-cyclopentyl-2-methyl-N-methyl-N-[3-(spiro[isobenzofuran-1(3H), 4'-piperidin]-1-yl)propyl]acetamide ESI-MS Found: m/z 495 [M+H]+

Example 22

2-(4-Chlorophenyl)-N-methyl-2-(2-oxo-1-pyrrolidinyl)-N-[3-(spiro[isobenzofuran-1(3H), 4'-piperidin]-1-yl)propyl]acetamide ESI-MS Found: m/z 496 [M+H]+

Example 23

2-(4-Fluorophenyl)-N-methyl-2-(2-oxo-1-pyrrolidinyl)-N-[3-(spiro[isobenzofuran-1(3H), 4'-piperidin]-1-yl)propyl]acetamide ESI-MS Found: m/z 480 [M+H]+

Example 24

2-(4-Chlorophenyl)-2-(1H-imidazol-1-yl)-N-methyl-N-[3-(spiro-[isobenzofuran-1(3H), 4'-piperidin]-1-yl)propyl]acetamide ESI-MS Found: m/z 479 [M+H]+

Example 25

2-(3,4-Difluorophenyl)-N-methyl-2-(2-methyl-1H-imidazol-1-yl)-N-[3-(spiro[isobenzofuran-1(3H), 4'-piperidin]-1-yl)propyl]acetamide ESI-MS Found: m/z 495 [M+H]+

Example 26

2-(3,4-Difluorophenyl)-N-methyl-2-(4-methyl-1H-imidazol-1-yl)-N-[3-(spiro[isobenzofuran-1(3H), 4'-piperidin]-1-yl)propyl]-acetamide ESI-MS Found: m/z 495 [M+H]+

Example 27

2-(3,4-Difluorophenyl)-2-(4-(methanesulfonyl)-2-oxo-1-piperazinyl)-N-methyl-N-[3-(spiro[isobenzofuran-1(3H), 4'-pipridin]-1-yl)propyl]acetamide ESI-MS Found: m/z 591 [M+H]+

Example 28

2-(3,4-Difluorophenyl)-N-methyl-2-(2H-1,2,3,4-tetrazol-2-yl)-N-[3-(spiro[isobenzofuran-1(3H), 4'-piperidin]-1-yl)propyl]acetamide 1H-NMR (300 MHz, CDCl3, δ ppm): 1.8-3.2 (13H, m), 2.97 (3H×½, s), 3.00 (3H×½, s), 3.4-3.7 (2H, m), 5.05 (1H, s), 5.07 (1H, s), 6.85 (1H×½, m), 7.04-7.13 (1H, m), 7.18-7.35 (5H, m), 7.41-7.51 (1H, m), 7.74 (1H×½, s), 8.50 (1H×½, s), 8.52 (1H×½, s).

ESI-MS Found: m/z 483 [M+H]+

Example 29

2-(3,4-Difluorophenyl)-N-methyl-2-(2-oxo-1(2H)pyridinyl)-N-[3-(spiro[isobenzofuran-1(3H), 4-piperidin]-1-yl)propyl]acetamide 1H-NMR (300 MHz, CDCl3, δ ppm): 1.7-2.1 (6H, m), 2.38-2.50 (4H, m), 2.70-3.02 (2H, m), 3.05 (3H×½, s), 3.08 (3H×½, s), 3.40-3.45 (1H, m), 3.52-3.53 (1H, m), 5.04 (1H, s), 5.05 (1H, s), 6.09-6.13 (1H, m), 6.53-6.57 (1H, m), 7.09-7.34 (10H, m)

ESI-MS Found: m/z 508 [M+H]+

Examples 30-42

Example 9 was repeated except that spiro[6-fluoroisobenzofuran-1(3H), 4'-piperdine]hydrochloride used in Example 9-(2) was replaced with each a starting material corresponding to the intended compound, to provide the compounds of Examples 30-42.

Example 30

2-(3,4-Difluorophenyl)-N-methyl-2-(2-oxo-1-pyrrolidinyl-N-[3-(spiro[7-fluoroisobenzofuran-1(3H), 4'-piperidin]-1-yl)propyl]-acetamide 1H-NMR (400 MHz, CDCl3, δ ppm): 1.56-2.49 (14H, m), 2.66-3.08 (3H, m), 2.90 (3H×½, s), 2.98 (3H×½, s), 3.40-3.51 (2H, m), 3.84-3.91 (1H, m), 5.07 (2H, s), 6.11 (1H×½, s), 6.24 (1H×½, s), 6.88-6.98 (2H, m), 7.04-7.26 (4H, m).

ESI-MS Found: m/z 516 [M+H]+

Example 31

2-(3,4-Difluorophenyl)-N-methyl-2-(2-oxo-1-pyrrolidinyl-N-[3-(4-(4-fluorophenyl)piperidin-1-yl)propyl]acetamide 1H-NMR (300 MHz, CDCl3, δ ppm): 1.60-3.60 (23H, m), 3.38-3.95 (1H, m), 6.12 (1H×½, s), 6.23 (1H×½, s), 6.94-7.26 (7H, m).

ESI-MS Found: m/z 488 [M+H]+

Example 32

2-(3,4-Difluorophenyl)-N-methyl-2-(2-oxo-1-pyrrolidinyl-N-[3-spiro[6-fluoroisobenzofuran-1(3H), 4'-piperidin]-1-yl)-propyl]acetamide 1H-NMR (300 MHz, CDCl3, δ ppm): 1.55-2.15 (8H, m), 2.20-2.60 (6H, m), 2.60-3.05 (6H, m), 3.15-3.60 (2H, m), 3.80-4.00 (1H, m), 4.95-5.05 (2H, m), 6.05-6.20 (1H, m), 6.75-7.25 (6H, m).

ESI-MS Found: m/z 516 [M+H]+

Example 33

2-(3,4-Difluorophenyl)-N-methyl-2-(2-oxo-1-pyrrolidinyl-N-[3-spiro[5-fluoroisobenzofuran-1(3H), 4'-piperidin]-1-yl)-propyl]acetamide 1H-NMR (300 MHz, CDCl3, δ ppm): 1.55-2.15 (8H, m), 2.20-2.55 (6H, m), 2.60-3.05 (6H, m), 3.15-4.00 (3H, m), 4.95-5.05 (2H, m), 6.00-6.20 (1H, m), 6.85-7.25 (6H, m).

ESI-MS Found: m/z 516 [M+H]+

Example 34

2-(3,4-Difluorophenyl)-N-methyl-2-(2-oxo-1-pyrrolidinyl-N-(3-spiro[4-fluoroisobenzofuran-1(3H), 4'-piperidin]-1-yl)-propyl]acetamide 1H-NMR (400 MHz, CDCl3, δ ppm): 1.63-2.07 (8H, m), 2.31-2.48 (6H, m), 2.60-2.99 (3H, m), 2.88 (3H×½, s), 2.90 (3H×½, s), 3.21-3.52 (2H, m), 3.86-3.91 (1H, m), 5.10 (1H, s), 5.11 (1H, s), 6.11 (1H×½, s), 6.25 (1H×½, s), 6.90-6.95 (2H, m), 7.04-7.08 (1H, m), 7.14-7.26 (3H, m).

ESI-MS Found: m/z 516 [M+H]+

Example 35

2-(4-Fluorophenyl)-N-methyl-2-(2-oxo-1-pyrrolidinyl)-N-[3-(spiro[6-azaisobenzofuran-1(3H), 4'-piperidin]-1-yl)propyl]acetamide 1H-NMR (300 MHz, CDCl3, δ ppm): 1.64-3.55 (22H, m), 3.85-3.94 (1H, m), 5.04 (1H×½, s), 5.05 (1H×½, s), 6.12 (1H×½, s), 6.27 (1H×½, s), 7.03-7.07 (1H, m), 7.13-7.23 (3H, m), 8.43 (1H, s), 8.50 (1H, d, J=5.0 Hz).

ESI-MS Found: m/z 499 [M+H]+

Example 36

2-(3,4-Difluorophenyl)-N-methyl-2-(2-oxo-1-pyrrolidinyl)-N-[3-(spiro[5-fluoro-6-azaisobenzofuran-1(3H), 4'-piperidin]-1-yl)propyl]acetamide 1H-NMR (300 MHz, CDCl3, δ ppm): 1.62-3.53 (22H, m), 3.84-4.00 (1H, m), 5.01 (1H×½, s), 5.02 (1H×½, s), 6.11 (1H×½, s), 6.27 (1H×½, s), 6.75 (1H, d, J=1.8 Hz), 7.03-7.06 (1H, m), 7.12-7.22 (2H, m), 7.96 (1H, d, J=2.9 Hz).

ESI-MS Found: m/z 517 [M+H]+

Example 37

2-(3,4-Difluorophenyl)-N-methyl-2-(2-oxo-1-pyrrolidinyl)-N-[3-(2,3-dihydrospiro-[1H-indene-1,4'-piperidin]-1-yl)propyl]acetamide ESI-MS Found: m/z 496 [M+H]+

Example 38

2-(3,4-Difluorophenyl)-N-methyl-2-(2-oxo-1-pyrrolidinyl)-N-[3-(spiro[6-fluoro-5-azaisobenzofuran-1(3H), 4'-piperidin]-1-yl)-propyl]acetamide ESI-MS Found: m/z 517 [M+H]+

Example 39

2-(3,4-Difluorophenyl)-N-methyl-2-(2-oxo-1-pyrrolidinyl)-N-[3-(4-(3-fluorophenyl)piperidin-1-yl)propyl]acetamide ESI-MS Found: m/z 488 [M+H]+

Example 40

2-(3,4-Difluorophenyl)-N-methyl-2-(2-oxo-1-pyrrolidinyl)-N-[3-(4-(2-fluorophenyl)piperidin-1-yl)propyl]acetamide ESI-MS Found: m/z 488 [M+H]+

Example 41

2-(3,4-Difluorophenyl)-N-methyl-2-(2-oxo-1-pyrrolidinyl)-N-[3-(4-(6-fluoro-3-pyridinyl)piperidin-1-yl)propyl]acetamide ESI-MS Found: m/z 489 [M+H]+

Example 42

2-(3,4-Difluorophenyl)-N-methyl-2-(2-oxo-1-pyrrolidinyl)-N-[3-(4-phenylpiperidin-1-yl)propyl]acetamide ESI-MS Found: m/z 470 [M+H]+

Examples 43-45

Example 9 was repeated except that spiro[isobenzofuran-1(3H), 4'-piperidine]hydrochloride which was used in Example 9-(2) was replaced with each a starting material corresponding to the intended compound and 2-(3,4-difluorophenyl)-2-(2-oxo-1-pyrrolidinyl)acetic acid which was used in Example 9-(4), with 2-(3,4-difluorophenyl)-2-(2-methyl-1H-imidazol-1-yl)acetic acid, to provide the compounds of Examples 43-45.

Example 43

2-(3,4-Difluorophenyl)-N-methyl-2-(2-methyl-1H-imidazol-1-yl)-N-[3-(spiro[6-fluoroisobenzofuran-1(3H), 4'-piperidin]-1-yl)-propyl]acetamide 1H-NMR (300 MHz, CDCl3, δ ppm): 1.67-2.03 (6H, m), 2.29-2.52 (7H, m), 2.67-3.13 (5H, m), 3.20-3.62 (2H, m), 5.02 (2H, s), 6.01 (1H×½, s), 6.20 (1H×½, s), 6.70-7.35 (8H, m).

ESI-MS Found: m/z 513 [M+H]+

Example 44

2-(3,4-Difluorophenyl)-N-methyl-2-(2-methyl-1H-imidazol-1-yl)-N-[3-(spiro[5-fluoroisobenzofuran-1(3H), 4'-piperidin]-1-yl)-propyl]acetamide ESI-MS Found: m/z 513 [M+H]+

Example 45

2-(3,4-Difluorophenyl)-N-methyl-2-(2-methyl-1H-imidazol-1-yl)-N-[3-(spiro[5-fluoro-6-azaisobenzofuran-1(3H), 4'-piperidin]-1-yl)-propyl]acetamide ESI-MS Found: m/z 514 [M+H]+

Examples 46-58

Example 9 was repeated except that spiro[isobenzofuran-1(3H), 4'-piperidin]hydrochloride which was used in Example 9-(2) was replaced with spiro[5-fluoro-6-azaisobenzofuran-1(3H), 4'-piperidine], and 2-(3,4-difluorophenyl)-2-(2-oxo-1-pyrrolidinyl)acetic acid which was used in Example 9-(4), with each a starting material corresponding to the intended compound, to provide compounds of Examples 46-58.

Example 46

2-(3,4-Difluorophenyl)-2,2-dimethyl-N-methyl-N-[3-(spiro[5-fluoro-6-azaisobenzofuran-1(3H), 4'-piperidin]-1-yl)propyl]acetamide ESI-MS Found: m/z 462 [M+H]+

Example 47

2-(3,4-Difluorophenyl)-N-methyl-2-(1H-1,2,4-triazol-1-yl)-N-[3-(spiro[5-fluoro-6-azaisobenzofuran-1(3H), 4'-piperidin]-1-yl)propyl]-acetamide ESI-MS Found: m/z 501 [M+H]+

Example 48

2,2-Bis(6-fluoro-3-pyridinyl)-N-methyl-N-[3-(spiro[5-fluoro-6-azaisobenzofuran-1(3H), 4'-piperidin]-1-yl)propyl]-acetamide 1H-NMR (400 MHz, CDCl3, δ ppm): 1.76-1.85 (4H, m), 1.93-1.98 (2H, m), 2.38-2.42 (4H, m), 2.7-2.9 (2H, m), 3.02 (3H×⅖, s), 3.07 (3H×⅗, s), 3.39-3.51 (2H, m), 5.03 (2H, s), 5.22 (1H×⅗, s), 5.40 (1H×⅖, s), 6.77 (1H, s), 6.94 (2H, dd, J=8.4 Hz, 2.9 Hz), 7.7-7.81 (2H, m), 7.97 (1H, s), 8.11 (2H, s).

ESI-MS Found: m/z 512 [M+H]+

Example 49

N-methyl-2,2-bis(6-methoxy-3-pyridinyl)-N-[3-(spiro[5-fluoro-6-azaisobenzofuran-1(3H), 4'-piperidin]-1-yl)propyl]acetamide 1H-NMR (400 MHz, CDCl3, δ ppm): 1.74-1.99 (6H, m), 2.37-2.42 (4H, m), 2.75-2.86 (2H, m), 3.00 (3/2H, s), 3.04 (3/2H, s), 3.39-3.49 (2H, m), 3.91 (6H, s), 5.04 (2H, brd, J=2.8 Hz), 5.05 (1/2H, s), 5.22 (1/2H, s), 6.71 (2H, d, J=8.4 Hz), 6.77 (1H, brs), 7.51-7.57 (2H, m), 7.97-8.02 (3H, m).

ESI-MS Found: m/z 562 [M+H]+

Example 50

2-(6-Fluoro-3-pyridinyl)-2-(4-fluorophenyl)-N-methyl-N-[3-(spiro[5-fluoro-6-azaisobenzofuran-1(3H), 4'-piperidin]-1-yl)propyl]-acetamide ESI-MS Found: m/z 511 [M+H]+

Example 51

2-(6-fluoro-3-pyridinyl)-N-methyl-2-(6-trifluoromethyl-3-pyridinyl)-N-[3-(spiro[5-fluoro-6-azaisobenzofuran-1(3H), 4'-piperidin]-1-yl)propyl]acetamide 1H-NMR (400 MHz, CDCl3, δ ppm): 1.75-2.05 (6H, m), 2.39-2.44 (4H, m), 2.74-2.85 (2H, m), 3.03 (3/2H, s), 3.09 (3/2H, s), 3.37-3.52 (2H, m), 5.04 (2H, brs), 5.31 (1/2H, s), 5.50 (1/2H, s), 6.77 (1H, brs), 6.96 (1H, dd, J=8.8 Hz, J=2.8 Hz), 7.68 (1H, d, J=8.0 Hz), 7.76-7.86 (2H, m), 7.97 (1H, s), 8.15 (1H, s), 8.62 (1H, s).

ESI-MS Found: m/z 562 [M+H]+

Example 52

2-(6-Fluoro-3-pyridinyl)-2-(6-methoxy-3-pyridinyl)-N-methyl-N-[3-(spiro[5-fluoro-6-azaisobenzofuran-1(3H), 4'-piperidin]-1-yl)-propyl]acetamide ESI-MS Found: m/z 524 [M+H]+

Example 53

2-(6-Fluoro-3-pyridinyl)-2-(4-toluyl)-N-methyl-N-[3-(spiro[5-fluoro-6-azaisobenzofuran-1(3H), 4'-piperidin]-1-yl)propyl]-acetamide ESI-MS Found: m/z 507 [M+H]+

Example 54

2-(6-Fluoro-3-pyridinyl)-N-methyl-2-phenyl-N-[3-(spiro[5-fluoro-6-azaisobenzofuran-1(3H), 4'-piperidin]-1-yl)propyl]-acetamide ESI-MS Found: m/z 493 [M+H]+

Example 55

2,2-Bis(4-fluorophenyl)-N-methyl-N-[3-(spiro[5-fluoro-6-azaisobenzofuran-1(3H), 4'-piperidin]-1-yl)propyl]acetamide 1H-NMR (400 MHz, DMSO-d6, δ ppm): 1.05-1.70 (4H, m), 1.83-1.95 (2H, m), 2.13-2.27 (4H, m), 2.60-2.74 (2H, m), 2.85 (3/2H, s), 2.96 (3/2H, s), 3.29-3.41 (1H, m), 3.43-3.52 (1/2H, m), 3.64-3.72 (1/2H, m), 4.97 (2H, s), 5.49 (1/2H, s), 5.54 (1/2H, s), 7.08-7.15 (5H, m), 7.23-7.28 (4H, m), 8.11 (1/2H, s) 8.14 (1/2H, s).

ESI-MS Found: m/z 510 [M+H]+

Example 56

2-(3,4-Difluorophenyl)-N-methyl-2-(1H-pyrrol-1-yl)-N-[3-(spiro[5-fluoro-6-azaisobenzofuran-1(3H), 4'-piperidin]-1-yl)propyl]-acetamide 1H-NMR (400 MHz, CDCl3, δ ppm): 1.60-2.02 (6H, m), 2.34-2.45 (4H, m), 2.71-2.85 (2H, m), 2.97 (3/2H, s), 3.02 (3/2H, s), 3.35-3.39 (1H, m), 3.41-3.48 (1/2H, m), 3.52-3.59 (1/2H, m), 5.03 (2H, s), 6.00 (1/2H, s), 6.21-6.23 (2H, m), 6.31 (1/2H, s), 6.70-6.73 (2H, m), 6.76-6.78 (1H, m), 6.84-6.92 (1H, m), 6.93-7.02 (1H, m), 7.10-7.17 (1H, m), 7.94 (1/2H, s), 7.97 (1/2H, s).

ESI-MS Found: m/z 499 [M+H]+

Example 57

2-(4-Fluorophenyl)-N-methyl-2-(1H-pyrrol-1-yl)-N-[3-(spiro[5-fluoro-6-azaisobenzofuran-1(3H), 4'-piperidin]-1-yl)propyl]acetamide 1H-NMR (400 MHz, CDCl3, δ ppm): 1.78-2.01 (6H, m), 2.34-2.44 (4H, m), 2.70-2.84 (2H, m), 2.96 (3/2H, s), 3.02 (3/2H, s), 3.29-3.42 (1H, m), 3.48-3.51 (1H, m), 5.03 (2H, s), 6.02 (1/2H, s), 6.19-6.20 (2H, m), 6.31 (1/2H, s), 6.69-6.71 (2H, m), 6.77 (1H, s), 7.03-7.08 (2H, m), 7.16-7.23 (2H, m), 7.94 (1/2H, s), 7.97 (1/2H, s).

ESI-MS Found: m/z 481 [M+H]+

Example 58

2-(3,4-Difluorophenyl)-N-methyl-2-(1H-pyrazol-1-yl)-N-[3-(spiro[5-fluoro-6-azaisobenzofuran-1(3H), 4'-piperidin]-1-yl)propyl]-acetamide 1H-NMR (400 MHz, CDCl3, δ ppm): 1.71-2.11 (6H, m), 2.19-2.49 (4H, m), 2.72-2.90 (2H, m), 3.00 (3/2H, s), 3.03 (3/2H, s), 3.26-3.33 (1/2H, m), 3.41-3.58 (3/2H, m), 5.04 (2H, s), 6.29-6.31 (1H, m), 6.47 (1/2H, s), 6.77 (1H, brs), 6.87 (1/2H, s), 7.07-7.14 (1H, m), 7.16-7.26 (2H, m), 7.46-7.50 (1H, m), 7.53-7.55 (1H, m), 7.96 (1/2H, s), 7.99 (1/2H, s).
ESI-MS Found: m/z 500 [M+H]+

Example 59

2-(3,4-Difluorophenyl)-N-methyl-2-(1H)-pyrrol-1-yl)-N-[3-(spiro[6-fluoro-5-azaisobenzofuran-1(3H), 4'-piperidin]-1-yl)propyl]-acetamide Example 9 was repeated except that spiro[isobenzofuran-1(3H), 4'-piperidine]hydrochloride which was used in Example 9-(2) was replaced with spiro[6-fluoro-5-azaisobenzofuran-1(3H), 4'-piperidine], and 2-(3,4-difluorophenyl)-2-(2-oxo-1-pyrrolidinyl)acetic acid, with 2-(3,4-difluorophenyl)-2-(1H-pyrrol-1-yl)acetic acid, to provide the title compound.

1H-NMR (400 MHz, CDCl3, δ ppm): 1.61-1.94 (6H, m), 2.35-2.43 (4H, m), 2.71-2.89 (2H, m), 2.97 (3/2H, s), 3.02 (3/2H, s), 3.35-3.38 (1H, m), 3.41-3.48 (1/2H, m), 3.52-3.59 (1/2H, m), 5.07 (2H, s), 6.00 (1/2H, s), 6.22-6.24 (2H, m), 6.30 (1/2H, s), 6.63-6.68 (1H, m), 6.70-6.73 (2H, m), 6.85-6.91 (1H, m), 6.94-7.02 (1H, m), 7.10-7.18 (1H, m), 8.05 (1H, s).

ESI-MS Found: m/z 499 [M+H]+

Examples 60-61

Example 9 was repeated except that spiro[isobenzofuran-1(3H), 4'-piperidine]hydrochloride which was used in Example 9-(2) was replaced with 4-(3-(propionylamino)phenyl)-1-piperidine (which was synthesized following the method as described in WO02/06245) and 2-(3,4-difluorophenyl)-2-(2-oxo-1-pyrrolidinyl)acetic acid which was used in Example 9-(4), with each a starting material corresponding to the intended compound, to provide compounds of Examples 60-61.

Example 60

2-(3,4-Difluorophenyl)-2,2-dimethyl-N-methyl-N-[3-(4-(3-(propionylamino)phenyl)-1-piperidinyl)propyl]acetamide 1H-NMR (400 MHz, CDCl3, δ ppm): 1.24 (3H, t, J=7.3 Hz), 1.52 (6H, s), 1.82-2.12 (8H, m), 2.36-2.53 (8H, m), 2.7-3.0 (2H, brs), 3.0-3.2 (1H, brs), 3.3-3.5 (1H, brs), 6.93-6.95 (2H, m), 7.00-7.08 (1H, m), 7.10-7.16 (1H, m), 7.19-7.24 (1H, m), 7.24-7.4 (3H, m).

ESI-MS Found: m/z 486 [M+H]+

Example 61

2,2-Bis(6-fluoro-3-pyridinyl)-N-methyl-N-[3-(4-(3-(propionylamino)phenyl)-1-piperidinyl)propyl]acetamide 1H-NMR (400 MHz, CDCl3, δ ppm): 1.22-1.26 (3H, m), 1.68-2.11 (8H, m), 2.36-2.53 (5H, m), 2.94 (1H, d, J=11.4 Hz), 3.01 (1.5H, s), 3.07 (1.5H, s), 3.00-3.08 (1H, m), 3.38-3.51 (2H, m), 5.23 (1H, s), 5.54 (1H, s), 6.89-6.95 (3H, m), 7.19-7.53 (4H, m), 7.72-7.80 (2H, m), 8.09-8.12 (2H, m).

ESI-MS Found: m/z 536 [M+H]+

Examples 62-63

Example 9 was repeated except that spiro[isobenzofuran-1(3H), 4'-piperidine]hydrochloride which was used in Example 9-(2) was replaced with spiro[6-fluoroisobenzofuran-1(3H), 4'-piperidine] and 2-(3,4-difluorophenyl)-2-(2-oxo-1-pyrrolidinyl)acetic acid which was used in Example 9-(4), with each a starting material corresponding to the intended compound, to provide compounds of Examples 62-63.

Example 62

2-(3,4-Difluorophenyl)-N-methyl-2-(2-oxo-1,3-oxazolan-3-yl)-N-[3-(spiro[6-fluoroisobenzofuran-1(3H), 4'-piperidin]-1-yl)propyl]-acetamide ESI-MS Found: m/z 518 [M+H]+

Example 63

2,2-Bis(6-fluoro-3-pyridinyl)-N-methyl-N-[3-(spiro[6-fluoroisobenzofuran-1(3H), 4'-piperidin]-1-yl)propyl]acetamide ESI-MS Found: m/z 511 [M+H]+

Example 64

2,2-Bis(4-fluorophenyl)-N-methyl-N-[3-(4-(6-fluoro-3-pyridinyl)piperidin-1-yl)propyl]acetamide Example 9 was repeated except that spiro[isobenzofuran-1(3H), 4'-piperidine] hydrochloride which was used in Example 9-(2) was replaced with 4-(6-fluoro-3-pyridinyl)piperidine, and 2-(3,4-difluorophenyl)-2-(2-oxo-1-pyrrolidinyl)acetic acid which was used in Example 9-(4), with 2,2-bis(4-fluorophenyl)acetic acid, to provide the title compound.

ESI-MS Found: m/z 482 [M+H]+

Examples 65-66

Example 9 was repeated except that spiro[isobenzofuran-1(3H), 4'-piperidine] hydrochloride which was used in Example 9-(2) was replaced with each a starting material corresponding to the intended compound and 2-(3,4-difluorophenyl)-2-(2-oxo-1-pyrrolidinyl)acetic acid which was used in Example 9-(4), with 2-(6-fluoro-3-pyridinyl)-2-(4-fluorophenyl)acetic acid, to provide the compounds of Examples 65-66.

Example 65

2-(6-Fluoro-3-pyridinyl)-2-(4-fluorophenyl)-N-methyl-N-[3-(spiro[6-fluoro-5-azaisobenzofuran-1(3H), 4-piperidin]-1-yl)propyl]-acetamide ESI-MS Found: m/z 511 [M+H]+

Example 66

2-(6-Fluoro-3-pyridinyl)-2-(4-fluorophenyl)-N-methyl-N-[3-(spiro[6-azaisobenzofuran-1(3H), 4-piperidin]-1-yl)propyl]acetamide ESI-MS Found: m/z 493 [M+H]+

Examples 67-68

Example 9 was repeated except that tert-butyl N-(3-hydroxypropyl)-N-methyl carbamate which was used in Example 9-(1) was replaced with tert-butyl N-(3-hydroxypropyl)-N-ethyl carbamate, and spiro[isobenzofuran-1(3H), 4'-piperidine] hydrochloride used in Example 9-(2) was replaced with each a starting material corresponding to the intended compound, to provide the compounds of Examples 67-68.

Example 67

2-(3,4-Difluorophenyl)-N-ethyl-2-(2-oxo-1-pyrrolidinyl)-N-[3-(spiro[isobenzofuran-1(3H), 4'-piperidin]-1-yl)propyl]acetamide ESI-MS Found: m/z 512 [M+H]+

Example 68

2-(3,4-Difluorophenyl)-N-ethyl-2-(2-oxo-1-pyrrolidinyl)-N-[3-(4-(6-fluoro-3-pyridinyl)piperidin-1-yl)propyl]acetamide ESI-MS Found: m/z 503 [M+H]+

Example 69-70

Example 9 was repeated except that tert-butyl N-(3-hydroxypropyl)-N-methyl carbamate which was used in Example 9-(1) was replaced with each a starting material corresponding to the intended compound, and spiro[isobenzofuran-1(3H), 4'-piperidine] hydrochloride used in Example 9-(2) was replaced with spiro[6-fluoroisobenzofuran-1(3H), 4'-piperidine] to provide the compounds of Examples 69-70.

Example 69

2-(3,4-Difluorophenyl)-2-(2-oxo-1-pyrrolidinyl)-N-propyl-N-[3-(spiro[6-fluoroisobenzofuran-1(3H), 4'-piperidin]-1-yl)propyl]-acetamide ESI-MS Found: m/z 544 [M+H]+

Example 70

2-(3,4-Difluorophenyl)-N-isopropyl-2-(2-oxo-1-pyrrolidinyl)-N-[3-(spiro[6-fluoroisobenzofuran-1(3H), 4'-piperidin]-1-yl)propyl]-acetamide ESI-MS Found: m/z 544 [M+H]+

Example 71

2,2-Bis(6-fluoro-3-pyridinyl)-N-ethyl-N-[3-(spiro[5-fluoro-6-azaisobenzofuran-1(3H), 4'-piperidin]-1-yl)-propyl]acetamide Example 9 was repeated except that tert-butyl N-(3-hydroxypropyl)-N-methyl carbamate which was used in Example 9-(1) was replaced with tert-butyl N-(3-hydroxypropyl)-N-ethyl carbamate, spiro[isobenzofuran-1(3H), 4'-piperidine] hydrochloride used in Example 9-(2) was replaced with spiro[5-fluoro-6-azaisobenzofuran-1(3H), 4'-piperidine] and 2-(3,4-difluorophenyl)-2-(2-oxo-1-pyrrolidinyl)acetic acid which was used in Example 9-(4), with 2,2-bis(6-fluoro-3-pyridinyl)acetic acid, to provide the title compound.

ESI-MS Found: m/z 526 [M+H]+

Examples 72-77

Example 9 was repeated except that tert-butyl N-(3-hydroxypropyl)-N-methyl carbamate which was used in Example 9-(1) was replaced with tert-butyl N-(3-hydroxypropyl)-N-ethyl carbamate, spiro[isobenzofuran-1(3H), 4'-piperidine] hydrochloride used in Example 9-(2) was replaced with spiro[6-fluoroisobenzofuran-1(3H), 4'-piperidine] and 2-(3,4-difluorophenyl)-2-(2-oxo-1-pyrrolidinyl) acetic acid which was used in Example 9-(4), with each a starting material corresponding to the intended compound, to provide the compounds of Examples 72-77.

Example 72

2-(3,4-Difluorophenyl)-N-ethyl-2-(4-(methanesulfonyl)-2-oxo-1-piperazinyl)-N-[3-(spiro[6-fluoroisobenzofuran-1(3H), 4'-piperidin]-1-yl)-propyl] acetamide 1H-NMR (400 MHz, CDCl3, δ ppm): 1.19 (3H, t, J=7.3 Hz), 1.77-2.04 (4H, m), 2.36-2.53 (4H, m), 2.50 (2H, q, J=7.3 Hz), 2.7-2.8 (0.5H, m), 2.86 (3H, s), 2.89-2.96 (2.5H, m), 3.19-3.25 (3H, m), 3.41-3.43 (1H, m), 3.52-3.77 (2H, m), 3.89 (1H, d, J=6.9 Hz), 4.14 (1H, d, J=6.9 Hz), 5.01 (H, s), 5.03 (1H, s), 6.54 (0.5H, s), 6.59 (0.5H, s), 6.81-6.85 (1H, m), 6.94-6.99 (1H, m), 7.06-7.08 (1H, m), 7.12-7.27 (3H, m).

ESI-MS Found: m/z 623 [M+H]+

Example 73

1-(3,4-Difluorophenyl)-N-ethyl-N-[3-(spiro[6-fluoroisobenzofuran-1(3H), 4'-piperidin]-1-yl)propyl]-cyclopentanecarboxamide 1H-NMR (400 MHz, CDCl3, δ ppm): 0.73 (2H, t, J=6.6 Hz), 1.11 (1H, t, J=6.6 Hz), 1.30-1.45 (1H, m), 1.6-2.1 (12H, m), 2.20-2.70 (6H, m), 2.90-3.10 (3H, m), 3.30-3.40 (2H, m), 5.02 (2H, s), 6.80-6.9 (1H, m), 6.93-6.98 (2H, m), 7.00-7.15 (3H, m).

ESI-MS Found: m/z 501 [M+H]+

Example 74

2,2-Bis(6-fluoro-3-pyridinyl)-N-ethyl-N-[3-(spiro[6-fluoroisobenzofuran-1(3H), 4'-piperidin]-1-yl)propyl]acetamide ESI-MS Found: m/z 525 [M+H]+

Example 75

1-(3,4-Difluorophenyl)-N-ethyl-N-[3-(spiro[6-fluoroisobenzofuran-1(3H), 4'-piperidin]-1-yl)propyl]-cyclopropanecarboxamide ESI-MS Found: m/z 473 [M+H]+

Example 76

2-(3,4-Difluorophenyl)-2,2-dimethyl-N-ethyl-N-[3-(spiro[6-fluoroisobenzofuran-1(3H), 4'-piperidin]-1-yl)propyl]acetamide ESI-MS Found: m/z 475 [M+H]+

Example 77

2-(3,4-Difluorophenyl)-N-ethyl-2-(2-oxo-1-pyrrolidinyl)-N-[3-(spiro[6-fluoroisobenzofuran-1(3H), 4'-piperidin]-1-yl)propyl]-acetamide ESI-MS Found: m/z 530 [M+H]+

Example 78

2-(3,4-Difluorophenyl)-N-methyl-2-(2-oxo-1-pyrrolidinyl)-N-[2-hydroxy-3-(spiro[isobenzofuran-1(3H), 4'-piperidin]-1-yl)propyl]-acetamide (1) To a solution of tert-butyl N-methyl-N-(2-oxylanylmethyl) carbamate (300 mg) in DMF (3 ml), spiro[isobenzofuran-1(3), 4'-piperidine] hydrochloride (326 mg) and potassium carbonate (332 mg) were added and stirred for 18 hours at 100° C. The reaction liquid was cooled to room temperature and to which water was added, followed by extraction with ethyl acetate. The organic layer was washed with saturated brine, dried over anhydrous sodium sulfate and condensed under reduced pressure. The resulting residue was purified on silica gel column chromatography (methanol/chloroform=1/20) to provide tert-butyl N-methyl-N-(2-hydroxy-3-(spiro-[isobenzofuran-1(3H), 4'-piperidin]-1-yl)propyl] carbamate (578 mg) as a pale yellow oily substance.

(2) The above compound (326 mg) was dissolved in trifluoroacetic acid and stirred for 30 minutes at room temperature. After condensation of the reaction liquid under reduced pressure, an aqueous sodium hydroxide solution was added to the condensate, followed by extraction with chloroform. The organic layer was washed with saturated brine, dried over anhydrous sodium sulfate and condensed under reduced pressure to provide 2-hydroxy-N-methyl-3-(spiro-[isobenzofuran-1(3H), 4'-piperidin]-1-yl)-propanamine (208 mg) as a pale yellow oily substance.

(3) Using the above compound, the title compound was obtained following Example 1-(3).

ESI-MS Found: m/z 514 [M+H]+

Example 79

2-(3,4-Difluorophenyl)-N-methyl-2-(2-oxo-1-pyrrolidinyl)-N-[3-(spiro[isobenzofuran-1(3H), 4'-piperidin]-1-yl)butyl]acetamide (1) To a solution of spiro[isobenzofuran-1(3H), 4'-piperidine] hydrochloride (2.80 g) and 2-(3-oxobutyl)-1H-isoindol-1,3(2H)-dione (2.0 g) in THF-methanol (1:1 v/v, 40 ml), 0.3 M sodium cyanoborohydride-½ zinc chloride solution in methanol (44 ml) was added and stirred for 20 hours at room temperature. Saturated aqueous sodium hydrogencarbonate solution was added to the reaction liquid, followed by extraction with ethyl acetate. The organic layer was washed with saturated brine, dried over anhydrous sodium sulfate and condensed under reduced pressure. The resulting solid was washed with a small amount of methanol to provide 2-(3-spiro[isobenzofuran-1(3H), 4'-piperidin-1-yl]butyl-1H-isoindol-1,3(2H)-dione (578 mg) as a white solid.

(2) 3-(Spiro[isobenzofuran-1(3H), 4'-piperidin]-1-yl) butanamine which was obtained from the above compound (3.0 g) following Example 1-(2) was dissolved in dioxane (20 ml) and water (20 ml). To the solution triethylamine (2 ml) was added, and into which ethyl chlorocarbonate (0.84 ml) was added dropwise under cooling with ice. After 15 hours' stirring at room temperature, the reaction liquid was condensed under reduced pressure. To the residue saturated aqueous sodium hydrogencarbonate solution was added, followed by extraction with ethyl ether. The organic layer was washed with saturated brine, dried over anhydrous sodium sulfate and condensed under reduced pressure. The resulting residue was purified on silica gel column chromatography (ethyl acetate) to provide ethyl N-methyl-N-[3-(spiro[isobenzofuran-1(3H), 4-piperidin]-1-yl)butyl]carbamate (1.09 g) as a colorless oily substance.

(3) To a solution of above compound (1.09 g) in dioxane (10 ml), lithium aluminum hydride (360 mg) was added and heated under reflux for 12 hours. Cooling the reaction liquid to room temperature, THF (50 ml) and 2N-sodium hydroxide were added, and the system was stirred for 5 hours. After removing the insoluble matter by filtration, the filtrate was condensed under reduced pressure to provide the title compound (900 mg) as a colorless oily substance.

(4) Using above compound, the title compound was obtained following Example 1-(3).

ESI-MS Found: m/z 512 [M+H]+

Example 80

2-(3,4-Difluorophenyl)-N-methyl-2-(2-oxo-1-pyrrolidinyl)-N-[3-(spiro[6-fluoroisobenzofuran-1(3H), 4'-piperidin]-1-yl)butyl]acetamide The title compound was obtained by repeating Example 79, except that spiro[isobenzofuran-1(3H), 4'-piperidine] hydrochloride which was used in Example 79-(1) was replaced with spiro[6-fluoroisobenzofuran-1(3H), 4'-piperidine] hydrochloride.

ESI-MS Found: m/z 530 [M+H]+

Example 81

2-(3,4-Difluorophenyl)-2-(2-oxo-1-pyrrolidinyl)-N-[2-fluoro-3-(spiro[isobenzofuran-1(3H), 4'piperidin]-1-yl)-propyl]acetamide (1) A solution of 2-(2-oxylanylmethyl)-1H-isoindol-1,3 (2H)-dione (112 mg) and spiro[isobenzofuran-1(3H), 4'-piperidine] (105 mg) in DMF (3 ml) was stirred for 18 hours at 90° C. The reaction liquid was cooled to room temperature, to which water was added, followed by extraction with ether. The organic layer was washed with saturated brine, dried over anhydrous sodium sulfate and condensed under reduced pressure. The resulting residue was purified on silica gel column chromatography (ethyl acetate/hexane=2/1) to provide 2-(2-hydroxy-3-spiro[isobenzofuran-1(3H), 4'-piperidin-1-yl] propyl)-1H-isoindol-1,3(2H)-dione (124 mg) as a colorless, amorphous compound.

(2) Using the above compound, 2-hydroxy-3-spiro-[isobenzofuran-1(3H), 4'-piperidin-1-yl] propanamine was obtained in the manner similar to Example 1-(2).

(3) Example 79-(2) was repeated except that ethyl chlorocarbonate used in Example 79-(2) was replaced with di-tert-butylcarbonate, to provide tert-butyl N-[2-hydroxy-3-(spiro [isobenzofuran-1(3H), 4'-piperidin]-1-yl)-propyl]carbamate.

(4) To a solution of above compound (210 mg) and pyridine (0.25 ml) in dichloromethane (5 ml), diethylaminosulfatrifluoride (0.16 ml) was added dropwise under cooling with ice. After 2 hours' stirring, saturated aqueous sodium hydrogencarbonate solution was added, followed by extraction with ethyl acetate. The organic layer was washed with saturated brine, dried over anhydrous sodium sulfate and condensed under reduced pressure. The resulting residue was purified on silica gel column chromatography (ethyl acetate/hexane=1/1) to provide tert-butyl-N-[2-fluoro-3-(spiro-[isobenzofuran-1 (3H), 4'-piperidin]-1-yl)propyl]carbamate (50 mg).

(5) The above compound (50 mg) was dissolved in trifluoroacetic acid (1 ml), and stirred for 30 minutes at room temperature. Condensing the reaction liquid under reduced pressure, aqueous sodium hydroxide solution was added to the condensate and extracted with chloroform. The organic layer was washed with saturated brine, dried over anhydrous sodium sulfate and condensed under reduced pressure to provide 2-fluoro-3-(spiro-[isobenzofuran-1(3H), 4'-piperidin]-1-yl) propanamine (34 mg) as a pale yellow oily substance.

(6) Using the above compound, the title compound was obtained following Example 1-(3)

ESI-MS Found: m/z 502 [M+H]+

Example 82

2-(4-Chlorophenyl)-2-hydroxy-N-methyl-2-(2-thiazolyl)-N-[3-(spiro[isobenzofuran-1(3H), 4'-piperidin]-1-yl)propyl]acetamide (1) To a solution of N-methyl-3-(spiro[isobenzofuran-1 (3H), 4'-piperidin]-1-yl)-1-propanamine (260 mg) in DMF (2 ml), 2-(4-chlorophenyl)-2-oxoacetic acid (244 mg), HOBt (18.5 mg), EDCl (242 mg) and sodium hydrogencarbonate (215 mg) were added and stirred for 20 hours. The reaction liquid was diluted with water, extracted with diethyl ether, washed with saturated brine and dried over anhydrous sodium sulfate. The organic layer was condensed under reduced pressure, and the resulting residue was purified on silica gel column chromatography (methanol/chloroform=1/10) to provide 24-chlorophenyl)-N-methyl-2-oxo-N-[3-(spiro [isobenzofuran-1(3H), 4'-piperidin]-1-yl) propyl]acetamide (270 mg) as a yellow, oily substance.

(2) To a solution of 2-bromothiazole (52 mg) in diethyl ether (2 ml), 1.6M n-butyl lithium solution in hexane (0.81 ml) was added at −78° C. After 15 minutes' stirring at the same temperature, a solution of the above compound (80 mg) in diethyl ether (2 ml) was added, and the temperature was raised to the ambient level. Saturated aqueous ammonium chloride solution was added to the reaction solution and extracted with diethyl ether. The organic layer was washed with saturated brine, dried over anhydrous sodium sulfate and condensed under reduced pressure. The resulting residue was purified on preparative TLC (methanol/chloroform=1/20) to provide the title compound (34.6 mg) as a brown oily substance.

ESI-MS Found: m/z 512 [M+H]+

Example 83

2-(4-Chlorophenyl)-2-(6-fluoro-3-pyridyl)-2-hydroxy-N-methylN-[3-(spiro[isobenzofuran-1(3H), 4'-piperidin]-1-yl) propyl]acetamide Example 82 was repeated except that 2-bromothiazole which was used in Example 82-(2) was replaced with 5-bromo-2-fluoropyridine, to provide the title compound.

ESI-MS Found: m/z 524 [M+H]+

Example 84

2-(3,4-Difluorophenyl)-2-(2-fluoro-4-pyridyl)-2-hydroxy-N-methyl-N-[3-(spiro[isobenzofuran-1(3H), 4'-piperidin]-1-yl)propyl]-acetamide (1) Example 82-(1) was repeated except that methyl 2-(4-chlorophenyl-2-oxoacetic acid which was used in Example 82-(1) was replaced with 2-(3,4-difluorophenyl)-2-oxoacetic acid, to provide 2-(3,4-difluorophenyl)-N-methyl-2-oxo-N-[3-(spiro[isobenzofuran-1(3H), 4'-piperidin]-1-yl) propyl]acetamide.

(2) To a solution of 2-fluoro-4-iodopyridine (64 mg) in THF (2 ml), 2M-isopropyl-magnesium chloride ether solution (0.15 ml) was added at −40° C. After 30 minutes' stirring, a solution of the above compound (100 mg) in THF (2 ml) was added and stirred for 30 minutes. Raising the temperature to the ambient level, saturated aqueous ammonium chloride solution was added and extracted with ethyl acetate. The organic layer was washed with saturated brine, dried over anhydrous sodium sulfate and condensed under reduced pressure. The resulting residue was purified on preparative TLC (methanol/chloroform=1/10) to provide the title compound (48 mg) as a colorless oily substance.

ESI-MS Found: m/z 526 [M+H]++

Example 85

2-(3,4-Difluorophenyl)-2-(2-pyrazinyl)-2-hydroxy-N-methyl-N-[3-(spiro[isobenzofuran-1(3H), 4'-piperidin]-1-yl) propyl]acetamide To a solution of 2-iodopyrazine (52.0 mg, 0.253 mmol) in THF (1 ml), n-butyl magnesium chloride (2M-ether solution, 0.11 ml) was added at 0° C. and stirred for 30 minutes. Successively, a solution of 2-(3,4-difluorophenyl)-N-methyl-2-oxo-N-[3-(spiro[isobenzofuran-1(3H), 4'-piperidin]-1-yl) propyl]acetamide (102 mg) in THF (2 ml) was added, stirred for 1.5 hours, heated to room temperature, and saturated aqueous ammonium chloride solution was added. The mixture was extracted with ethyl acetate, washed with saturated brine and dried over anhydrous sodium sulfate. The organic layer was condensed under reduced pressure, and the resulting residue was purified on preparative TLC (methanol/chloroform=1/10) to provide the title compound (25 mg).

1H-NMR (300 MHz, CDCl3, δ ppm): 1.62-3.89 (18H, m), 5.07 (2H, s), 6.60-7.50 (7H, m), 8.29-8.53 (2H, m), 8.70 (1H, s).

ESI-MS Found: m/z 509 [M+H]+

Examples 86-88

Example 82 was repeated except that methyl 2-(4-chlorophenyl)-2-oxoacetic acid and N-methyl-3-(spiro-[isobenzofuran-1(3H), 4'piperidin]-1-yl)-1-propanamine which were used in Example 82-(1) were replaced with, respectively, 2-(3,4-difluorophenyl)-2-oxoacetic acid, and with each a starting material corresponding to the desired compound; and that 2-bromothiazole in Example 82-(2), with 5-bromo-2-fluoropyridine, to provide the compounds of Examples 86-88.

Example 86

2-(3,4-Difluorophenyl)-2-hydroxy-2-(6-fluoro-3-pyridinyl)-N-methyl-N-[3-(4-(6-fluoro-3-pyridinyl)piperidin)-1-yl)propyl]acetamide ESI-MS Found: m/z 517 [M+H]+

Example 87

2-(6-Fluoro-3-pyridinyl)-2-(2,4-difluorophenyl)-2-hydroxy-N-methyl-N-[3-(spiro[6-fluoro-5-azaisobenzofuran-1(3H), 4'-piperidin]-1-yl)propyl]acetamide ESI-MS Found: m/z 515 [M+H]+

Example 88

2-(2,4-Difluorophenyl)-2-(6-fluoro-3-pyridinyl)-2-hydroxy-N-methyl-N-[3-(spiro[6-azaisobenzofuran-1(3H), 4'-piperidin]-1-yl)propyl]acetamide ESI-MS Found: m/z 527 [M+H]+

Example 89

2,2-Bis(4-fluorophenyl)-2-hydroxy-N-methyl-N-[3-(spiro[5-fluoro-6-azaisobenzofuran-1(3H), 4'-piperidin]-1-yl)propyl]acetamide (1) Example 9-(2) was repeated except that Spiro-[isobenzofuran-1(3H), 4'-piperidine] hydrochloride used in Example 9-(2) was replaced with spiro[5-fluoro-6-azaisobenzofuran-1(3H), 4'-piperidine], to provide tert-butyl N-methyl-N-[3-(5-fluoro-6-azaisobenzofuran-1(3H), 4'-piperidin)-1-yl]propyl]carbamate.

(2) To the above compound (200 mg), 4N hydrogen chloride-dioxane solution (6.0 ml) was added at 0° C., and stirred for 30 minutes. To the reaction liquid 4N aqueous sodium hydroxide solution was added and extracted with diethyl ether. The organic layer was washed with saturated brine, dried over anhydrous sodium sulfate and condensed under reduced pressure. Methylene chloride (2.0 ml) and triethylamine (150 μl) were added to the residue, and further ethyl glyoxylate (150 μl) was added dropwise at 0° C. After an overnight's stirring at room temperature, the reaction liquid was added with aqueous sodium hydrogencarbonate solution and extracted with chloroform. The organic layer was washed with saturated brine, dried over anhydrous sodium sulfate and condensed under reduced pressure. The resulting residue was purified on thin layer silica gel column chromatography (methanol/chloroform=10/90) to provide ethyl N-methyl-N-[3-(5-fluoro-6-azaisobenzofuran-1(3H), 4'-piperidin]-1-yl)propyl]oxamate (86.1 mg) as a yellow oily substance.

ESI-MS Found: m/z 380 [M+H]+

(3) To a solution of the above compound (39.6 mg) in tetrahydrofuran (3.0 ml), 2.0M diethyl ether solution (155 μl) of 4-fluorophenyl magnesium bromide was added at 0° C., and stirred for 4.5 hours. Further 2.0M diethyl ether solution (155 μl) of 4-fluorophenyl magnesium bromide was added, followed by 2 hours' stirring. Water was added to the reaction liquid which then was extracted with ethyl acetate. The organic layer was washed with saturated brine, dried over anhydrous sodium sulfate and condensed under reduced pressure. The resulting residue was purified on reversed phase HPLC (acetonitrile: H₂O=10%-95%, gradient) to provide the title compound (14.6 mg) as a colorless oily substance.

1H-NMR (400 MHz, DMSO-d6, δ ppm): 1.75-2.01 (6H, m), 2.26-2.45 (4H, m), 2.58 (3/2H, s), 2.71-2.88 (2H, m), 3.02 (3/2H, s), 3.35-3.38 (1H, m), 3.55-3.59 (1H, m), 5.03 (2H, s), 5.97 (1H, brs), 6.77 (1H, s), 7.01-7.10 (4H, m), 7.34-7.35 (4H, m), 7.91 (1/2H, s) 7.98 (1/2H, s).

ESI-MS Found: m/z 526 [M+H]+

Hereinafter structures of those compounds of Examples are shown in Tables 2-7.

TABLE 2

| Example | Structural Formula |
|---|---|
| 1 |  |
| 2 | 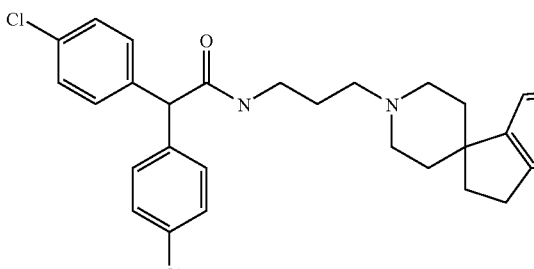 |
| 3 | 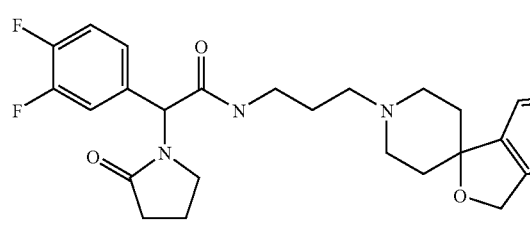 |
| 4 | 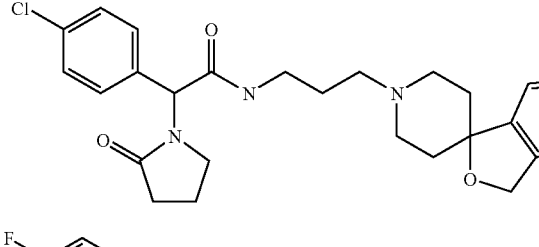 |
| 5 | 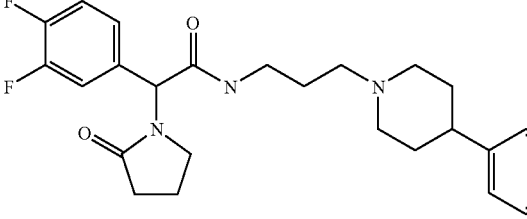 |

TABLE 2-continued

| Example | Structural Formula |
|---|---|
| 6 | |
| 7 | |
| 8 | |
| 9 | |
| 10 | |
| 11 | |

TABLE 2-continued

| Example | Structural Formula |
|---|---|
| 12 | |
| 13 | |
| 14 | |
| 15 | |
| 16 | |

TABLE 3

| Example | Structural Formula |
|---|---|
| 17 | |

TABLE 3-continued

| Example | Structural Formula |
|---|---|
| 18 | (3,4-difluorophenyl)(1H-1,2,3-triazol-1-yl)acetic acid N-methyl-N-[3-(spiro[isobenzofuran-1,4'-piperidin]-1'-yl)propyl]amide |
| 19 | 2-(3,4-difluorophenyl)-2-phenyl-N-methyl-N-[3-(spiro[isobenzofuran-1,4'-piperidin]-1'-yl)propyl]acetamide |
| 20 | (3,4-difluorophenyl)(1H-1,2,4-triazol-1-yl)acetic acid N-methyl-N-[3-(spiro[isobenzofuran-1,4'-piperidin]-1'-yl)propyl]amide |
| 21 | 2-(4-chlorophenyl)-2-cyclopentyl-N-methyl-N-[3-(spiro[isobenzofuran-1,4'-piperidin]-1'-yl)propyl]propanamide |
| 22 | 2-(4-chlorophenyl)-2-(2-oxopyrrolidin-1-yl)-N-methyl-N-[3-(spiro[isobenzofuran-1,4'-piperidin]-1'-yl)propyl]acetamide |
| 23 | 2-(4-fluorophenyl)-2-(2-oxopyrrolidin-1-yl)-N-methyl-N-[3-(spiro[isobenzofuran-1,4'-piperidin]-1'-yl)propyl]acetamide |

TABLE 3-continued

| Example | Structural Formula |
|---|---|
| 24 | (4-chlorophenyl)(imidazol-1-yl)acetyl-N-methyl-N-[3-(spiro[isobenzofuran-1,4'-piperidin]-1'-yl)propyl]amide |
| 25 | (3,4-difluorophenyl)(2-methylimidazol-1-yl)acetyl-N-methyl-N-[3-(spiro[isobenzofuran-1,4'-piperidin]-1'-yl)propyl]amide |
| 26 | (3,4-difluorophenyl)(4-methylimidazol-1-yl)acetyl-N-methyl-N-[3-(spiro[isobenzofuran-1,4'-piperidin]-1'-yl)propyl]amide |
| 27 | (3,4-difluorophenyl)[4-(methylsulfonyl)-2-oxopiperazin-1-yl]acetyl-N-methyl-N-[3-(spiro[isobenzofuran-1,4'-piperidin]-1'-yl)propyl]amide |
| 28 | (3,4-difluorophenyl)(tetrazol-2-yl)acetyl-N-methyl-N-[3-(spiro[isobenzofuran-1,4'-piperidin]-1'-yl)propyl]amide |

TABLE 3-continued
| Example | Structural Formula |
|---|---|
| 29 | 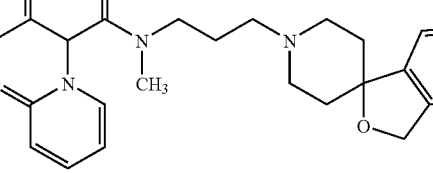 |
| 30 |  |
| 31 | 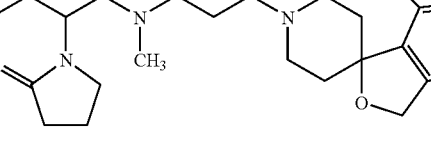 |
| 32 | 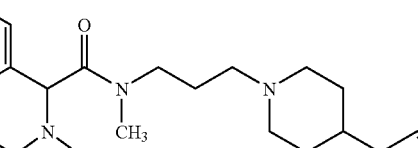 |
TABLE 4
| Example | Structural formula |
|---|---|
| 33 | |
| 34 | |

TABLE 4-continued

| Example | Structural formula |
|---|---|
| 35 | |
| 36 | |
| 37 | |
| 38 | |
| 39 | |
| 40 | |

TABLE 4-continued
| Example | Structural formula |
| --- | --- |
| 41 | 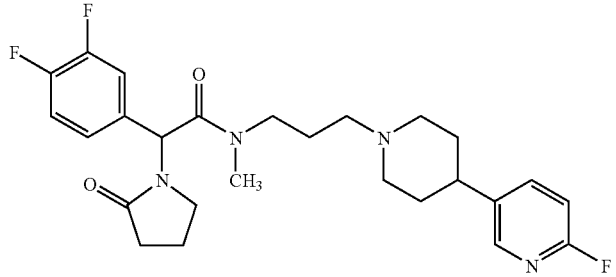 |
| 42 | 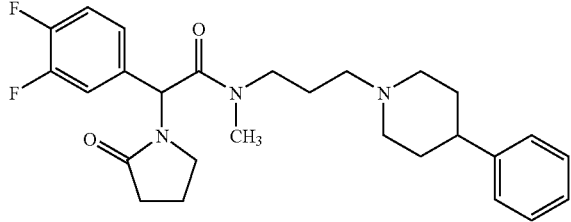 |
| 43 | 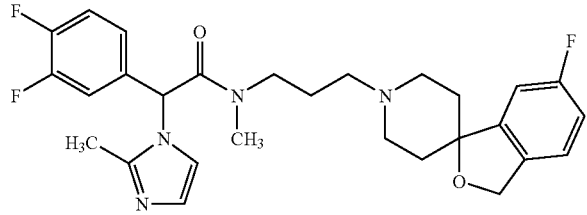 |
| 44 | 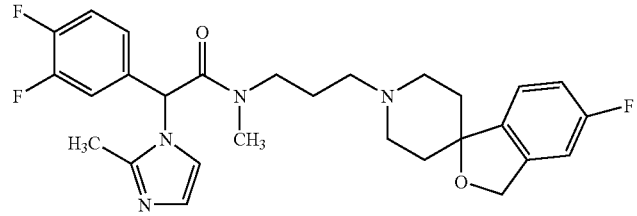 |
| 45 | 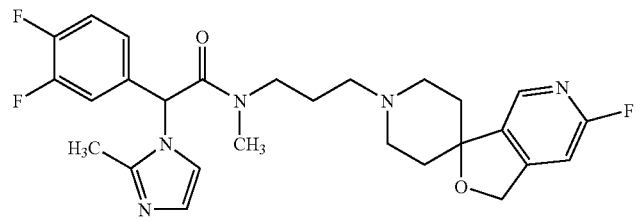 |
| 46 | 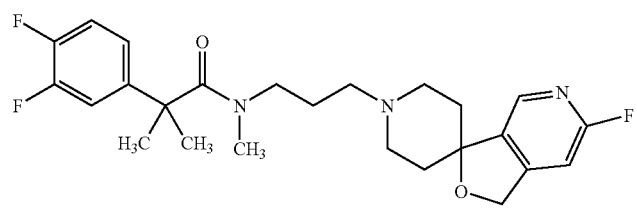 |

TABLE 4-continued

| Example | Structural formula |
|---|---|
| 47 | (structure) |
| 48 | (structure) |

TABLE 5

| Example | Structural Formula |
|---|---|
| 49 | (structure) |
| 50 | (structure) |
| 51 | (structure) |

TABLE 5-continued

| Example | Structural Formula |
|---|---|
| 52 | |
| 53 | |
| 54 | |
| 55 | |
| 56 | |
| 57 | |

TABLE 5-continued

| Example | Structural Formula |
| --- | --- |
| 58 | |
| 59 | |
| 60 | |
| 61 | |
| 62 | |

TABLE 5-continued
| Example | Structural Formula |
|---|---|
| 63 | 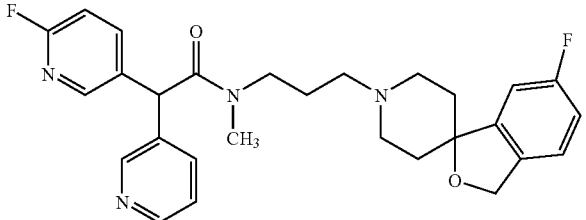 |
| 64 | 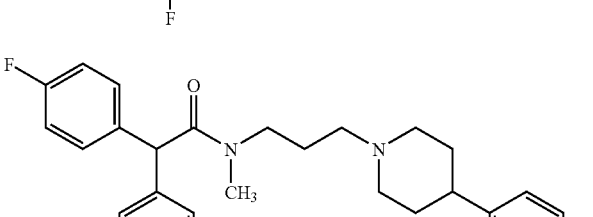 |
TABLE 6
| Example | Structural Formula |
|---|---|
| 65 | 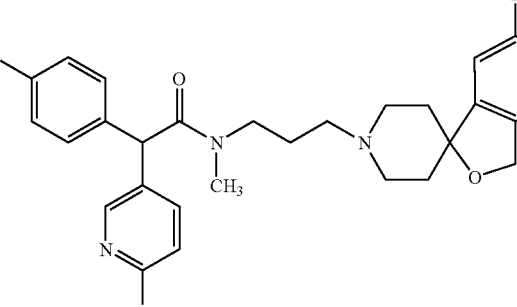 |
| 66 | 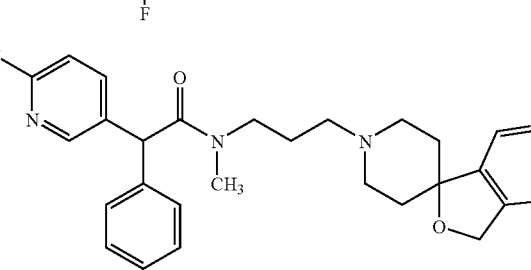 |
| 67 | 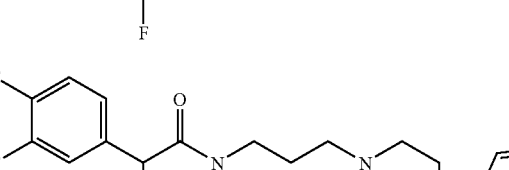 |

TABLE 6-continued

| Example | Structural Formula |
|---|---|
| 68 | |
| 69 | |
| 70 | |
| 71 | |
| 72 | |

TABLE 6-continued

| Example | Structural Formula |
| --- | --- |
| 73 | |
| 74 | |
| 75 | |
| 76 | |
| 77 | |
| 78 | |

TABLE 6-continued
| Example | Structural Formula |
|---|---|
| 79 | 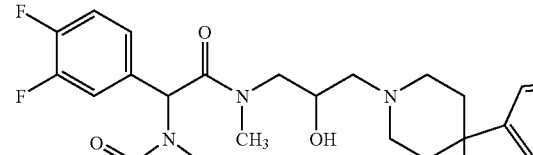 |
| 80 | 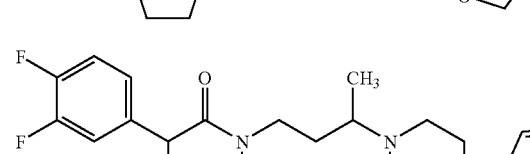 |
TABLE 7
| Example | Structural Formula |
|---|---|
| 81 | 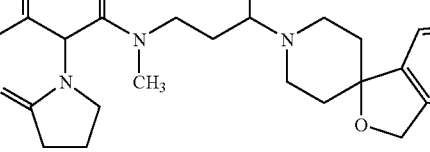 |
| 82 | 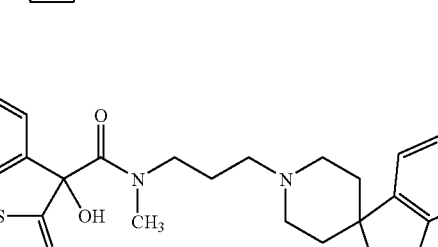 |
| 83 | 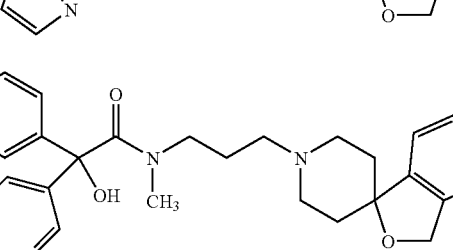 |
| 84 | 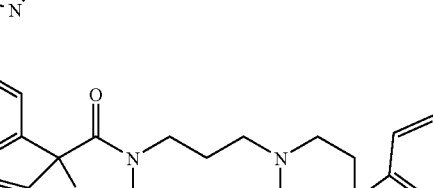 |

TABLE 7-continued

| Example | Structural Formula |
|---------|-------------------|
| 85 | |
| 86 | |
| 87 | |
| 88 | |
| 89 | |

INDUSTRIAL UTILIZABLITY

The compounds of the present invention exhibit MCH-1R antagonistic action and are useful as preventing or treating agents of metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attentiondeficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

The invention claimed is:
1. A compound of structural formula I-1:

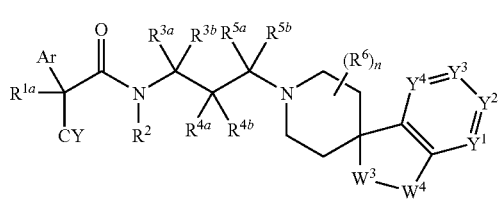

[I-1]

or a pharmaceutically acceptable salt thereof,
wherein:
$R^{1a}$ is selected from: hydrogen, hydroxyl, and optionally halogen-substituted lower alkyl;
$R^2$ is optionally halogen-substituted lower alkyl;
$R^{3a}$, $R^{3b}$, $R^{5a}$ and $R^{5b}$ are each independently selected from: hydrogen and optionally halogen-substituted lower alkyl;
$R^{4a}$ and $R^{4b}$ are each independently selected from: hydrogen, halogen, hydroxyl, and optionally halogen-substituted lower alkyl;
each $R^6$ is independently selected from: hydrogen, halogen and optionally halogen-substituted lower alkyl;
n is selected from an integer between 1 and 8;
$W^3$ is —O—,
$W^4$ is —CH$_2$—,
CY is cyclopentane ring, cyclohexane ring, prrolidine ring, morpholine ring, piperazine ring, pyperidine ring, benzene ring, dihydropyridine ring, pyridine ring, pyrazine ring, pyrimidine ring, pyrrole ring, pyrazole ring, imidazole ring, triazole ring, tetrazole ring, oxazole ring, oxadiazole ring, oxazolidine ring and thiazole ring; which is optionally substituted with two or more substituents selected from Group α,
$Y^1$, $Y^2$, $Y^3$ and $Y^4$ are each independently selected from: —CH—, —CF—, —C(NHCOCH$_3$)—, —C(NHCOC$_2$H$_5$)— and —N—,
with the proviso that not all of $Y^1$ to $Y^4$ are simultaneously nitrogen atoms;
Ar is a benzene ring, a pyridine ring, a pyrazine ring or a pyrimidine ring, unsubstituted or substituted with one or two substituents selected from Group β:
each Group α is independently selected from: halogen, hydroxyl, amino, nitro, oxo, mono-lower alkylamino, di-lower alkylamino, optionally halogen-substituted lower alkyl, optionally fluorine-substituted lower alkyloxy, lower cycloalkyloxy, lower alkyloxycabonyl, (lower alkyloxycarbonyl)amino, (lower alkyloxycarbonyl)lower alkylamino, lower alkylcarbonyl, lower alkylcarbonyloxy, (lower alkylcarbonyl)amino, (lower alkylcarbonyl)lower alkylamino, carbamoyl, mono-lower alkylcarbamoyl, di-lower alkylcarbamoyl, carbamoylamino, mono-lower alkylcarbamoylamino, di-lower alkylcarbamoylamino, (mono-lower alkylcarbamoyl) lower alkylamino, (di-lower alkylcarbamoyl)lower alkylamino, carbamoyloxy, mono-lower alkylcarbamoyloxy, di-lower alkylcarbamoyloxy, lower alkylsulfonyl, lower alkylsulfonylamino, sulfamoyl, mono-lower alkylsulfamoyl, di-lower alkylsulfamoyl, sulfamoylamino, (mono-lower alkylsulfamoyl)amino, (di-lower alkylsulfamoyl)amino, (mono-lower alkylsulfamoyl) lower alkylamino and (di-lower alkylsulfamoyl)lower alkylamino; and
each Group β is independently selected from: nitro, aryloxy, lower cycloalkyl, lower cycloalkyloxy, lower alkylenedioxy, halogen, hydroxyl, optionally hydroxyl- or fluorine-substituted lower alkyl and optionally fluorine-substituted lower alkyloxy.

2. The compound according to claim 1, wherein $R^{1a}$ is hydrogen, methyl or hydroxyl; and pharmaceutically acceptable salts thereof.

3. The compound according to claim 1, wherein both $R^{3a}$ and $R^{3b}$ are hydrogen atoms; and pharmaceutically acceptable salts thereof.

4. The compound according to claim 1, wherein $R^{4a}$ and $R^{4b}$ are selected from the group consisting of hydrogen, fluorine and hydroxyl;
and pharmaceutically acceptable salts thereof.

5. The compound according to claim 1, wherein $R^{5a}$ and $R^{5b}$ are hydrogen or methyl; and pharmaceutically acceptable salts thereof.

6. The compound according to claim 1, wherein each $R^6$ is hydrogen; and pharmaceutically acceptable salts thereof.

7. The compound according to claim 1, wherein CY is a substituent selected from the group consisting of phenyl, 4-fluorophenyl, 4-chlorophenyl, 3,4-difluorophenyl, 4-methoxyphenyl, 4-tolyl, 4-trifluoromethylphenyl, pyridinyl, pyridin-3-yl, pyrazinyl, pyrimidinyl, 6-fluoropyridin-3-yl, 2-fluoropyridin-4-yl, 6-trifluoromethylpyridin-3-yl, 6-methoxypyridin-3-yl, pyrrol-1-yl, pyrazolyl, imidazolyl, 2-methylimidazolyl, 4-methylimidazolyl, 1,2,3-triazol-1-yl, 4-methyl-1,2,3-triazol-1-yl, 1,2,4-triazol-1-yl, 1,2,3,4-tetrazol-1-yl, 1,2,3,4-tetrazol-2-yl, thiazolyl, pyrrolidin-1-yl, piperidinyl, 2-piperidon-1-yl, 2-pyridon-1-yl, 2-pyrrolidon-1-yl, oxazolidin-2-on-1-yl, 4-methanesulfonyl-piperazin-2-on-1-yl, cyclohexyl and cyclopentyl; or a pharmaceutically acceptable salt thereof.

8. The compound according to claim 1, wherein Ar is a substituent selected from the group consisting of phenyl, 4-fluorophenyl, 3,4-difluorophenyl, 4-chlorophenyl, 4-methoxyphenyl, 4-tolyl, 4-trifluoromethylphenyl, pyridinyl, 6-fluoropyridin-3-yl, 6-trifluoromethylpyridin-3-yl, and 6-methoxypyridin-3-yl;
and pharmaceutically acceptable salts thereof.

9. The compound according to claim 1 selected from the group consisting of:
(1) 2-(3,4-difluorophenyl)-N-methyl-2-(1H-1,2,3-triazol-1-yl)-N-[3-(spiro[isobenzofuran-1(3H), 4'-piperidin]-1-yl)propyl]acetamide,
(3) 2-(3,4-difluorophenyl)-N-methyl-2-(2H-1,2,3,4-tetrazol-2-yl)-N-[3-(spiro[isobenzofuran-1(3H), 4'-piperidin]-1-yl)propyl]acetamide, (3) 2-(3,4-difluorophenyl)-N-methyl-2-(2-oxo-1(2H)pyridinyl)-N-[3-(spiro[isobenzofuran-1(3H), 4'-piperidin]-1-yl)propyl]acetamide,
(4) 2-(3,4-difluorophenyl)-N-methyl-2-(2-oxo-1-pyrrolidinyl)-N-[3-(spiro[5-fluoroisobenzofuran-1(3H), 4'-piperidin]-1-yl)propyl]-acetamide,
(5) 2-(3,4-difluorophenyl)-N-methyl-2-(2-methyl-1H-imidazol-1-yl)-N-[3-(spiro[6-fluoroisobenzofuran-1(3H), 4'-piperidin]-1-yl)propyl]-acetamide,
(6) 2-(3,4-difluorophenyl)-N-methyl-2-(2-methyl-1H-imidazol-1-yl)-N-[3-(spiro[5-fluoro-6-azaisobenzofuran-1(3H), 4'-piperidin]-1-yl)propyl]acetamide,
(7) 2,2-bis(6-fluoro-3-pyridinyl)-N-methyl-N-[3-(spiro[5-fluoro-6-azaisobenzofuran-1(3H), 4'-piperidin]-1-yl)propyl]acetamide,
(8) 2-(3,4-difluorophenyl)-N-ethyl-2-(2-oxo-1-pyrrolidinyl)-N-[3-(spiro[isobenzofuran-1(3H), 4'-piperidin]-1-yl)propyl]acetamide,
(9)-2-(3,4-difluorophenyl)-N-ethyl-2-(4-methanesulfonyl)-2-oxo-1-piperazinyl)-N43-(spiro[6-fluoroisobenzofuran-1(3H), 4'-piperidin]-1-yl)propyl]acetamide, and or a pharmaceutically acceptable salt thereof.

10. The compound according to claim 1 selected from the group consisting of:
(1) 2-(4-fluorophenyl)-N-methyl-2-(2-oxo-1-pyrrolidinyl)-N-[3-(spiro[6-azaisobenzofuran-1(3H), 4'-piperidin]-1-yl)propyl]acetamide,
(2) 2-(3,4-difluorophenyl)-N-methyl-2-(2-oxo-1-pyrrolidinyl)-N-[3-(spiro[5-fluoro-6-azaisobenzofuran-1(3H), 4'-piperidin]-1-yl)propyl]acetamide,
(3) 2-(3,4-difluorophenyl)-N-methyl-2-(2-oxo-1-pyrrolidinyl)-N-[3-(spiro[6-fluoro-5-azaisobenzofuran-1(3H), 4'-piperidin]-1-yl)-propyl]acetamide,
(4) 2-(3,4-difluorophenyl)-N-methyl-2-(2-methyl-1H-imidazol-1-yl)-N-[3-(spiro[5-fluoro-6-azaisobenzofuran-1(3H), 4'-piperidin]-1-yl)-propyl]acetamide,
(5) 2-(3,4-difluorophenyl)-2,2-dimethyl-N-methyl-N-[3-(spiro[5-fluoro-6-azaisobenzofuran-1(3H), 4'-piperidin]-1-yl)propyl]acetamide,
(6) 2-(3,4-difluorophenyl)-N-methyl-2-(1H-1,2,4-triazol-1-yl)-N-[3-(spiro[5-fluoro-6-azaisobenzofuran-1(3H), 4'-piperidin]-1-yl)propyl]-acetamide,
(7) 2,2-bis(6-fluoro-3-pyridinyl)-N-methyl-N-[3-(spiro[5-fluoro-6-azaisobenzofuran-1(3H), 4'-piperidin]-1-yl)-acetamide,
(8) N-methyl-2,2-bis(6-methoxy-3-pyridinyl)-N-[3-(spiro[5-fluoro-6-azaisobenzofuran-1(3H), 4'-piperidin]-1-yl)propyl]acetamide,
(9) 2-(6-fluoro-3-pyridinyl)-2-(4-fluorophenyl)-N-methyl-N-[3-(spiro[5-fluoro-6-azaisobenzofuran-1(3H), 4'-piperidin]-1-yl)propyl]-acetamide,
(10) 2-(6-fluoro-3-pyridinyl)-N-methyl-2-(6-trifluoromethyl-3-pyridinyl)-N-[3-(spiro[5-fluoro-6-azaisobenzofuran-1(3H), 4'-piperidin]-1-yl)propyl]acetamide,
(11) 2-(6-fluoro-3-pyridinyl)-2-(6-methoxy-3-pyridinyl)-N-methyl-N-[3-(spiro[5-fluoro-6-azaisobenzofuran-1(3H), 4'-piperidin]-1-yl)-propyl]acetamide,
(12) 2-(6-fluoro-3-pyridinyl)-2-(4-toluyl)-N-methyl-N-[3-(spiro[5-fluoro-6-azaisobenzofuran-1(3H), 4'-piperidin]-1-yl)propyl]-acetamide,
(13) 2-(6-fluoro-3-pyridinyl)-N-methyl-2-phenyl-N-[3-(spiro[5-fluoro-6-azaisobenzofuran-1(3H), 4'-piperidin]-1-yl)propyl]-acetamide,
(14) 2,2-bis(4-fluorophenyl)-N-methyl-N-[3-(spiro[5-fluoro-6-azaisobenzofuran-1(3H), 4'-piperidin]-1-yl) propyl]acetamide,
(15) 2-(3,4-difluorophenyl)-N-methyl-2-(1H-pyrrol-1-yl)-N-[3-(spiro[5-fluoro-6-azaisobenzofuran-1(3H), 4'-piperidin]-1-yl)propyl]-acetamide,
(16) 2-(4-fluorophenyl)-N-methyl-2-(1H-pyrrol-1-yl)-N-[3-(spiro[5-fluoro-6-azaisobenzofuran-1(3H), 4'-piperidin]-1-yl)propyl]acetamide,
(17) 2-(3,4-difluorophenyl)-N-methyl-2-(1H-pyrazol-1-yl)-N-[3-(spiro[5-fluoro-6-azaisobenzofuran-1(3H), 4'-piperidin]-1-yl)propyl]acetamide,
(18) 2-(3,4-difluorophenyl)-N-methyl-2-(1H-pyrrol-1-yl)-N-[3-(spiro[6-fluoro-5-azaisobenzofuran-1(3H), 4'-piperidin]-1-yl)propyl]-acetamide,
(19) 2-(6-fluoro-3-pyridinyl)-2-(4-fluorophenyl)-N-methyl-N-[3-(spiro[6-fluoro-5-azaisobenzofuran-1(3H), 4-piperidin]-1-yl)propyl]-acetamide,
(20) 2-(6-fluoro-3-pyridinyl)-2-(4-fluorophenyl)-N-methyl-N-[3-(spiro[6-azaisobenzofuran-1(3H), 4-piperidin]-1-yl)propyl]acetamide,
(21) 2,2-bis(6-fluoro-3-pyridinyl)-N-ethyl-N-[3-(spiro[5-fluoro-6-azaisobenzofuran-1(3H), 4'-piperidin]-1-yl)-propyl]acetamide,
(22) 2-(6-fluoro-3-pyridinyl)-2-(2,4-difluorophenyl)-2-hydroxy-N-methyl-N-[3-(spiro[6-fluoro-5-azaisobenzofuran-1(3H), 4'-piperidin]-1-yl)propyl]acetamide,
(23) 2-(2,4-difluorophenyl)-2-(6-fluoro-3-pyridinyl)-2-hydroxy-N-methyl-N-[3-(spiro[6-azaisobenzofuran-1(3H), 4'-piperidin]-1-yl)propyl]acetamide, or
(24) 2,2-bis(4-fluorophenyl)-2-hydroxy-N-methyl-N-[3-(spiro[5-fluoro-6-azaisobenzofuran-1(3H), 4'-piperidin]-1-yl)propyl]acetamide, or a pharmaceutically acceptable salt thereof.

11. A method for producing a compound according to claim 1 of general formula [1-1], which comprises:
(1) amidating a compound represented by a general formula [IIa]:

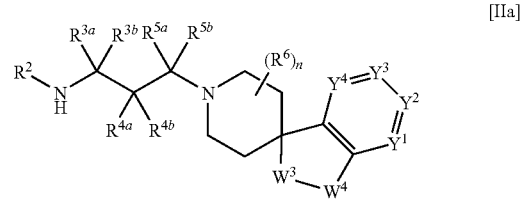

[IIa]

wherein $R^2$, $R^{3a}$, $R^{3b}$, $R^{4a}$, $R^{4b}$, $R^{5a}$, $R^{5b}$, $R^6$, $Y^1$, $Y^2$, $Y^3$, $Y^4$, $W^3$, $W^4$ and n are as in claim 1, with a compound represented by a general formula (IIIa)

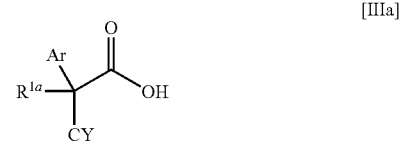

[IIIa]

wherein: Ar, $R^{1a}$ and CY are as in claim 1.

* * * * *